US011364309B2

(12) United States Patent
Cotney et al.

(10) Patent No.: US 11,364,309 B2
(45) Date of Patent: Jun. 21, 2022

(54) NEURONAL ENHANCERS

(71) Applicants: Norwegian University of Science and Technology (NTNU), Trondheim (NO); University of Connecticut, Farmington, CT (US)

(72) Inventors: Justin Cotney, Guilford, CT (US); Clifford Kentros, Malvik (NO); Stefan Blankvoort, Trondheim (NO); Rajeevkumar Raveendran Nair, Trondheim (NO)

(73) Assignees: NORWEGIAN UNIVERSITY OF SCIENCE AND TECHNOLOGY (NTNU), Trondheim (NO); UNIVERSITY OF CONNECTICUT, Farmington, CT (US)

( * ) Notice: Subject to any disclaimer, the term of this patent is extended or adjusted under 35 U.S.C. 154(b) by 345 days.

(21) Appl. No.: 16/181,723

(22) Filed: Nov. 6, 2018

(65) Prior Publication Data
US 2019/0247516 A1 Aug. 15, 2019

Related U.S. Application Data

(60) Provisional application No. 62/584,282, filed on Nov. 10, 2017.

(51) Int. Cl.
| | |
|---|---|
| *A61K 48/00* | (2006.01) |
| *C12N 7/00* | (2006.01) |
| *C12N 15/113* | (2010.01) |
| *A61P 25/28* | (2006.01) |
| *C12N 5/10* | (2006.01) |

(52) U.S. Cl.
CPC ...... *A61K 48/0041* (2013.01); *A61K 48/0058* (2013.01); *A61P 25/28* (2018.01); *C12N 5/10* (2013.01); *C12N 7/00* (2013.01); *C12N 15/113* (2013.01); *C12N 2310/122* (2013.01); *C12N 2310/3519* (2013.01); *C12N 2310/531* (2013.01); *C12N 2750/14143* (2013.01); *C12N 2750/14171* (2013.01)

(58) Field of Classification Search
CPC .................................................. A61K 48/0058
See application file for complete search history.

(56) References Cited

U.S. PATENT DOCUMENTS

| 8,524,499 B2 | 9/2013 | Goldman et al. |
| 2015/0044187 A1 | 2/2015 | Visel et al. |
| 2016/0200763 A1 | 7/2016 | Eldar-Finkelman et al. |

OTHER PUBLICATIONS

Vermunt, et al.; "Large-Scale Identification of Coregulated Enhancer Networks in the Adult Human Brain"; Cell Reports; 2014; vol. 9; pp. 767-779.
Vermunt, et al.; "Transcriptional Dynamics at Brain Enhancers: from Functional Specialization to Neurodegeneration"; Current Neurology and Neuroscience Reports; 2016; vol. 16, Issue 94; pp. 1-10.
Watakabe, et al.; "Comparative Analyses of Adeno-Associated Viral Vector Serotypes 1, 2, 5, 8 and 9 in Marmoset, Mouse and Macaque Cerebral Cortex"; Neuroscience Research; 2015; vol. 93; pp. 144-157.
Witter, et al., "Architecture of the Entorhinal Cortex A Review of Entorhinal Anatomy in Rodents with Some Comparative Notes"; Frontiers in Systems Neuroscience; 2017; vol. 11; Article 46; pp. 1-12.
Zufferey, et al.; "Woodchuck Hepatitis Virus Posttranscriptional Regulatory Element Enhances Expression of Transgenes Delivered by Retroviral Vectors"; Journal of Virology; 1999; vol. 73, Issue 4; pp. 2886-2892.
Aschauer, et al.; "Analysis of Transduction Efficiency, Tropism and Axonal Transport of AAV Serotypes 1, 2, 5, 6, 8 and 9 in the Mouse Brain"; PLOS ONE; 2013, vol. 8, Issue 9; e76310; pp. 1-16.
Axelsen, et al.; "Gene Therapy for Parkinson's Disease, An Update"; Journal of Parkinson's Disease; 2018; vol. 8, pp. 195-215.
Balazs, et al.; "Liposomes for Use in Gene Delivery"; Journal of Drug Delivery; 2011; Article ID 326497; pp. 1-12.
Blankvoort, et al.; "Enhanced Transgenics: A Novel Means to Generate Neuroanatomically-Specific Genetic Tools"; Abstracts Poster JJJ56; Neuroscience, Nov. 13, 2016; pp. 1-2.
Blankvoort, et al.; "Marked Diversity of Unique Cortical Enhancers Enables Neuron-Specific Tools by Enhancer-Driven Gene Expression (EDGE)"; Current Biology; 2018; vol. 28; pp. 2103-2114.
Blankvoort, et al.; Poster F18-3069; "The Marked Diversity of Unique Cortical Enhancers Enables Neuron-Specific Tools by Enhancer-Driven Gene Expression (EDGE)"; FENS Jul. 7-11, 2018; 1 page.
Bouard, et al.; "Viral Vectors: From Virology to Transgene Expression"; British Journal of Pharmacology; 2008; vol. 157; pp. 153-165.
Callaway, et al.; "Monosynaptic Circuit Tracing with Glycoprotein-Deleted Rabies Viruses"; Journal of Neuroscience; 2015; vol. 35, Issue 24; pp. 8985-8979.
Chan, et al.; "Engineered AAVs for Efficient Noninvasive Gene Delivery to the Central and Peripheral Nervous Systems"; Nature Neuroscience; 2017; vol. 20, No. 8; pp. 1172-1181.
Chaplot, et al.; "Dendrimers for Gene Delivery—A Potential Approach for Ocular Therapy?"; Journal of Pharmacy and Pharmacology; 2013; vol. 66; pp. 542-556.
Chen, et al.; "Ultrasensitive Fluorescent Proteins for Imaging Neuronal Activity"; Nature; 2013; vol. 499; pp. 295-302.
Chow, et al.; "An Overview of APP Processing Enzymes and Products"; Neuromolecular Medicine; 2010; vol. 12, No. 1; pp. 1-12.

(Continued)

*Primary Examiner* — Valarie E Bertoglio
(74) *Attorney, Agent, or Firm* — Cantor Colburn LLP

(57) ABSTRACT

A delivery vehicle which comprises a nucleic acid construct, wherein the nucleic acid construct comprises (i) an enhancer which specifically drives gene expression in cells of the entorhinal cortex (ii) a promoter; and (iii) a therapeutic gene, wherein said enhancer, promoter and therapeutic gene are operatively linked, said enhancer and therapeutic gene are heterologous, and said delivery vehicle is suitable for delivery of the nucleic acid construct to the brain of a mammal.

14 Claims, 17 Drawing Sheets
(14 of 17 Drawing Sheet(s) Filed in Color)
Specification includes a Sequence Listing.

(56) References Cited

OTHER PUBLICATIONS

Costa, et al.; "Viral and Non-Viral Gene Therapy for Glioblastoma: New Insights into the Treatment of Malignant Brain Tumors"; Journal of Genetic Syndromes and Gene Therapy; 2013; vol. 4, Issue 7; pp. 1-9.
Delzor, et al.; "Restricted Transgene Expression in the Brain with Cell-Type Specific Neuronal Promoters"; Human Gene Therapy Methods; 2012; vol. 23, pp. 242-254.
Deverman, et al.; "Cre-dependent Selection Yields AAV Variants for Widespread Gene Transfer to the Adult Brain"; Nature Biotechnology; 2016; vol. 34; No. 2; pp. 204-209.
Dias, et al.; "Molecular Genetics and Emerging Therapies for Retinitis Pigmentosa: Basic Research and Clinical Perspectives"; Progress in Retinal and Eye Research; 2018; vol. 63; pp. 107-131.
Dimidschstein, et al.; "A Viral Strategy for Targeting and Manipulating Interneurons Across Vertebrate Species"; Nature Neuroscience; 2016; vol. 19, Issue 12; pp. 1743-1748.
Flotte, et al.; "Expression of the Cystic Fibrosis Transmembrane Conductance Regulator from a Novel Adeno-associated Virus Promoter"; Journal of Biological Chemistry; 1993; vol. 268, Issue 5; pp. 3781-3790.
Gray, et al.; "Genomic Views of Transcriptional Enhancers: Essential Determinants of Cellular Identity and Activity-Dependent Responses in the CNS"; Journal of Neuroscience; 2015; vol. 35, Issue 41; p. 13819-13826.
Ha, et al.; "Exosomes as Therapeutic Drug Carriers and Delivery Vehicles Across Biological Membranes: Current Perspectives and Future Challenges"; Acta Pharmaceutica Sinica B; 2016; vol. 6, Issue 4; pp. 287-296.
Haberman, et al.; "Novel Transcriptional Regulatory Signals in the Adeno-Associated Virus Terminal Repeat A/D Junction Element"; Journal of Virology; 2000; vol. 74, No. 18; pp. 8732-8739.
Hauck, et al.; "Generation and Characterization of Chimeric Recombinant AAV Vectors"; Molecular Therapy; 2003; vol. 7, No. 3; pp. 420-425.
Holehonnur, et al.; "Adeno-Associated Viral Serotypes Produce Differing Titers and Differentially Transduce Neurons Within the Rat Basal and Lateral Amygdala"; BMC Neuroscience; 2014; vol. 15, Issue 28; pp. 1-14.
Holmes, et al.; "Long-Term Effects of AB42 Immunisation in Alzheimer's Disease: Follow-up of a Randomised, Placebo-Controlled Phase I Trial"; Lancet; 2008; vol. 372, pp. 216-223.
Kanter, et al.; "A Novel Mechanism for the Grid-to-Place Cell Transformation Revealed by Transgenic Depolarization of Medial Entorhinal Cortex Layer II"; Neuron; 2017; vol. 93, pp. 1480-1492.
Kitamura, et al.; "Island Cells Control Temporal Association Memory"; Science; 2014; vol. 343; pp. 896-901.
Kobro-Flatmoen, et al.; "Reelin-immunoreactive Neurons in Entorhinal Cortex Layer II Selectively Express Intracellular Amyloid in Early Alzheimer's Disease"; Neurobiology of Disease; 2016; vol. 93, pp. 172-183.
Kotterman, et al.; "Engineering Adeno-Associated Viruses for Clinical Gene Therapy"; Nature Reviews Genetics; 2014; vol. 15, pp. 445-451.
Kotterman, et al.; "Viral Vectors for Gene Therapy: Translational and Clinical Outlook"; Annual Review of Biomedical Engineering; 2015; vol. 17, pp. 63-89.

Kugler, et al.; "Human Synapsin 1 Gene Promoter Confers Highly Neuron-Specific Long-Term Transgene Expression From an Adenoviral Vector in the Adult Rat Brain Depending on the Transduced Area"; Gene Therapy; 2003; vol. 10, pp. 337-347.
Liu, et al.; "Optogenetic Stimulation of a Hippocampal Engram Activates Fear Memory Recall"; Nature; 2012; vol. 184, pp. 381-385.
Loew, et al.; "Improved Tet-Responsive Promoters With Minimized Background Expression"; BMC Biotechnology; 2010; vol. 10, Issue 81, pp. 1-13.
Luo, et al.; "Long Noncoding RNAs and Alzheimer's Disease"; Clinical Interventions on Aging; 2016; vol. 11, pp. 867-872.
Luo, et al.; "Subthalamic GAD Gene Therapy in a Parkinson's Disease Rat Model"; Science; 2002; vol. 298, pp. 425-429.
Mendell, et al.; "Single-Dose Gene-Replacement Therapy for Spinal Muscular Atrophy"; New England Journal of Medicine; 2017; vol. 377, Issue 18; pp. 1713-1722.
Miao, et al.; "Parvalbumin and Somatostatin Interneurons Control Different Space-Coding Networks in the Medial Entorhinal Cortex"; Cell; 2017; vol. 171, pp. 507-521.
Murphy, et al.; "Alzheimer's Disease and the B-Amyloid Peptide"; Journal of Alzheimer's Disease; 2010; vol. 19, Issue 1; pp. 1-17.
Nair, et al.; "Enhanced" Viral Vectors: Driving Transgene Expression Limited to Specific Neuronal Cell Types in Wildtype Animals Using Enhancers Identified by Differential Screening of Brain Regions; Abstract WW7; Neuroscience; Nov. 15, 2017; 1 page.
Nair, et al.; Poster; "Viruses Made with Entorhinal Cortex-Specific (EC) Enhancers Enable Transgene Expression Restricted to Particular EC Celltypes in Two Species of Wildtype Animals"; FENS 2018, Jul. 2018; Berlin, Germany; 1 page.
O'Brien, et al.; "Amyloid Precursor Protein Processing and Alzheimer's Disease"; Annual Review of Neuroscience 2011; vol. 34, pp. 185-204.
Pennacchio, et al.; "Predicting Tissue-Specific Enhancers in the Human Genome"; Genome Research; 2007; vol. 17, pp. 201-211.
Potter, et al.; "A Simplified Purification Protocol for Recombinant Adeno-Associated Virus Vectors"; Molecular Therapy—Methods & Clinical Development; 2014; vol. 1; 14034; pp. 1-7.
Roadmap Epigenomics Consortium; "Integrative Analysis of 111 Reference Human Epigenomes"; 2015 Nature; vol. 518, pp. 317-330.
Rosenzweig; "Vectors for Gene Therapy"; Current Protocols in Human Genetics; 2007; Chapter 12; pp. 1-4.
Roth, et al.; "DREADDs for Neuroscientists"; Neuron; 2016; vol. 89, pp. 683-694.
Rowland, et al.; "Transgenically Targeted Rabies Virus Demonstrates a Major Monosynaptic Projection from Hippocampal Area CA2 to Medial Entorhinal Layer II Neurons"; Journal of Neuroscience; 2013; vol. 33, Issue 37; pp. 14889-14898.
Shen, et al.; "A Map of the cis-Regulatory Sequences in the Mouse Genome"; Nature; 2012; vol. 488, pp. 116-120.
Shevtsova, et al.; "Promoters and Serotypes: Targeting of Adeno-Associated Virus Vectors for Gene Transfer in the Rat Central Nervous System in Vitro and in Vivo"; Experimental Physiology; 2004; vol. 90, Issue 1; pp. 53-59.
Sternson, et al.; "Chemogenetic Tools to Interrogate Brain Functions"; Annual Review of Neuroscience; 2014; vol. 33, No. 37; pp. 387-406.
Varga, et al.; "Target-Selective GABAergic Control of Entorhinal Cortex Output"; Nature Neuroscience; 2010; vol. 13; Issue 7, pp. 822-824.

A. MEC-13-48E

B. MEC-13-53A

C. MEC-13-81B

D. MEC-13-104B

E. MEC-13-79A

F. MEC-13-95H

G. MEC-13-32B

H. MEC-13-123B

A. FOUNDER A

E. FOUNDER E

B. FOUNDER B

F. FOUNDER F

C. FOUNDER C

G. FOUNDER G

D. FOUNDER D

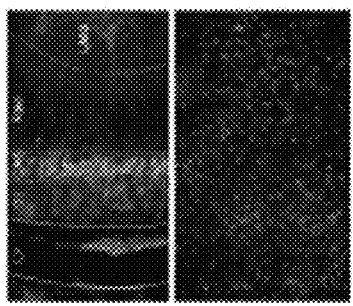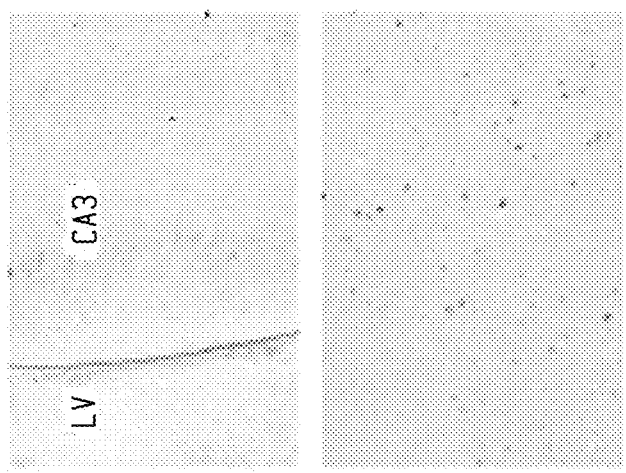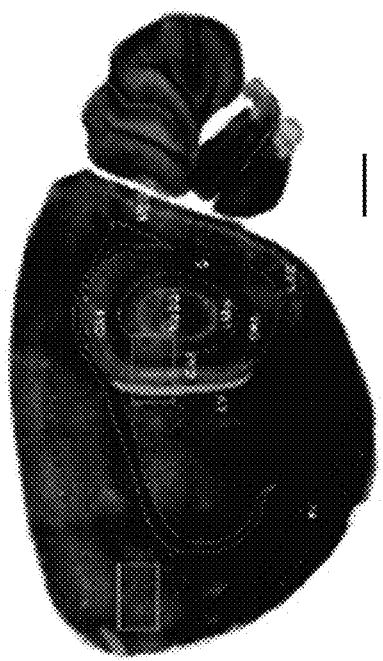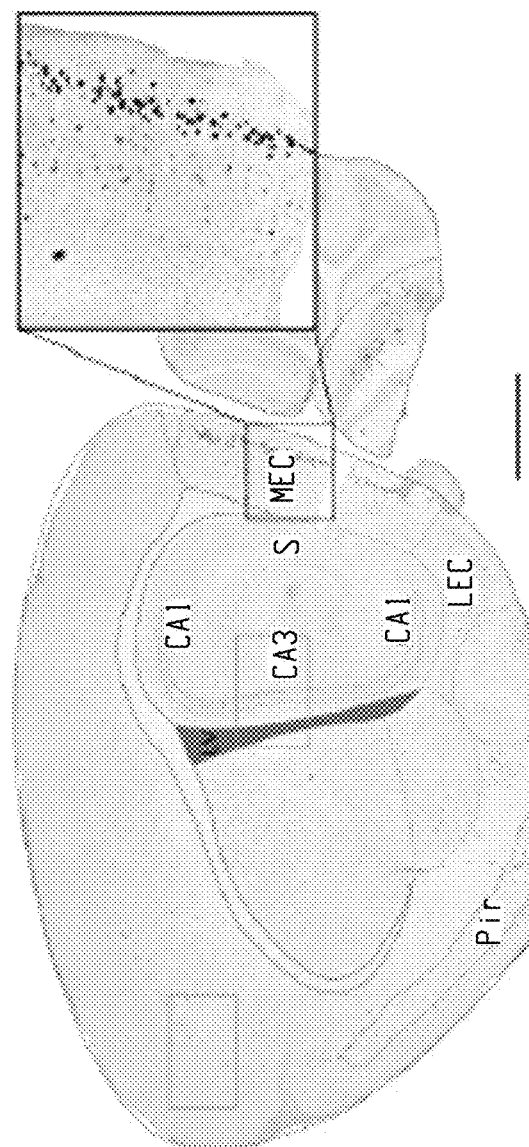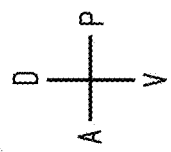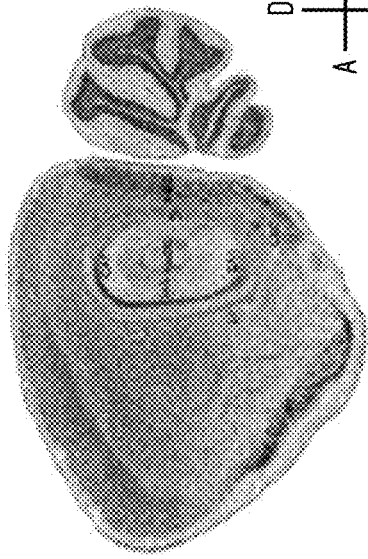
Fig. 5B
Fig. 5C
Fig. 5D

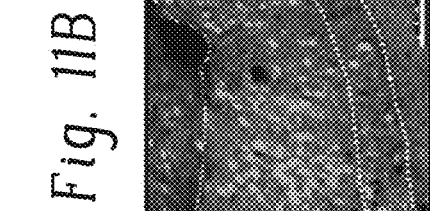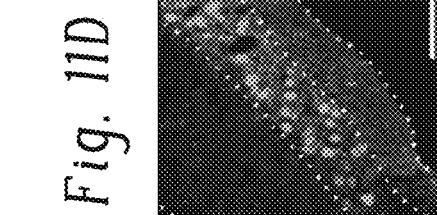
Fig. 11A  Fig. 11B
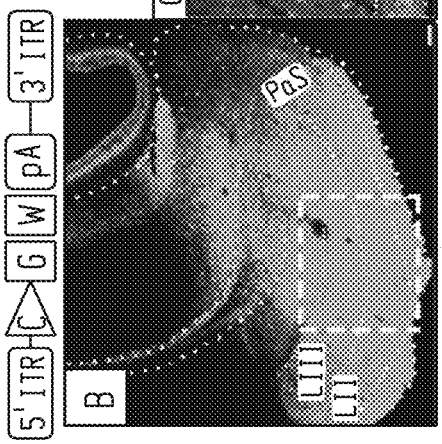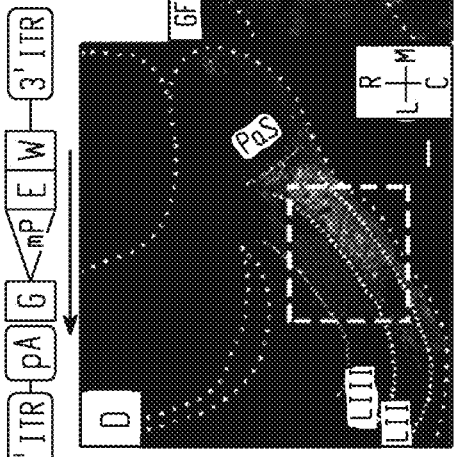
Fig. 11C  Fig. 11D
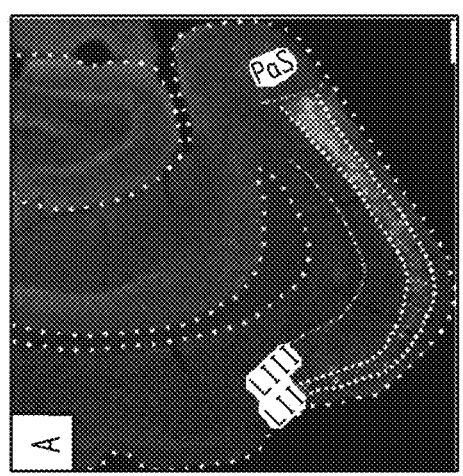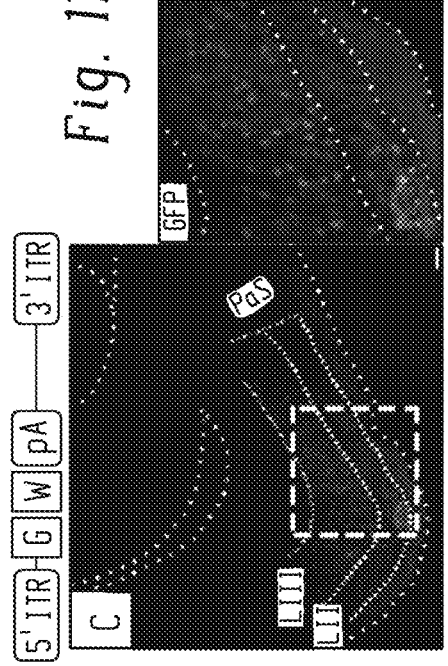
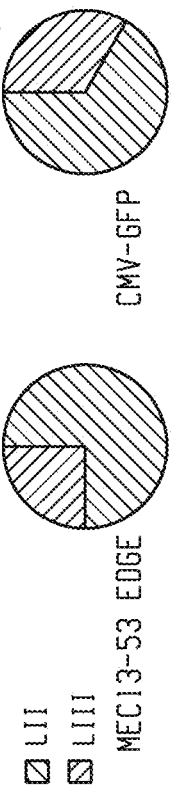
Fig. 11E

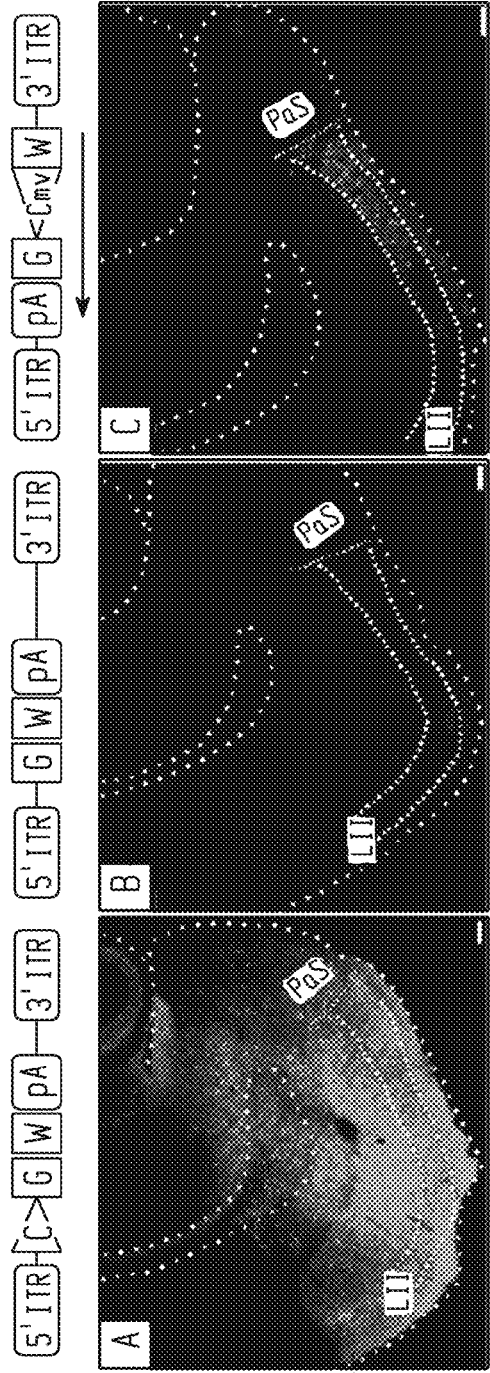
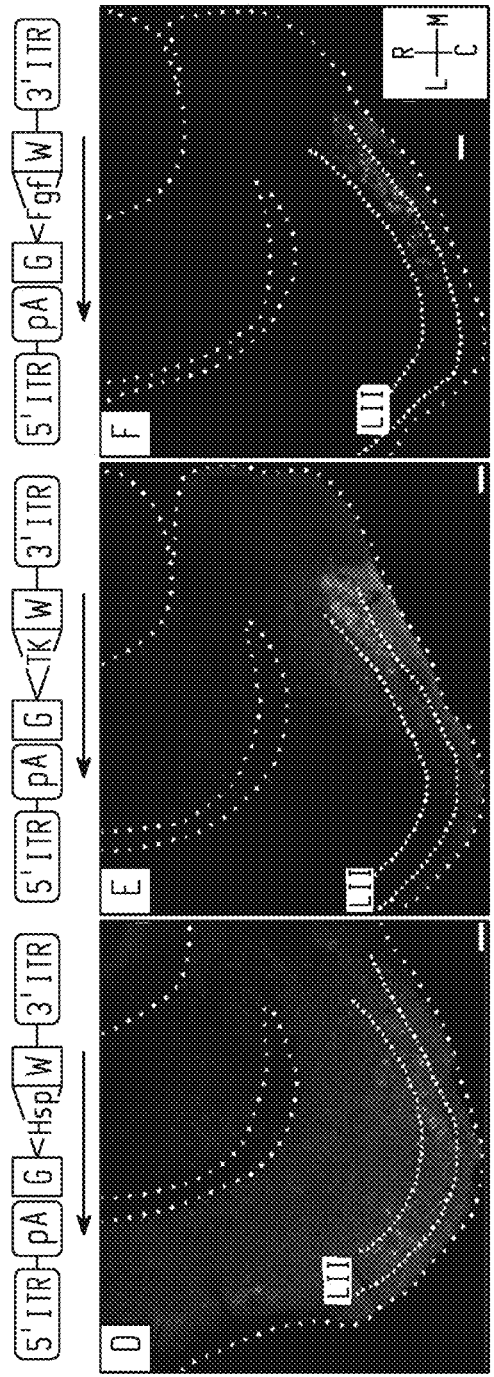
Fig. 12A  Fig. 12B  Fig. 12C
Fig. 12D  Fig. 12E  Fig. 12F

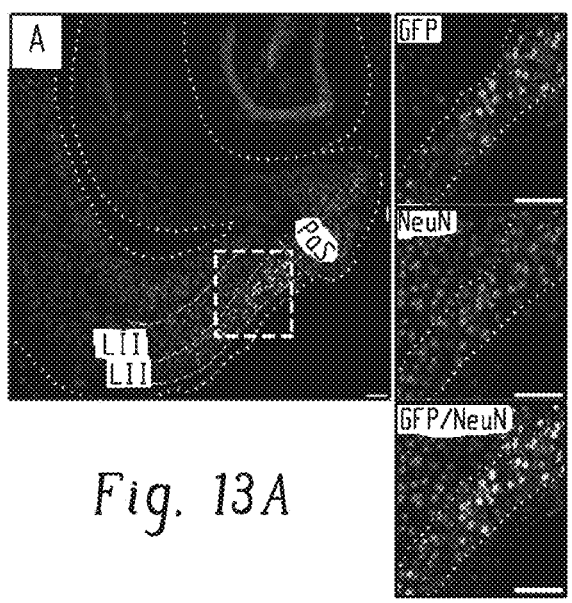 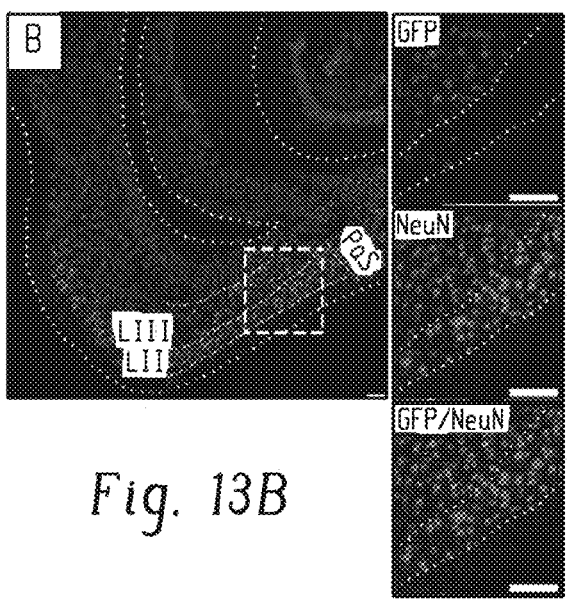
Fig. 13A  Fig. 13B
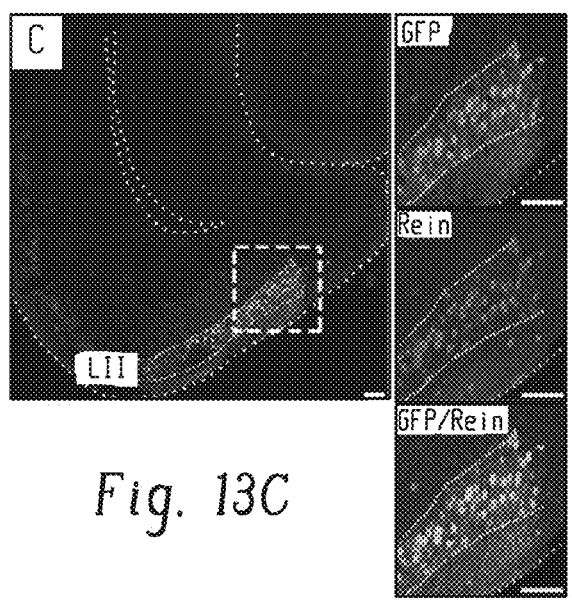 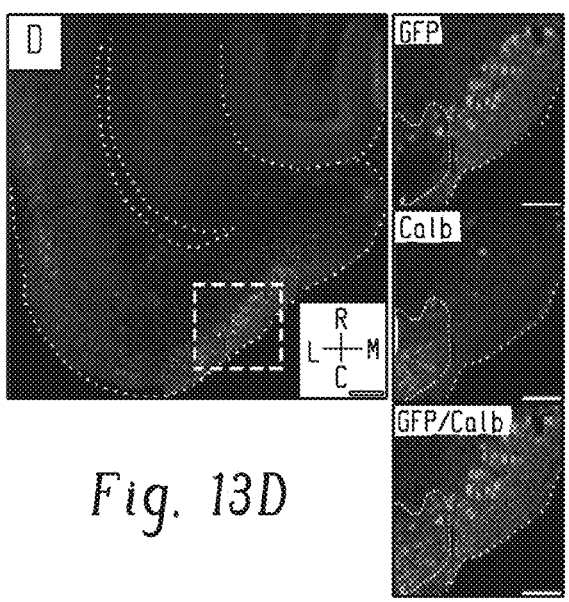
Fig. 13C  Fig. 13D
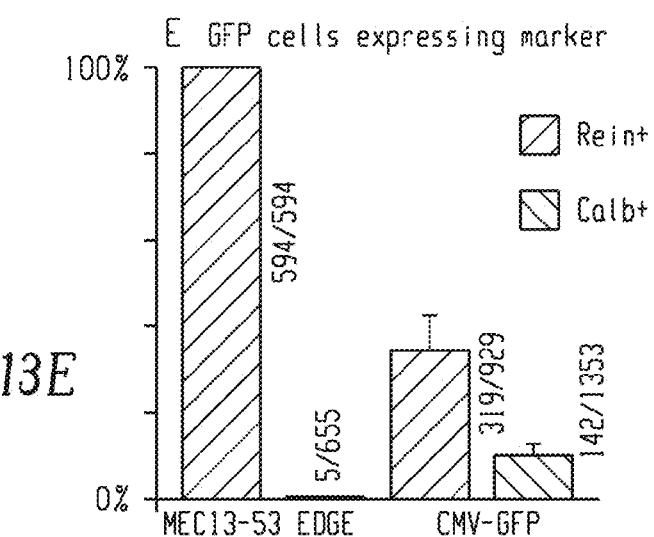
Fig. 13E

NEURONAL ENHANCERS

CROSS-REFERENCE TO RELATED APPLICATIONS

This application claims priority to U.S. Provisional Application Ser. No. 62/584,282 filed on Nov. 10, 2017, which is incorporated herein by reference in its entirety.

SEQUENCE LISTING

The Sequence listing filed as ASCII text file DN8689665 created on Oct. 30, 2018 and having a size of 5,823,203 bytes by EFS is incorporated by reference in its entirety.

FIELD OF THE DISCLOSURE

The present disclosure is in the field of gene therapy, and provides delivery vehicles which may be used in the treatment of neurological disorders, in particular Alzheimer's disease. To this end, the disclosure provides both the aforementioned delivery vehicles and methods of treatment using the delivery vehicles.

BACKGROUND

The mammalian brain is arguably the most complex biological structure known, composed of around $10^{11}$ neurons in humans. There is currently no definitive method for classifying different types of neurons, but depending on the criteria used (e.g., morphology, connectivity, gene expression and/or receptive field type) the number may be astronomical. Neuron classification is complicated by the fact that most genes are broadly expressed in the adult brain (i.e., in many different cell types) and so there are relatively few individual marker genes (indeed there are far more different cell types than there are marker genes).

Enhancer sequences which are active in specific sub-regions of the brain can be used to drive sub-region-specific or neuron-type-specific gene expression. Enhancer sequences specifically active in a number of brain regions have been identified, including the entorhinal cortex (EC). Enhancers which specifically drive gene expression in the EC may be used in gene therapy for neurological conditions which affect this region of the brain. Such conditions include, most notably, Alzheimer's disease (AD).

AD is a neurodegenerative disease which causes the majority of cases of dementia. Symptoms include disorientation, mood swings and behavioral difficulties, in addition to the characteristic memory loss. AD is progressive and invariably fatal, though death does not occur for many years after diagnosis. AD occurs predominantly in the elderly (only approximately 5% of cases are diagnosed before the age of 65), and due to increased life expectancy and the aging nature of Western society, is becoming ever more common. Not only is AD a terrible disease causing great suffering to those afflicted, and to their loved ones, it is also a significant economic burden on society, due to the requirement for continuous care for those with more advanced disease.

At present, the causes of AD are poorly understood, and though links between AD development and head injuries, depression and hypertension have been identified, the primary cause is believed to be genetic. Moreover, to date no preventative or curative therapies have been identified, despite the urgent need for such.

Brains of AD sufferers are characterized by the extracellular and intracellular build-up of aggregates of the proteins amyloid-β and tau, and a neuropathology of brain atrophy, the loss of both neurons and synapses, inflammation and cerebral amyloid angiopathy (the formation of amyloid deposits on the walls of blood vessels within the brain). Amyloid-β is generated by cleavage of the amyloid precursor protein (APP), a neuronal transmembrane protein. In healthy brains, APP appears beneficial for neuron growth and survival (O'Brien & Wong, Annu. Rev. Neurosci. Vol. 34, pp. 185-204, 2011), but in the AD brain, cleavage of APP by the β-secretase and γ-secretase generates the approximately 40 amino acid fragment known as amyloid-β (Chow et al., Neuromolecular Med. Vol. 12(1), pp. 1-12, 2010). Amyloid-β forms aggregates known as amyloid plaques. Amyloid-β appears to play a central role in AD development, though how this occurs is not entirely clear, and many hypotheses have been put forward, including the generation of reactive oxygen species which may depolarise the synaptic membrane, physical disruption of the neuronal membrane by amyloid plaques, and the disruption of calcium ion homeostasis by soluble oligomers of amyloid-β.

Tau forms insoluble aggregates following hyperphosphorylation. These aggregates are known as neurofibrillary tangles and are considered a primary marker of AD.

It is believed that the build-up of amyloid plaques and deposits in the brain causes AD (Murphy & Levine, J. Alzheimers Dis. Vol. 19(1), p. 311, 2010) but how this occurs is by no means clear. The role of neurofibrillary tangles in AD is controversial, but they may constitute an important causative factor of the disease.

It had been hoped that antibody therapy against amyloid-β would be curative for AD, but while such therapy has been found to be successful in clearing the characteristic amyloid-β plaques from the brains of AD patients, no improvement or delay in dementia has yet been seen to result (Holmes et al., Lancet Vol. 372, pp. 216-223, 2008). It may be that the dementia associated with AD, particularly in the late stages of the disease, is irreversible. To successfully treat AD it is therefore important to intervene early, and preferably to prevent the development of symptomatic disease in the first place. Early stage or preventative treatment requires therapy targeted to the brain regions where the disease begins.

AD is known to begin in the entorhinal cortex. The entorhinal cortex is located in the medial temporal lobe, and via its interactions with the hippocampus plays an essential role in memory and navigation (hence these functions are lost first in AD sufferers). AD spreads across the brain transynaptically from the entorhinal cortex to affect other regions, leading to later stage symptoms and eventually death. The entorhinal cortex comprises six layers. Layers I and IV are molecular layers, being relatively free of neurons. AD initiates in Layer II, the outermost layer of cells in the EC. Many EC Layer II cells express the protein Reelin, a regulator of neuronal migration and positioning in the developing brain. AD initiates in Reelin-positive neurons in EC Layer II (Kobro-Flatmoen et al., Neurobiol. Dis. Vol. 93, pp. 172-183, 2016), for instance pre-alpha cells.

What is needed are new compositions and methods for the treatment of Alzheimer's disease.

US 2015/0044187 discloses enhancers which drive forebrain-specific gene expression during embryonic brain development. The document teaches the use of such enhancers to generate neurons from stem cells.

SUMMARY

In a first aspect, provided herein is a delivery vehicle comprising a nucleic acid construct, wherein the nucleic acid construct comprises:
  (i) an enhancer which specifically drives gene expression in cells of the entorhinal cortex;
  (ii) a promoter; and
  (iii) a therapeutic gene,
wherein said enhancer, promoter and therapeutic gene are operatively linked, said enhancer and therapeutic gene are heterologous, and said delivery vehicle is suitable for delivery of the nucleic acid construct to the brain of a mammal.

In a particular embodiment the delivery vehicle is a viral vector.

In another aspect, a cell comprises the nucleic acid construct as defined above.

In another aspect, a composition comprises a delivery vehicle as described above and at least one physiologically-acceptable diluent, carrier or excipient.

In another aspect, a method of treating or preventing Alzheimer's disease comprises administering a delivery vehicle or a composition described above to a subject in need thereof.

In another aspect, a method of driving entorhinal cortex-specific gene expression in a mammalian subject comprises administering to said subject a delivery vehicle or a composition as described above.

BRIEF DESCRIPTION OF DRAWINGS

The patent or application file contains at least one drawing executed in color. Copies of this patent or patent application publication with color drawing(s) will be provided by the Office upon request and payment of the necessary fee.

FIG. 1A shows pie charts showing the proportions (and numbers) of distinct active genomic elements identified by H3K27ac ChIP-seq of the 4 cortical sub-regions. These numbers are roughly similar to those found by ChIP-seq of other organs.

FIG. 1B shows dendrogram (left) and correlation matrix of the H3K27ac signals (right) from replicates of the cortical sub-regions dissected in this experiment versus those from ENCODE, which were used for subtraction (all tissue data except for that in relation to the MEC, LEC, RSC and ACC is from ENCODE). Note the high correlation of replicates and clustering of signal from cortical tissues.

FIG. 1C shows heatmaps showing some of the tissue-specific putative enhancers identified in the microdissected cortical sub-regions.

FIGS. 5A-D collectively show that enhancers of non-specific genes drive region-specific transgene expression.

FIG. 5A specifically shows a genomic view of one of the 165 MEC-specific enhancers identified by ChIP-seq analysis. The specific region of the genome containing the enhancer (MEC-13-104) is blown up in the right-hand panel.

FIG. 5B specifically shows in situ hybridisation (ISH; brain-map.org) of Trpsl, the gene associated with enhancer MEC-13-104 shows expression throughout the cortex (Ctx), striatum (Str) and cerebellum (Cb).

FIG. 5C shows hGFP expression driven by enhancer MEC-13-104 is seen in the MEC as well as some other brain regions.

FIG. 5D specifically shows expression of the chemogenetic activator HM3 driven by MEC-13-104 is seen specifically in the MEC. Scalebars are 1000 µm. Sagittal plane, Dorsal-Ventral and Anterior-Posterior axis are indicated.

Figure 7:
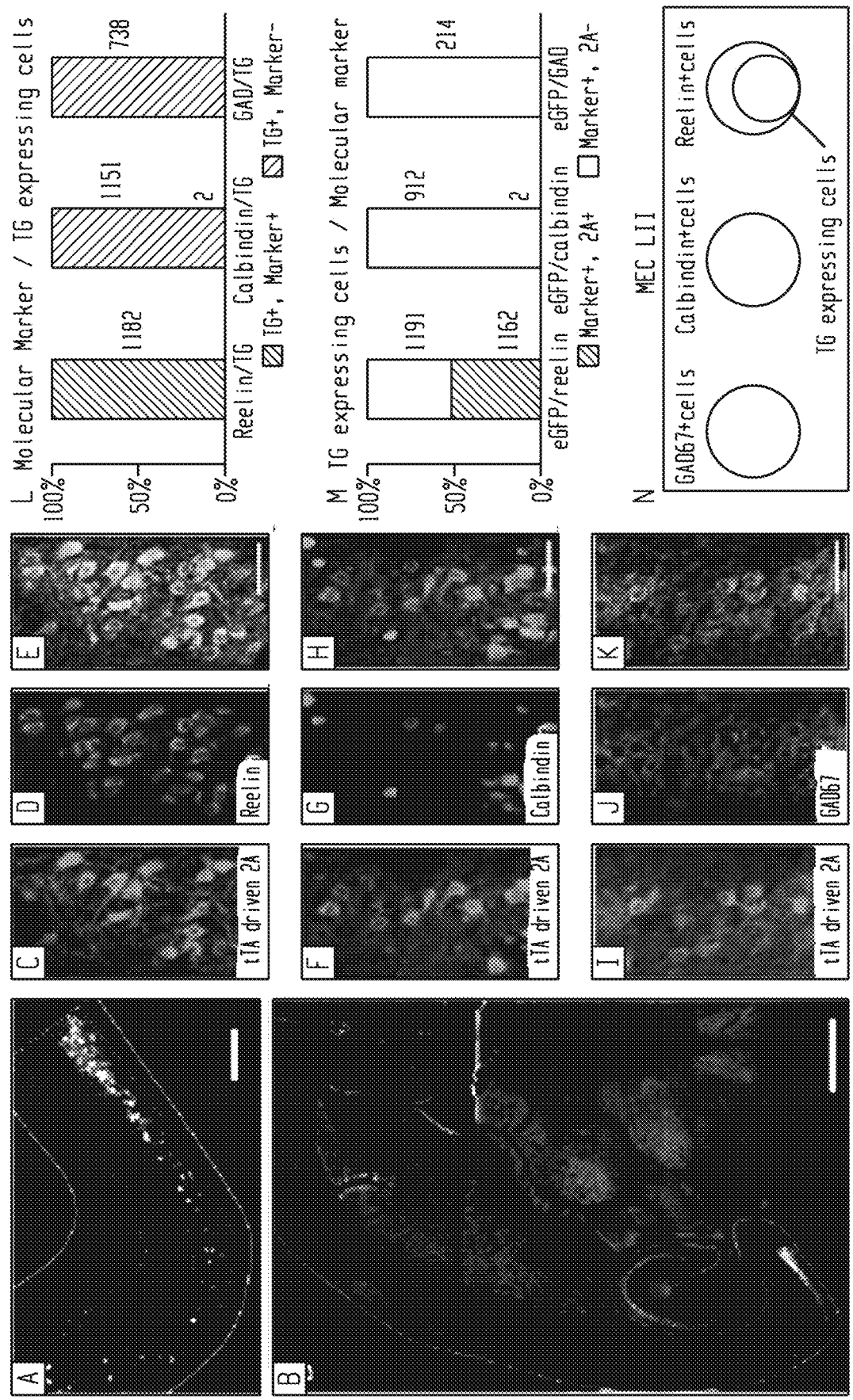
FIG. 7 shows that single enhancers can drive expression in histochemically-defined subsets of MEC Layer II cells.

Panels A and B of FIG. 7 show horizontal sections of a mouse cross between MEC-13-53A and TVAG. Immunohistochemical transgene detection with anti-2A antibody shows layer II EC-specific expression.

Panels C, F, and I of FIG. 7 show anti-2A histochemistry.
Panel D of FIG. 7 shows anti-Reelin histochemistry.
Panel G of FIG. 7 shows anti-Calbindin histochemistry.
Panel J of FIG. 7 shows anti-GAD67 histochemistry.
Panels E, H, and K of FIG. 7 show overlays of the two signals; each row is the same section.

Panel L of FIG. 7 shows 100% of transgenic cells co-localize with Reelin but there is essentially 0% with calbindin and GAD67 (TG=transgene).

Panel M of FIG. 7 shows 50% of all Reelin-positive cells were positive for the transgene, essentially none of the other cell populations had any transgene expressing cells. Total numbers of cells counted in white.

Panel N of FIG. 7 shows achematic summary of the data in FIGS. 7C to M.

Scale bars in FIG. 7 are 1000 µm in panel B, 200 µm in panel A and 50 µm in panels E, H and K. In all graphs bars show the mean+SEM.

Figure 8:
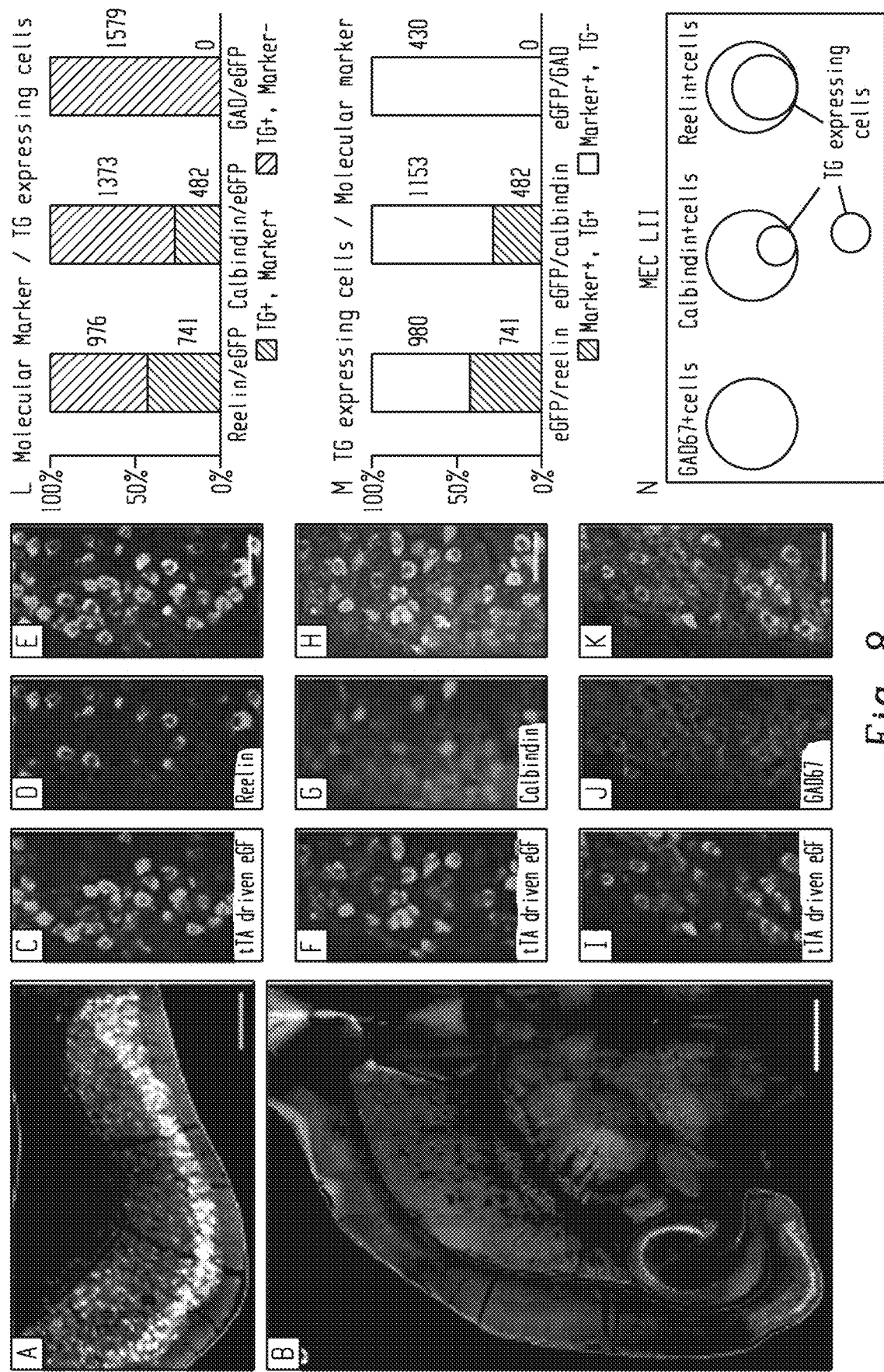

FIG. 8 shows that different single enhancers can drive expression in histochemically-distinct subsets of MEC Layer II cells.

Panels A and B of FIG. 8 show horizontal section of a mouse cross between MEC-13-104B and tetO-eGFP. Immunohistochemical transgene detection with anti-GFP Ab shows EC-specific expression.

Panels C, F, I of FIG. 8 show anti-GFP histochemistry.
Panel D of FIG. 8 shows anti-Reelin histochemistry.
Panel G of FIG. 8 shows anti-Calbindin histochemistry.
Panel 8J of FIG. 8 shows anti-GAD67 histochemistry.
Panels 8E, 8H, 8K of FIG. 8 show overlays of the two signals, each row is the same section.

Panel L of FIG. 8 shows 42.9% of transgenic cells in layer II of the EC co-localise with reelin while 26% of them co-localise with calbindin. 0% co-localise with GAD67.

Panel M of FIG. 8 shows 42.7% of all reelin-positive cells in layer II of the EC were positive for the transgene and 30% of all calbindin-positive cells in layer II of the EC were positive for the transgene, while 0% of the GAD67 positive population had any transgene expressing cells. Total numbers of cells counted in white.

Panel N of FIG. 8 shows a schematic summary of the data in panels C to M.

Scale bars in FIG. 8 are 1000 μm in panel B, 200 μm in panel A and 50 μm in panels E, H and K. In all graphs bars show the mean+SEM.

Figure 9:
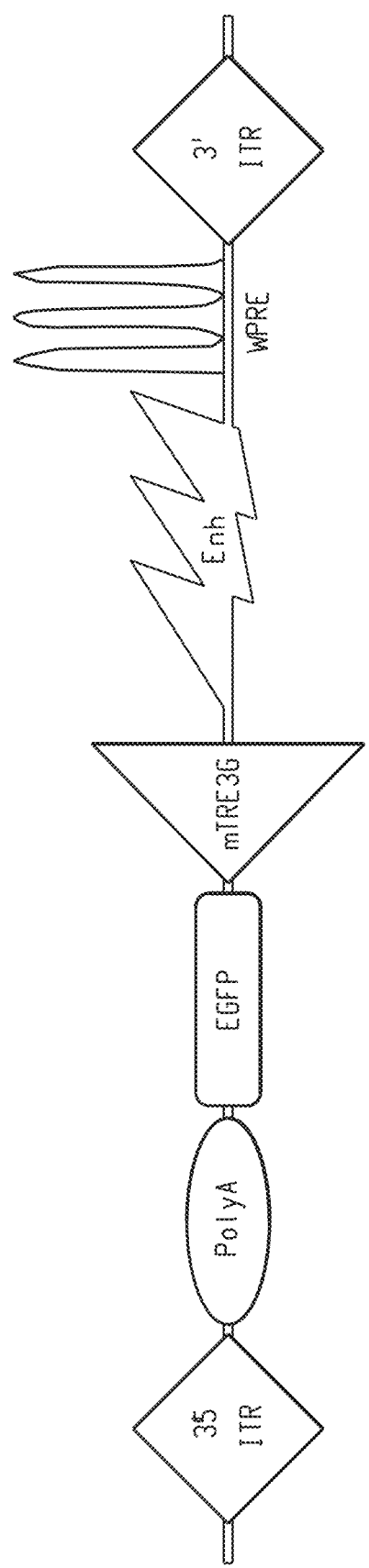

FIG. 9 is a schematic diagram of the AAV DNA construct used to specifically drive eGFP expression in at MEC. The orientation of the construct is inverted relative to the orientation of the DNA strand.

FIGS. 10A-E collectively show EC-specific expression of eGFP in a rat injected with a construct as shown in FIG. 9. The scale bars all=100 μm.

Figure 10A:
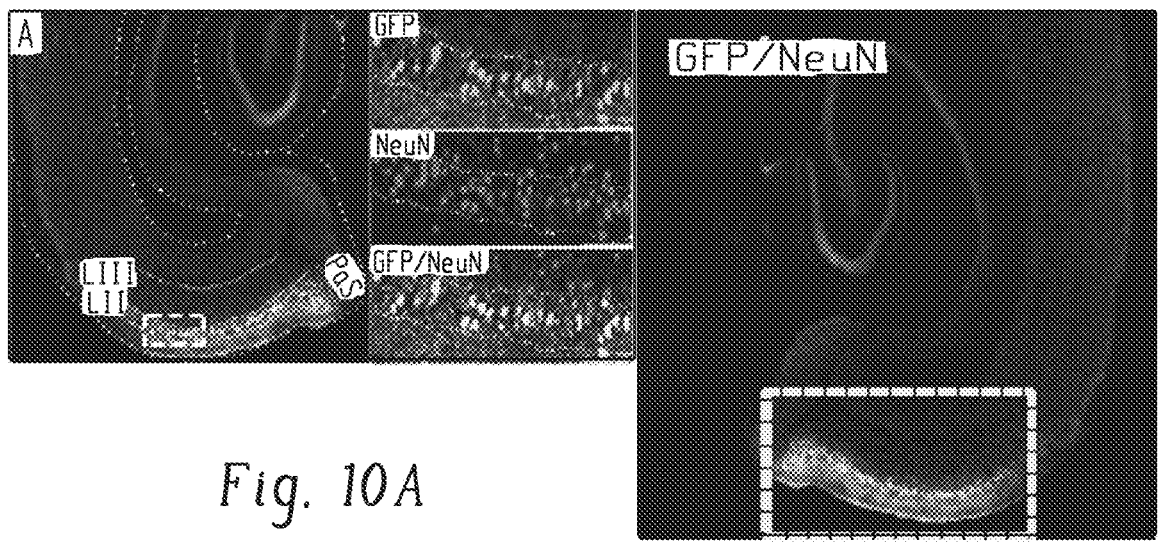

FIG. 10A shows brain section of a rat injected with an AAV carrying an experimental construct containing the MEC-13-53 enhancer. NeuN is a neuronal biomarker. eGFP expression is seen only in the MEC. Insets show GFP staining (top), NeuN staining (middle) and an overlay (bottom) of the box in the left panel.

Figure 10B:
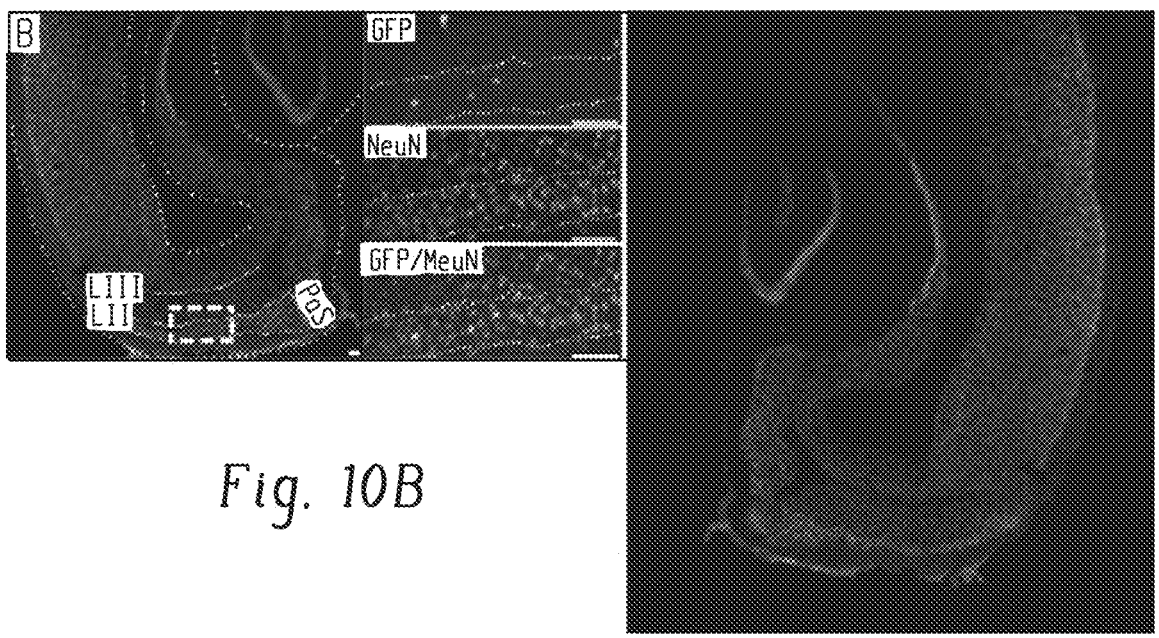

FIG. 10B shows brain section of a rat injected with an AAV carrying a control construct containing no enhancer. No eGFP expression was seen. Insets show same as in 10A.

Figure 10C:
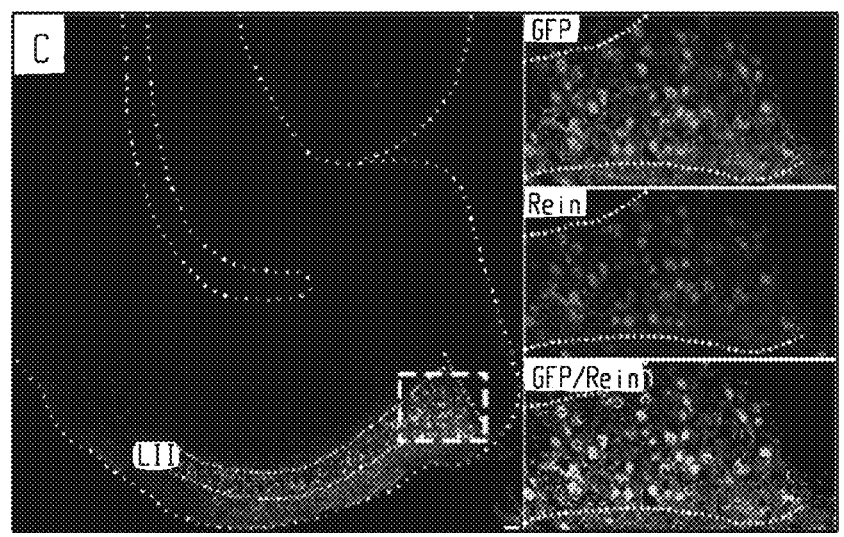

FIG. 10C shows brain section of rat corresponding to that of 10A, except counter-stained with anti-reelin antibody instead of anti-NeuN antibody. As shown, the reelin stain extensively co-localises with the GFP.

Figure 10D:
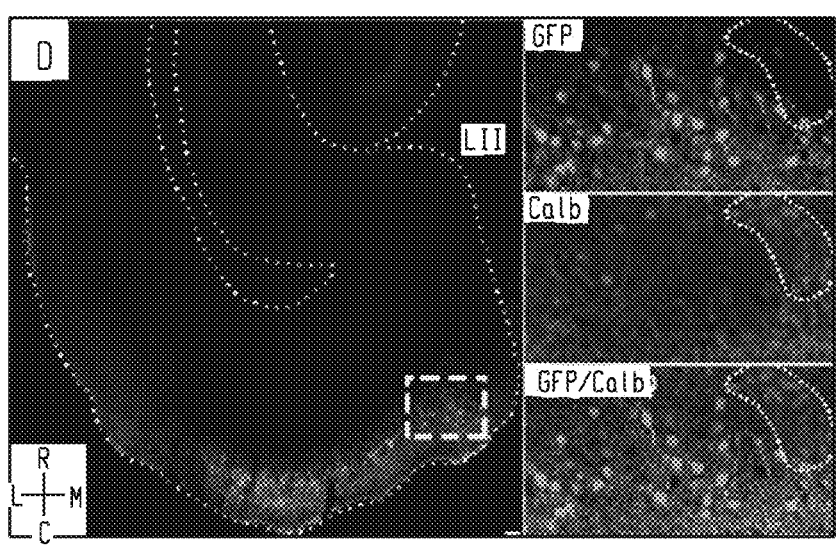

FIG. 10D shows brain section of rat corresponding to that of 10A, except counter-stained with anti-calbindin antibody instead of anti-NeuN antibody. A CB+ cell cluster is outlined in the insets. Co-localisation of CB and GFP is not seen.

Figure 10E:
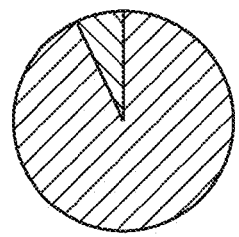

FIG. 10E shows the proportion of MEC-13-53 EDGE expressing cells in MEC layers II and III.

Figure 10F:
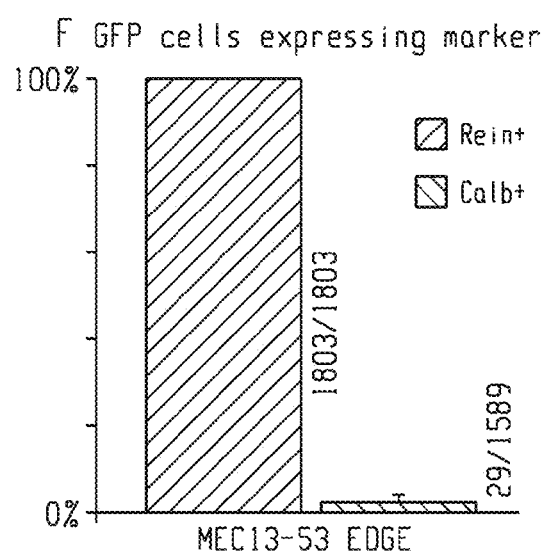

FIG. 10F shows a summary of results, showing the proportion of cells counted co-expressing GFP and the cell marker reelin (left) or calbindin (right).

FIGS. 11A-E collectively show the optimisation of viral EDGE-rAAV constructs for expression in mice. The genetic structure of the pAAV-transgene construct is shown above each of parts B-D: "C" indicates the CMV promoter, "G" indicates the eGFP gene, "W" indicates the WPRE, "pA" indicates a polyA sequence, "E" indicates an enhancer (specifically MEC-13-53) and "mp" indicates a minimal promoter (specifically the TRE3G minimal promoter). In each of A-D the scale bar=100 μm.

FIG. 11A shows expression of the TVAG transgene driven by enhancer MEC-13-53 in a transgenic cross, as visualised by anti-2A immunostaining, is restricted to reelin-positive LII projection neurons in the EC.

FIG. 11B: shows injection of a non-specific (CMV-GFP) virus into the EC shows broad labelling of the entire region.

GFP expression is under the control of the full CMV promoter (SEQ ID NO: 1673).

FIG. 11C shows the same construct without a minimal promoter shows weak nonspecific expression throughout the region.

FIG. 11D shows changing the orientation of the expression cassette relative to the viral ITRs leads to a marked reduction in non-specific expression of MEC-13-53 EDGE rAAV. For the purposes of comparison, panels B-D are of the same volume of virus injected using the same coordinates and visualised using exactly the same settings. The images in (B) and (D) are overexposed to the same settings as (C) in order to visualize the background expression in (C). FIGS. 12 A-C show the same images at settings sufficiently low to avoid overexposure of the CMV-GFP virus.

FIG. 11E shows the proportion of GFP-expressing cells in layer II and III of the MEC, comparing expression by MEC-13-53 EDGE and a non-specific virus.

FIGS. 12A-F also collectively show the optimization of viral EDGE-rAAV constructs for expression in mice. Again, the genetic structure of the pAAV-transgene construct is shown above each part of the figure. The figure shows that MEC-13-53 EDGE-rAAV exhibited essentially identical layer-II specific EDGE in combination with multiple minimal promoters. In each of A-F the scale bar=100 μm.

FIGS. 12A-C, s detailed above in the legend to FIG. 11, show expression from the same constructs as FIGS. 11B-D, respectively, but are not overexposed. At these settings one cannot detect any expression from the virus lacking a promoter virus (12B).

FIGS. 12D-F show: Expression is shown using the same construct organisation as that of 12C, except that rather than the TRE3G minimal promoter expression is driven from the HSP68 minimal promoter (12D), TK minimal promoter (12E) or FGF4 minimal promoter (12F).

FIGS. 13A-E collectively show that MEC13-53 EDGE rAAVs recapitulate the cell-type specificity seen in MEC-13-53 EDGE transgenic crosses in WT mice.

FIG. 13A shows MEC-13-53 EDGE-rAAV was injected into the MEC of WT-mice. Insets show immunostaining of GFP (top) and NeuN (middle); and an overlay of the two (bottom).

FIG. 13B shows an equal volume relative to 13A of TRE3G-rAAV (i.e. virus identical to that used in 13A except without an enhancer) was injected into the MEC of WT-mice. Insets show the same as in 13A.

FIG. 13C shows immunostaining of brain sections of the same mice as 13A, except counterstained with anti-reelin antibody instead of anti-NeuN antibody. As shown, the reelin stain extensively co-localises with the GFP.

FIG. 13D shows immunostaining of brain sections of the same mice as 13A, except counterstained with anti-calbindin (CB) antibody instead of anti-NeuN antibody. A CB+ cell cluster is outlined in the insets. No co-localisation of CB and GFP is seen.

FIG. 13E shows a summary of results: cells co-expressing GFP and marker reelin (left-hand column of each pair) or calbindin (right-hand column of each pair) with number of cells counted.

Figure 14:
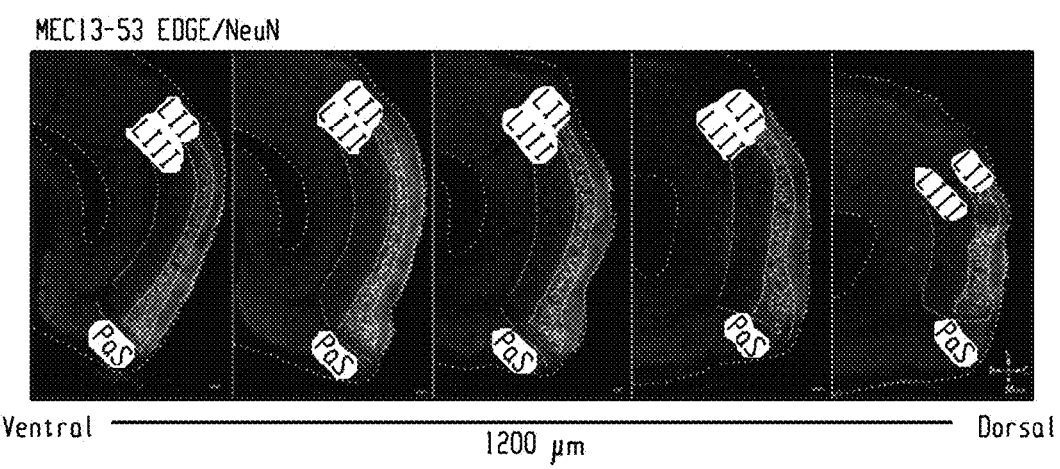

FIG. 14 shows that expression specificity is not limited to the AAV injection site. Representative images of the GFP+ and NeuN+ neurons in multiple horizontal sections in the dorso-ventral axis from a rat brain injected with MEC-13-53-EDGE rAAV. Interestingly the very few GFP+ cells not in EC L-II (e.g. Subiculum) are still Reelin+. MEC-13-53 was shown to drive expression preferentially in MEC-layer II throughout the dorso-ventral axis. Scale bar=100 μm.

FIGS. 15A-D collectively show that other EDGE rAAVs largely recapitulate the regional specificity shown by the relevant enhancers in transgenic mice. In each image the scale bar=100 μm.

Figure 15A:
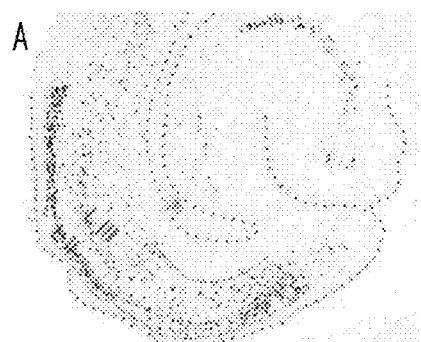

FIG. 15A shows expression of the TVAG transgene driven by the MEC-13-104 enhancer in an EDGE transgenic cross is visualised by ISH using the relevant probe.

Figure 15B:
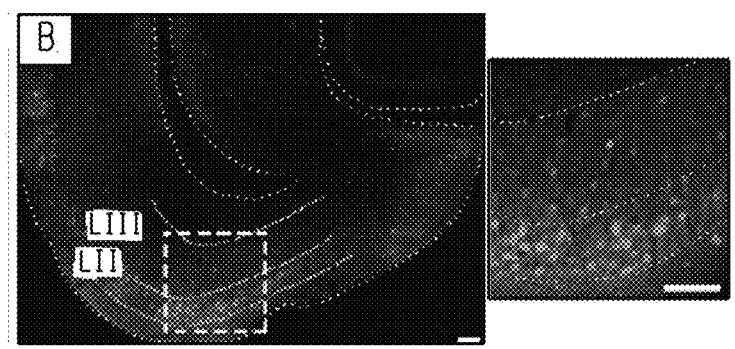

FIG. 15B shows expression of GFP in a wildtype mouse driven by MEC-13-104 in an EDGE-rAAV. As shown, the rAAV recapitulates the expression pattern driven by the enhancer in transgenic mice.

Figure 15C:
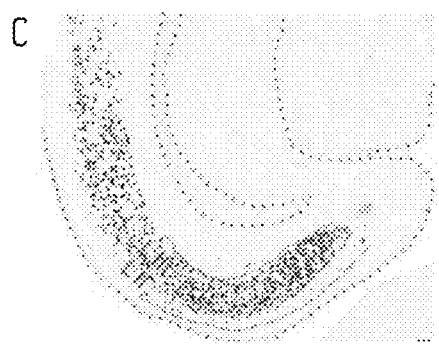

FIG. 15C shows expression of the HM3 transgene driven by the LEC-13-8 enhancer in an EDGE transgenic cross is visualised by ISH using the relevant probe.

Figure 15D:
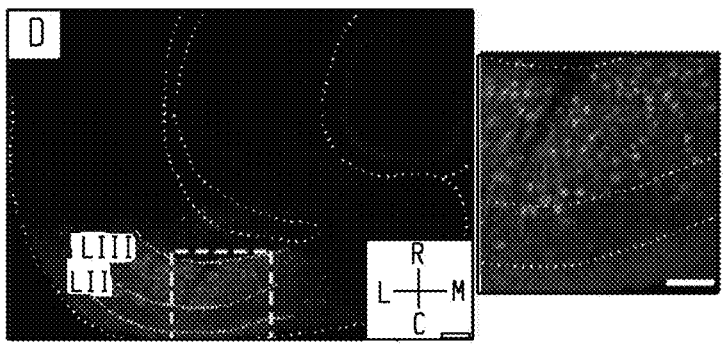

FIG. 15D shows expression of GFP in a wildtype mouse driven by LEC-13-8 in an EDGE-rAAV. As shown, the rAAV recapitulates the expression pattern driven by the enhancer in transgenic mice.

The above-described and other features will be appreciated and understood by those skilled in the art from the following detailed description, drawings, and appended claims.

DETAILED DESCRIPTION

The inventors have discovered that neuron types are characterized not by the expression of specific marker genes, but rather by the expression of distinct sets of genes. The inventors have discovered that the expression of neuron type-specific sets of genes is controlled by enhancers. These regulatory elements are active in distinct brain regions and neuronal cell types, thus determining the gene combinations expressed in each neuron.

The present application discloses enhancer sequences which specifically drive gene expression in the EC, and more particularly in certain sub-sets of EC cells, including even more particularly EC layer II neurons. These enhancer sequences can be used in gene therapy to drive expression of therapeutic genes specifically in EC layer II cells, targeting AD at its source. Use of these enhancer sequences to drive cell-type specific gene expression enables the expression of a therapeutic gene in EC layer II cells, even if the therapeutic gene is toxic if expressed more widely, since by placing the therapeutic gene under the control of an appropriate enhancer expression of the gene is limited to the desired EC layer II neurons. The delivery vehicles described herein comprise nucleic acid constructs in which a therapeutic gene is under the control of a promoter and an enhancer which drives EC-specific gene expression. The delivery vehicles can be used in gene therapy to prevent AD or to treat AD at an early stage before symptoms have appeared, thus arresting its development before brain function is irreparably damaged. The enhancers disclosed herein thus open up a wholly new avenue for AD prevention and treatment.

In the work leading up to this disclosure, the inventors identified large numbers of region and sub-region specific enhancers in the brain, and remarkably have shown that in transgenic mice based on single enhancers specific to a particular brain region (specifically the medial entorhinal cortex (MEC)) the enhancers may drive expression specifically in distinct subsets of MEC neurons. Even more surprisingly, it has now further been shown that such enhancers may be used in expression constructs which when delivered in viral vectors may be used to achieve region-specific or sub-region-specific, or even more particularly cell-type-specific expression in the brains of mice or rats. Such enhancers may thus provide the means to achieve specific gene expression of a desired transgene in a targeted manner, e.g. in a desired brain region or sub-region, or in a particular type or sub-set of cells.

As described above, disclosed herein are delivery vehicles comprising a nucleic acid construct, wherein the delivery vehicle is suitable for delivery of the nucleic acid construct to the brain of a mammal. The delivery vehicle may alternatively be referred to as a vector for gene therapy. In other words it is a nucleic acid-carrying particle which is able to deliver a nucleic acid of interest to a target cell in an organism. In the context of the present disclosure, the delivery vehicle is able to deliver a nucleic acid of interest to target cells in the brain of a mammal. Delivery vehicles (i.e. vectors) for gene therapy are well-known in the art (see e.g. Rosenzweig, A., 2007, Vectors for Gene Therapy, Current Protocols in Human Genetics).

The delivery vehicle is able to deliver a nucleic acid construct to the brain of a mammal. As such, the delivery vehicle is able to cross the blood-brain barrier; such delivery vehicles are known in the art (see e.g. Costa & Pedroso de Lima, *J. Genet Syndr Gene Ther* 2013, Vol. 4(7): 161). Lipid-soluble species are able to cross the blood brain barrier, so in some embodiments the delivery vehicle of the invention may be lipid soluble. In a particular embodiment, the delivery vehicle is able to deliver a nucleic acid construct to the brain of a human, though in other particular embodiments the delivery vehicle may also or alternatively be able to deliver a nucleic acid construct to the brain of a laboratory animal such as a mouse, rat or monkey. Delivery vehicles are further discussed below.

A delivery vehicle comprises a nucleic acid construct comprising:

(i) an enhancer which specifically drives gene expression in cells of the entorhinal cortex;
(ii) a promoter; and
(iii) a therapeutic gene, wherein said enhancer, promoter and therapeutic gene are operatively linked.

The nucleic acid construct is a recombinant construct. The nucleic acid construct is a nucleic acid molecule comprising a number of functional nucleotide sequences of interest. The nucleic acid molecule may be a DNA molecule or an RNA molecule, and may include chemical derivatives of DNA or RNA, including molecules having a radioactive isotope or a chemical adduct such as a fluorophore, chromophore or biotin ("label"). Thus the nucleic acid may comprise modified nucleotides. Said modifications include base modifications such as bromouridine, ribose modifications such as arabinoside and 2',3'-dideoxyribose and internucleotide linkage modifications such as phosphorothioate, phosphorodithioate, phosphoroselenoate, phosphorodiselenoate, phosphoroanilothioate, phoshoraniladate and phosphoroamidate. The term "nucleic acid molecule" specifically includes single and double stranded forms of both DNA and RNA.

As noted the nucleic acid construct disclosed herein comprises a therapeutic gene. When the nucleic acid construct is a single-stranded DNA molecule, it may be a sense strand or antisense strand. When the nucleic acid construct is an RNA molecule, it may be a positive-sense or negative-sense nucleic acid strand. In the case that the nucleic acid construct is an RNA molecule, the construct is such that the therapeutic gene cannot be translated without the construct first being reverse transcribed into DNA, to enable transcription of the therapeutic gene to be regulated by the operatively-linked enhancer.

The nucleic acid construct disclosed herein comprises an enhancer which specifically drives gene expression in cells of the entorhinal cortex. An enhancer sequence, as commonly known in the art, is a nucleotide sequence which regulates expression of a gene. The binding of specific transcription factors to enhancer sequences leads to the recruitment of RNA polymerase II and general transcription factors to the gene promoter, by the direct interaction of the specific transcription factors with the RNA polymerase and general transcription factors. Enhancer sequences may be identified by any method known in the art, including traditional methods such as enhancer trap, and state of the art methods including DNase-Seq, FAIRE-Seq, DNA sequence analysis to identify transcription factor binding sites (which are associated with enhancer sequences) or computational genomics to identify sequence conservation of non-coding regions (which can be indicative of enhancers). Many enhancer sequences are already known in the art and are available from databases, for instance the ENCODE Encyclopaedia which contains over 1 million putative human enhancer sequences and over 500,000 putative murine enhancer sequences. The enhancer in the nucleic acid construct may be derived from any species, in particular it may be derived from a mammal. Alternatively, the enhancer may be a synthetic sequence, for instance it may be specifically defined for the purpose of this disclosure.

An enhancer which drives gene expression of cells in the entorhinal cortex may also be referred to as an enhancer which is active in cells of the entorhinal cortex. An enhancer active in cells of the entorhinal cortex may be identified by any method known in the art, e.g. by ChIP-seq, or by analogy to a known entorhinal cortex-specific enhancer of a different species. ChIP-seq may be used to identify active enhancer sequences based on histone modifications. Modification, e.g. methylation or acetylation, of histone proteins is associated with activation or repression of the associated DNA sequence. For instance, histone modification at the location of a gene or promoter sequence may activate or repress transcription of the gene or from the promoter. Histone modification at the location of an enhancer may activate or suppress enhancer activity and thus transcription of the gene regulated by the enhancer.

Specific modifications of particular residues within histone proteins are associated with either activation or repression of the associated DNA sequence. Enhancer sequences which are associated with histones containing activatory modifications may be considered as active. Activatory histone modifications are well-known in the art and include acetylation of lysine 27 on histone H3 and methylation of lysine 4 on histone H3. Acetylated histone H3 lysine 27 is referred to as H3K27ac. Methylation of lysine 4 of H3 may be single methylation (H3K4me), dimethylation (H3K4me2) or trimethylation (H3K4me3). Enhancer sequences which are active in the entorhinal cortex may be identified by performing ChIP-seq on chromatin isolated from cells from the entorhinal cortex of a mammal. Entorhinal cortex cells may be isolated by microdissection of the brain of a mammal. Enhancer sequences which are associated with activatory histone modifications, e.g. histones containing the H3K27ac and/or H3K4me2 modifications, in entorhinal cortex tissue are enhancers which are active in cells of the entorhinal cortex.

As detailed above, the entorhinal cortex is located in the medial temporal lobe of the brain. It approximately corresponds to Brodmann areas 28 and 34. The skilled person is well able to identify the entorhinal cortex in a mammalian brain. As defined herein, the entorhinal cortex includes the transentorhinal cortex. The transentorhinal cortex forms a transition zone between the entorhinal cortex and the isocortex, and contains interdigitation of laminae of both the entorhinal cortex and the isocortex.

In rodents, the entorhinal cortex is considered to comprise two sub-regions: the lateral entorhinal cortex (LEC) and the medial entorhinal cortex (MEC). The LEC and MEC are differentiated by their morphological features, e.g. the shape, size and type of neurons located within them. The LEC and MEC are also differentiated by their input/output connectivity, e.g., the LEC is strongly connected to the perirhinal cortex, olfactory and insular cortex and the amygdala; the MEC is strongly connected to the postrhinal cortex, the presubiculum, visual association (occipital) and retrosplenial cortices. The term "entorhinal cortex" as used herein includes both the MEC and the LEC. It is currently unclear whether the human entorhinal cortex can be considered to comprise sub-regions corresponding to the LEC and the MEC.

As noted above, the nucleic acid construct disclosed herein comprises an enhancer which specifically drives gene expression in cells of the entorhinal cortex. By "specifically drives gene expression in cells of the entorhinal cortex" is meant that the enhancer drives gene expression only, or substantially only or predominantly, in cells of the entorhinal cortex, and thus does not drive gene expression in other cell types, either in other regions of the brain or in non-brain tissues, or only drives such non-entorhinal cortex expression to a minor, insignificant or negligible extent. An enhancer which specifically drives gene expression in cells of the entorhinal cortex (e.g., which is only active in cells of the entorhinal cortex) may be identified by any method known in the art. In particular, such an enhancer may be identified by comparison of enhancer activity in cells of the entorhinal cortex with the activity of the same enhancer in other tissues. For instance, the activity of an enhancer sequence identified as active in cells of the entorhinal cortex may be analysed in cells of other brain regions and other non-brain tissues, for instance in cells of the cerebellum or the immune system. An enhancer which is active in the entorhinal cortex but inactive in all other tested tissue types is an enhancer which specifically drives gene expression in cells of the entorhinal cortex.

The nucleic acid construct disclosed herein also comprises a promoter. As is well known in the art, a promoter is a region of DNA located immediately upstream of a gene, to which RNA polymerase binds and which contains the transcription start site. Eukaryotic promoters commonly include the TATA box for the binding of general transcription factors to the promoter for recruitment of RNA polymerase. Alternatively, the promoter may comprise an initiator motif and a downstream promoter element to fulfil this role. The structure of promoters is well-known in the art, as are the sequences of many promoters. The promoter used is a promoter which is functional in a mammalian cell (by functional is meant a promoter which is able to drive gene expression). In a particular embodiment the promoter used is a promoter which is functional in a human cell. The promoter may be a mammalian promoter, in particular the promoter may be derived from the species to which the delivery vehicle of the invention is intended to deliver the nucleic acid construct. The promoter may be a human promoter. The promoter may be a variant of a mammalian promoter, including a variant of a human promoter, which has been modified for enhanced or tighter gene expression. Alternatively, the promoter may be a non-mammalian promoter which is nonetheless functional in a mammalian cell, such as a promoter from a non-mammalian animal or a promoter from a virus, particularly a virus which is able to infect a mammal, e.g., a virus which is able to infect a human. In another embodiment the promoter is a synthetic promoter or a chimeric promoter containing elements derived from one or more different promoters. The skilled person is well able to identify a promoter which can be used in the current invention.

The nucleic acid construct disclosed herein also comprises a therapeutic gene. "Therapy", as defined herein, refers to the treatment or prevention of any medical condition. A therapeutic gene is a gene which is useful in therapy. In other words, a therapeutic gene is any gene which may be expressed in a cell in order to treat or prevent a medical condition, for instance a disease. The therapeutic gene of the present invention is not limited, and may be any gene useful in therapy. In particular, the therapeutic gene is a gene which may be expressed in cells of the entorhinal cortex in order to treat or prevent a medical condition. The therapeutic gene may be useful in therapy for any medical condition. The therapeutic gene may be from any source, e.g. it may be derived from a mammal, e.g. a human or the mammal to which the delivery vehicle of the invention is intended to deliver the nucleic acid construct; the therapeutic gene may be derived from a non-mammalian animal, a plant, a bacterium or an archaeon; the therapeutic gene may be any gene derived from nature, or a variant of such a gene; the therapeutic gene may be an artificial gene, e.g. a fusion gene. Any gene whose expression is useful in the treatment or prevention of any medical condition may be used in the present invention as a therapeutic gene.

In the nucleic acid construct disclosed herein, the enhancer, promoter and therapeutic gene are operably linked. The term "operably linked" refers to the association of two or more nucleic acid molecules on a single nucleic acid fragment so that the function of one is affected by the 5 other. For example, a promoter is operably linked to a gene when the promoter is capable of affecting the expression of that gene (i.e. the gene is under the transcriptional control of the promoter). Genes may be operably linked to regulatory sequences in sense or antisense orientation.

Accordingly, in the construct of the disclosure, the promoter is operatively linked to the therapeutic gene, meaning that expression of the therapeutic gene is under the control of the promoter. The enhancer and the promoter are operatively linked, meaning that the enhancer initiates binding of RNA polymerase to the promoter and thus regulates the activity of the promoter. The enhancer and the therapeutic gene are operatively linked, meaning that the enhancer drives expression of the therapeutic gene, via the enhancer's interaction with the promoter.

As detailed above, the promoter is located upstream of the therapeutic gene in the nucleic acid construct disclosed herein. The enhancer may be located upstream or downstream of the therapeutic gene. The skilled person is well able to synthesise a construct as disclosed herein, with the therapeutic gene, promoter and enhancer sequences located appropriately to one another in an appropriate order, orientation and spacing. In an embodiment the enhancer is located upstream of the promoter, for instance immediately 5' of the promoter. By immediately 5' is meant that the enhancer is 5' to the promoter and no sequence elements are present between the enhancer and the promoter. Non-functional nucleotides may nonetheless form a spacer between the enhancer and the promoter.

In the present application, a first element is upstream of a second element when the first element is 5' to the second element, and conversely a first element is downstream of a second element when the first element is 3' to the second element. When referring to elements being upstream or downstream of one another in the construct, this is in the context of the construct and its elements being in the forward orientation. If the construct is inverted, i.e. placed in the reverse orientation, upstream and downstream are reversed.

The enhancer and the therapeutic gene in the construct disclosed herein are heterologous. By "heterologous", as used herein, is meant not natively operatively linked, i.e., not operatively linked in nature, e.g., in a wild-type organism. In this instance, the enhancer does not natively drive expression of the therapeutic gene. The enhancer and the therapeutic gene may be derived from different organisms, or they may be derived from the same organism, e.g., the same species of animal, for instance the enhancer and therapeutic gene may each be human. When derived from the same organism, the enhancer and therapeutic gene may be natively located on different chromosomes, but the enhancer and therapeutic gene may be located on the same chromosome. However, the enhancer does not natively drive or affect the expression of the therapeutic gene. The skilled person is well able to identify whether an enhancer natively drives expression of any given gene.

It may be that one or both of the enhancer and the therapeutic gene is a variant of a natural enhancer or gene. By variant is meant that the sequence (e.g. enhancer) is derived from a natural sequence (e.g. a natural enhancer sequence), but is modified relative to the natural enhancer sequence. A variant, as defined herein, may be modified relative to the sequence from which it is derived by substitution, addition or deletion of one or more nucleotides. For the purposes of the present application, a variant enhancer is considered a synthetic enhancer, and a variant therapeutic gene is considered a synthetic gene. Accordingly, a variant enhancer cannot be considered to be homologous to any therapeutic gene, because the variant enhancer is not found in nature. Similarly, a variant therapeutic gene cannot be considered to be homologous to any enhancer, because the variant therapeutic gene is not found in nature.

In the construct disclosed herein, the therapeutic gene is operably linked to an enhancer which specifically drives gene expression in cells of the entorhinal cortex. Preferably, the therapeutic gene is operably linked to only one enhancer, but may be operatively linked to two or more enhancers which specifically drive gene expression in cells of the entorhinal cortex. The therapeutic gene is not operatively linked to any enhancer which is not specifically active in cells of the entorhinal cortex.

The nucleic acid construct disclosed herein may be in any suitable form for delivery to a mammalian brain cell, for instance a plasmid, a cosmid, a phagemid, a viral chromosome (which may be a DNA or RNA viral chromosome) or an artificial chromosome (e.g. a human artificial chromosome). The nucleic acid construct may be linear or circular. The nucleic acid construct may comprise any sequence elements necessary or helpful for synthesis or delivery to a target cell, for instance an antibiotic resistance gene and/or an alternative gene for positive or negative selection of the construct, an origin of replication, a centromere, telomeres, and so forth. The sequence elements necessary are dependent on the nature of the nucleic acid construct, and are well-known to the skilled person. Upon delivery to a target cell in the brain of a mammal, the nucleic acid construct disclosed herein may integrate into the target cell genome (i.e. it may integrate at a defined or undefined location within a chromosome of the target cell), or it may be retained in the target cell extra-chromosomally.

In the construct disclosed herein, the promoter is preferably a "tight" promoter, or alternatively put, the promoter is preferably not "leaky", by which is meant that in the absence of the enhancer no expression of the therapeutic gene is seen. Similarly, no or minimal expression of the therapeutic gene should be seen in cells outside of the entorhinal cortex in a subject to which the delivery vehicle of the invention has been administered. The promoter may be a minimal promoter, by which is meant a core promoter comprising only the minimal required elements for the promoter to drive transcription, and which is inactive in the absence of one or more enhancers. The promoter is preferably not a constitutive promoter.

The promoter in the construct disclosed herein may be homologous to the enhancer, by which is meant that the promoter and enhancer may be natively operatively linked, i.e. operatively linked in a wild-type organism from which they are derived. In the case that the promoter and enhancer are homologous, each is derived from the same organism and drives expression of the same gene in the organism of origin. In another embodiment, the promoter and enhancer are heterologous, i.e. the promoter and the enhancer are not natively operatively linked. When the promoter or enhancer are heterologous, the promoter and enhancer may be derived from different organisms, or the promoter and/or the enhancer may be synthetic. Alternatively, the promoter and the enhancer may both be derived from the same species, but not be operatively linked within the native species, i.e. in the native species the promoter may drive expression of one gene and the enhancer drive expression of a different gene.

As noted above, the enhancer in the nucleic acid construct disclosed herein may be a variant enhancer. Similarly, the promoter in the nucleic acid construct of the invention may be a variant promoter. For the purposes of the present application a variant promoter is considered a synthetic promoter. Accordingly, a variant promoter cannot be considered homologous to an enhancer, as no such promoter is found in nature. Similarly, a variant enhancer cannot be considered to be homologous to a promoter.

The promoter may be homologous to the therapeutic gene or heterologous to the therapeutic gene. If the promoter is a variant promoter it cannot be considered homologous to a therapeutic gene, and if a therapeutic gene is a variant therapeutic gene it cannot be considered homologous to a promoter.

In an embodiment, the promoter is an Hsp68 minimal promoter. The Hsp68 minimal promoter is the promoter which is natively operatively linked to the gene encoding heat shock protein 68. An Hsp68 minimal promoter may be derived from any animal, particularly a mammal, e.g. an Hsp68 promoter may be from a rodent or a primate. The Hsp68 promoter may be a wild-type Hsp68 promoter or a variant of a wild-type Hsp68 promoter. The promoter may be a murine Hsp68 minimal promoter, for example the promoter may be the Hsp68 promoter which has the nucleotide sequence set forth in SEQ ID NO: 1630 or a variant thereof. Thus the promoter may comprise the nucleotide sequence set forth in SEQ ID NO: 1630, or a nucleotide sequence with at least 70, 75, 80, 85, 90 or 95% sequence identity to SEQ ID NO: 1630. Alternatively, the promoter may be a human Hsp68 minimal promoter. The Hsp68 minimal promoter is well known in the art.

In another embodiment, the promoter is the Fgf4 minimal promoter, which is natively operatively linked to the gene encoding fibroblast growth factor 4. The Fgf4 minimal promoter may be obtained from any animal which has such a promoter, including for instance a rodent such as a mouse or a primate such as a human. The Fgf4 promoter may be a wild-type Fgf4 promoter or a variant of a wild-type Fgf4 promoter. In a particular embodiment the Fgf4 promoter is the murine Fgf4 promoter, which has the nucleotide sequence set forth in SEQ ID NO: 1639, or a variant thereof. Thus the promoter may comprise the nucleotide sequence set forth in SEQ ID NO: 1639 or a nucleotide sequence with at least 70, 75, 80, 85, 90 or 95% sequence identity thereto.

In another embodiment, the promoter is the TRE3G promoter. The TRE3G promoter is an artificial promoter designed by ClonTech (USA). The full TRE3G promoter is a tetracycline-regulated Tet-On promoter, which comprises seven 5' tetO sequences (the tetO sequence is set forth in SEQ ID NO: 1640). The promoter may be the full TRE3G promoter, the sequence of which is set forth in SEQ ID NO: 1641, or a variant thereof, i.e. the promoter may comprise the nucleotide sequence set forth in SEQ ID NO: 1641 or a nucleotide sequence with at least 70, 75, 80, 85, 90 or 95% sequence identity thereto. Alternatively the promoter may be the minimal TRE3G promoter, the sequence of which is set forth in SEQ ID NO: 1642, or a variant thereof, i.e. the promoter may comprise the nucleotide sequence set forth in SEQ ID NO: 1642 or a nucleotide sequence with at least 70, 75, 80, 85, 90 or 95% sequence identity thereto. The minimal TRE3G promoter lacks the tetO sequences present in the full-length promoter, but is otherwise identical. The TRE3G minimal promoter is derived from the cytomegalovirus (CMV) promoter.

In another embodiment, the promoter is a TK minimal promoter, which is natively operatively linked to the thymidine kinase gene. The TK minimal promoter may be derived from any organism, for instance it may derived from a eukaryote, such as a mammal, for instance a rodent or a primate, e.g. the TK minimal promoter may be derived from a human or a mouse. Alternatively, the TK minimal promoter may be from a prokaryote or a virus, preferably a virus which is able to infect humans. In a particular embodiment the TK promoter is the herpes simplex virus TK (HSV-TK) promoter, which has the sequence set forth in SEQ ID NO: 1643, or a variant thereof, i.e. the promoter may comprise the nucleotide sequence set forth in SEQ ID NO: 1643 or a nucleotide sequence with at least 70, 75, 80, 85, 90 or 95% sequence identity thereto.

In another embodiment, the promoter is the Odz3 minimal promoter, which is natively operatively linked to the Odz3 gene. In mouse, expression of the Odz3 gene is under control of the enhancer MEC-13-53, the sequence of which is set forth in SEQ ID NO: 2 and which is discussed further below. The Odz3 minimal promoter may be derived from any animal, particularly a mammal such as a rodent, e.g. a mouse, or a primate, e.g. a human. In a particular embodiment the Odz3 minimal promoter is the murine Odz3 minimal promoter which has the nucleotide sequence set forth in SEQ ID NO: 1644, i.e. the promoter may comprise the nucleotide sequence set forth in SEQ ID NO: 1644 or a nucleotide sequence with at least 70, 75, 80, 85, 90 or 95% sequence identity thereto.

As detailed above, the entorhinal cortex comprises six layers, of which Layer II is the outermost layer of cells. In an embodiment, the enhancer which specifically drives gene expression in cells of the entorhinal cortex more specifically drives gene expression only in cells of Layer II of the entorhinal cortex. An enhancer which specifically drives gene expression in cells of Layer II of the entorhinal cortex does not drive gene expression in cells outside of the brain, nor in brain cells located in regions other than the entorhinal cortex, nor in cells of other layers of the entorhinal cortex. Thus an enhancer which specifically drives gene expression in cells of Layer II of the entorhinal cortex does not drive gene expression in cells of any other layer of the entorhinal cortex, e.g. it does not drive gene expression in cells of Layers III, V or VI (as noted above, Layers I and IV are largely free of cells).

Enhancers which specifically drive expression in cells of Layer II of the entorhinal cortex can be identified by ChIP-seq or the like, as described above. Cells of Layer II of the entorhinal cortex may be isolated by microdissection. In rodents for example, Layer II of the entorhinal cortex can be identified based on the presence of characteristic large, spherical neurons.

An enhancer which drives specific expression in cells of Layer II of the EC may be specific to cells of Layer II in a general sense (i.e. layer-specific), or it may, more specifically, drive expression only, or substantially only, in particular sub-sets of cells in Layer II of the EC, for example particular sub-sets defined by the expression of particular neurochemical markers.

As detailed above, many cells in Layer II of the entorhinal cortex express the protein reelin. Reelin is a secreted glycoprotein which forms a part of the extracellular matrix. In addition to its role in the developing brain described above, reelin modulates synaptic plasticity in the adult brain. In an embodiment of the invention, the enhancer which specifically drives gene expression in cells of Layer II of the entorhinal cortex more specifically drives gene expression only in reelin-positive cells of Layer II of the entorhinal cortex (by a reelin-positive cell is meant a cell which expresses reelin). Cells which express reelin may be identified and isolated by any method known in the art, e.g. FACS, and enhancers which specifically drive gene expression in reelin-positive cells of Layer II of the EC may thus be identified by performing ChIP-seq on the isolated cells. Alternatively, enhancers which specifically drive expression in Layer II of the EC may be tested in vivo for their specificity of expression in reelin-positive cells, e.g. by expression of a marker gene such as a fluorescent protein.

The inventors of the present application have identified several hundred enhancers which may specifically drive gene expression in cells of the entorhinal cortex. These enhancers were identified by first microdissecting mouse brains to obtain tissue from the MEC and the LEC, followed by performing ChIP-seq on the isolated tissue. This is described in detail in the Examples. This led to the identification of 165 putative enhancer sequences specifically active in the MEC and 690 putative enhancer sequences specifically active in the LEC. These murine enhancer sequences correspond to SEQ ID NOs: 15-869. To compensate for a possible lack of precise correlation between the ChIP-seq "peaks" and the actual enhancer sequences, the enhancer sequences in SEQ ID NOs: 15-869 are "padded", meaning that 500 nucleotides have been added to both the 5' and 3' ends of the sequences obtained by ChIP-seq, to ensure that the complete enhancer sequence is included in each sequence presented herein.

Accordingly, in an embodiment, the enhancer which specifically drives gene expression in cells of the entorhinal cortex is a murine enhancer sequence, i.e., a sequence derived from the house mouse (Mus musculus), or a variant of a murine enhancer sequence. In a particular embodiment, the enhancer comprises a nucleotide sequence as set forth in any one of SEQ ID NOs: 15-869. Alternatively, the enhancer may comprise a variant of any one of SEQ ID NOs: 15-869, i.e. a nucleotide sequence having at least 70% sequence identity to any one of SEQ ID NOs: 15-869, for instance a nucleotide sequence having at least 75, 80, 85, 90 or 95% sequence identity to any one of SEQ ID NOs: 15-869. A variant of any one of SEQ ID NOs: 15-869 may be obtained by addition, deletion or substitution of one or more nucleotides relative to the unmodified, native sequence.

In light of the padding at both ends of each of SEQ ID NOs: 15-869, in another embodiment, the enhancer which specifically drives gene expression in cells of the entorhinal cortex comprises a fragment of any one of SEQ ID NOs: 15-869, wherein the fragment corresponds to a nucleotide sequence which is obtainable by the deletion of 1 to about 500 nucleotides from the 5' end and/or the deletion of 1 to about 500 nucleotides from the 3' end of any one of SEQ ID NOs: 15-869. A "fragment" of a defined nucleotide sequence, as defined herein, is a segment of the sequence in which the 5' and/or 3' end is truncated relative to the defined nucleotide sequence. The sequence of the fragment is present within the defined nucleotide sequence as a single, contiguous nucleotide sequence.

In another embodiment, the enhancer which specifically drives gene expression in cells of the entorhinal cortex comprises a variant of a fragment of any one of SEQ ID NOs: 15-869, wherein the variant of a fragment has a nucleotide sequence having at least 70, 75, 80, 85, 90 or 95% sequence identity to a fragment of any one of SEQ ID NOs: 15-869, wherein the fragment of any one of SEQ ID NOs: 15-869 is as defined above. Such a variant of a fragment may be obtained by addition, deletion or substitution of one or more nucleotides relative to the unmodified sequence.

A number of the murine enhancer sequences identified by ChIP-seq were tested in mice to identify whether they specifically drive gene expression in cells of the entorhinal cortex. The enhancer sequences identified by ChIP-seq were first filtered according to their H3K27ac signal, conservation across 30 species and the expression of two flanking genes based on visual inspection of in situ hybridisation experiments in mouse brain sections. The filtering process is described in greater detail in the Examples. The putative enhancer sequences were ranked based on the results of the filtering and the highest ranked sequences tested for specific activity in the entorhinal cortex. This was achieved by pronuclear injection into mouse oocytes of constructs comprising a reporter gene and a minimal promoter operatively linked to the enhancer of interest. The resulting mice were killed and their brains analysed for expression of the reporter gene (see Examples for details). This led to the identification of 8 murine enhancer sequences which specifically drove gene expression in the entorhinal cortex. The sequences of these 8 enhancers are set forth in SEQ ID NOs: 1-6, 9 and 10. The chromosomal locations of these enhancer sequences, their associated (i.e. operatively linked) gene(s) and their identifiers are set forth in Table 1.

Accordingly, in an embodiment, the enhancer comprises a nucleotide sequence as set forth in any one of SEQ ID NOs: 1-6, 9 and 10. Alternatively, the enhancer may comprise a variant of a nucleotide sequence as set forth in any one of SEQ ID NOs: 1-6, 9 and 10, i.e. a nucleotide sequence with at least 70% sequence identity to any one of SEQ ID NOs: 1-6, 9 and 10, for instance a nucleotide sequence having at least 75, 80, 85, 90 or 95% sequence identity to any one of SEQ ID NOs: 1-6, 9 and 10. A variant of any one of SEQ ID NOs: 1-6, 9 and 10 may be obtained by addition, deletion or substitution of one or more nucleotides relative to the unmodified, native sequence.

TABLE 1

| SEQ ID NO: | Identifier | Chromosomal Location* | Associated Gene(s) |
|---|---|---|---|
| 1 | MEC-13-32 | chr7: 65,916,198-65,918,580 | UBE3A; ATP10A |
| 2 | MEC-13-53 | chr8: 49,906,388-49,908,569 | ODZ3 |
| 3 | MEC-13-81 | chr10: 99,573,051-99,574,981 | KITL; GM4301 |
| 4 | MEC-13-95 | chr6: 138,334,728-138,335,952 | LMO3; MGST1 |
| 5 | MEC-13-104 | chr15: 50,913,896-50,916,356 | TRPS1; EIF3H |
| 6 | MEC-13-123 | chr16: 39,750,789-39,753,454 | IGSF11 |
| 9 | LEC-13-8 | chr2: 171,158,079-171,159,156 | DOK5; CBLN4 |
| 10 | LEC-13-108 | chr5: 118,194,653-118,195,333 | NOS1; KSR2 |

*chrx indicates chromosome number, e.g. chr7 indicates a location on chromosome 7. The chromosomal coordinates provided pertain to the mm9 mouse reference genome.

The enhancer sequences of SEQ ID NOs: 1-3 and 5 were found to drive MEC-localised gene expression with a particularly high level of specificity, and the enhancer sequences of SEQ ID NOs: 9 and 10 were found to drive LEC-localised gene expression with a particularly high level of specificity. Thus in a particular embodiment the enhancer comprises a nucleotide sequence as set forth in any one of SEQ ID NOs: 1-3, 5, 9 and 10. Alternatively, the enhancer may comprise a variant of a nucleotide sequence as set forth in any one of SEQ ID NOs: 1-3, 5, 9 and 10, i.e. a nucleotide sequence with at least 70% sequence identity to any one of SEQ ID NOs: 1-3, 5, 9 and 10.

The putative murine enhancer sequences set forth in SEQ ID NOs: 7-8 and 11-14 were also tested for their specificity in driving gene expression in the brains of mice. Accordingly, in an embodiment the enhancer comprises a nucleotide sequence as set forth in any one of SEQ ID NOs: 7-8 and 11-14, or a nucleotide sequence with at least 70, 75, 80, 85, 90 or 95% sequence identity to any one of the aforementioned sequences.

Where the enhancer comprises a variant or fragment of a native murine sequence as defined herein, the variant or fragment is an active variant or fragment of the native enhancer sequence. By an active variant or fragment is meant a variant or fragment of the native sequence which specifically drives gene expression in cells of the entorhinal cortex. Preferably, the variant or fragment has enhanced activity relative to the native enhancer sequence, e.g. it may drive a higher level of gene expression in cells of the entorhinal cortex, while retaining its specificity of activity such that it does not drive gene expression in cells outside of the entorhinal cortex.

Human enhancer sequences corresponding to the murine enhancer sequences identified by ChIP-seq were identified based on homology using the UCSC liftover tool (available at https://genome.ucsc.edu/cgi-bin/hgLiftOver). In total, 732 human orthologues of the putative murine enhancer sequences were identified. Human orthologues were not identified for all murine enhancer sequences, but orthologues of all the murine enhancers demonstrated to be active as predicted (and listed in Table 1) were identified. The nucleotide sequences of the 732 putative orthologous human enhancer sequences are set forth in SEQ ID NOs: 898-1629. As for SEQ ID NOs: 15-869, these sequences include padding of 500 nucleotides at the 5' and 3' ends.

Thus, in an embodiment of the invention, the enhancer which specifically drives gene expression in cells of the entorhinal cortex is a human enhancer sequence, i.e. a sequence derived from a human (*Homo sapiens*), or a variant of a human enhancer sequence.

In a particular embodiment, the enhancer which specifically drives gene expression in cells of the entorhinal cortex comprises a nucleotide sequence as set forth in any one of SEQ ID NOs: 898-1629. Alternatively the enhancer may comprise a variant of any one of SEQ ID NOs: 898-1629, i.e., a nucleotide sequence having at least 70, 75, 80, 85, 90 or 95% sequence identity to any one of SEQ ID NOs: 898-1629. A variant of any one of SEQ ID NOs: 898-1629 may be obtained by addition, deletion or substitution of one or more nucleotides relative to the unmodified, native sequence.

In light of the padding at both ends of each of SEQ ID NOs: 898-1629, in another embodiment the enhancer which specifically drives gene expression in cells of the entorhinal cortex comprises a fragment of any one of SEQ ID NOs: 898-1629, wherein the fragment corresponds to a nucleotide sequence which is obtainable by the deletion of 1 to about 500 nucleotides from the 5' end and/or the deletion of 1 to about 500 nucleotides from the 3' end of any one of SEQ ID NOs: 898-1629.

In another embodiment, the enhancer which specifically drives gene expression in cells of the entorhinal cortex comprises a variant of a fragment of any one of SEQ ID NOs: 898-1629, wherein the variant of a fragment has a nucleotide sequence having at least 70, 75, 80, 85, 90 or 95% sequence identity to a fragment of any one of SEQ ID NOs: 898-1629, wherein the fragment of any one of SEQ ID NOs: 898-1629 is as defined above. Such a variant of a fragment may be obtained by addition, deletion or substitution of one or more nucleotides relative to the unmodified sequence.

The human orthologues of the 8 murine enhancer sequences shown to specifically drove gene expression in the entorhinal cortex (i.e. those listed in Table 1) were identified. These are listed below in Table 2. Both the minimal predicted human enhancer sequences are listed as are padded versions. As shown, the minimal predicted human enhancer sequences which correspond to the murine sequences set forth in SEQ ID NOs: 1-6, 9 and 10, are set forth in SEQ ID NOs: 870, 872, 874, 876, 878, 880, 886 and 888, respectively. The padded versions of these predicted human enhancer sequences are set forth in SEQ ID NOs: 871, 873, 875, 877, 879, 881, 887 and 889, respectively. Accordingly, in a particular embodiment the enhancer comprises a nucleotide sequence as set forth in any one of SEQ ID NOs: 870-881 and 886-889. Alternatively, the enhancer may comprise a variant of any one of SEQ ID NOs: 870-881 and 886-889, i.e. a nucleotide sequence having at least 70, 75, 80, 85, 90 or 95% sequence identity to any one of SEQ ID NOs: 870-881 and 886-889. A variant of any one of SEQ ID NOs: 870-881 and 886-889 may be obtained by addition, deletion or substitution of one or more nucleotides relative to the unmodified, native sequence.

TABLE 2

| Murine Sequence | | Orthologous Human Sequence (Minimal) | | Orthologous Human Sequence (Padded) | |
|---|---|---|---|---|---|
| SEQ ID NO: | Identifier | SEQ ID NO: | Chromosomal Location* | SEQ ID NO: | Chromosomal Location |
| 1 | MEC-13-32 | 870 | chr15: 26,104,718-26,106,759 | 871 | chr15: 26,104,218-26,107,259 |
| 2 | MEC-13-53 | 872 | chr4: 183,086,572-183,090,124 | 873 | chr4: 183,086,072-183,090,624 |
| 3 | MEC-13-81 | 874 | chr12: 88,864,752-88,866,740 | 875 | chr12: 88,864,252-88,867,240 |
| 4 | MEC-13-95 | 876 | chr12: 16,723,983-16,725,337 | 877 | chr12: 16,723,483-16,725,837 |
| 5 | MEC-13-104 | 878 | chr8: 116,889,103-116,891,663 | 879 | chr8: 116,888,603-116,892,163 |
| 6 | MEC-13-123 | 880 | chr3: 117,925,034-117,927,714 | 881 | chr3: 117,924,534-117,928,214 |
| 9 | LEC-13-8 | 886 | chr20: 53,829,293-53,830,248 | 887 | chr20: 53,828,793-53,830,748 |
| 10 | LEC-13-108 | 888 | chr12: 117,924,865-117,925,650 | 889 | chr12: 117,924,365-117,926,150 |

*The chromosomal coordinates provided pertain to the hg19 human reference genome.

In light of the padding at both ends of each of SEQ ID NOs: 871, 873, 875, 877, 879, 881, 887 and 889, in another embodiment the enhancer which specifically drives gene expression in cells of the entorhinal cortex comprises a fragment of any one of SEQ ID NOs: 871, 873, 875, 877, 879, 881, 887 and 889, wherein the fragment corresponds to a nucleotide sequence which is obtainable by the deletion of 1 to about 500 nucleotides from the 5' end and/or the deletion of 1 to about 500 nucleotides from the 3' end of any one of SEQ ID NOs: 871, 873, 875, 877, 879, 881, 887 and 889. In another embodiment, the enhancer which specifically drives gene expression in cells of the entorhinal cortex comprises a variant of a fragment of any one of SEQ ID NOs: 871, 873, 875, 877, 879, 881, 887 and 889, wherein the variant of a fragment has a nucleotide sequence having at least 70, 75, 80, 85, 90 or 95% sequence identity to a fragment of any one of SEQ ID NOs: 871, 873, 875, 877, 879, 881, 887 and 889, wherein the fragment of any one of SEQ ID NOs: 871, 873, 875, 877, 879, 881, 887 and 889 is as defined above. Such a variant of a fragment may be obtained by addition, deletion or substitution of one or more nucleotides relative to the unmodified sequence.

In the various embodiments described above which comprise a fragment of a padded sequence, the fragment may correspond to a nucleotide which is obtainable by the deletion of from 1 to any integer up to 500 nucleotides from the 5' end and/or the 3' end of the padded sequence (i.e., of any one of SEQ ID NOs: 15-869, 898-1629, or 871, 873, 875, 877, 879, 881, 887 or 889). Thus, for example 1 to 10, 20, 30, 40, 50, 100, 200, 300, or 400 nucleotides may be deleted from either the 5' end or the 3' end, or both, of any of the aforesaid padded sequences.

The human orthologues of the murine enhancer sequences with the nucleotide sequences set forth in SEQ ID NOs: 7-8 and 11-14 were also identified. The human orthologues of the nucleotide sequences set forth in SEQ ID NOs: 7-8 and 11-14 are set forth in SEQ ID NOs: 882, 884, 890, 892, 894 and 896, respectively. The padded versions of these sequences are set forth in SEQ ID NOs: 883, 885, 891, 893, 895 and 897, respectively. Accordingly, in an embodiment the enhancer which specifically drives gene expression in cells of the entorhinal cortex comprises a nucleotide sequence as set forth in any one of SEQ ID NOs: 882-885 and 890-897. Alternatively, the enhancer may comprise a variant of any one of SEQ ID NOs: 882-885 and 890-897, i.e. a nucleotide sequence having at least 70, 75, 80, 85, 90 or 95% sequence identity to any one of SEQ ID NOs: 882-885 and 890-897. A variant of any one of SEQ ID NOs: 870-881 and 886-889 may be obtained by addition, deletion or substitution of one or more nucleotides relative to the unmodified, native sequence.

In light of the padding at both ends of each of SEQ ID NOs: 883, 885, 891, 893, 895 and 897, in another embodiment the enhancer which specifically drives gene expression in cells of the entorhinal cortex comprises a fragment of any one of SEQ ID NOs: 883, 885, 891, 893, 895 and 897, wherein the fragment corresponds to a nucleotide sequence which is obtainable by the deletion of 1 to about 500 nucleotides from the 5' end and/or the deletion of 1 to about 500 nucleotides from the 3' end of any one of SEQ ID NOs: 883, 885, 891, 893, 895 and 897. In another embodiment, the enhancer which specifically drives gene expression in cells of the entorhinal cortex comprises a variant of a fragment of any one of SEQ ID NOs: 883, 885, 891, 893, 895 and 897, wherein the variant of a fragment has a nucleotide sequence having at least 70, 75, 80, 85, 90 or 95% sequence identity to a fragment of any one of SEQ ID NOs: 883, 885, 891, 893, 895 and 897, wherein the fragment of any one of SEQ ID NOs: 883, 885, 891, 893, 895 and 897 is as defined above. Such a variant of a fragment may be obtained by addition, deletion or substitution of one or more nucleotides relative to the unmodified sequence.

The nucleic acid construct disclosed herein comprises a therapeutic gene. Such a gene is useful in therapy for a medical condition. Preferably it is useful for therapy of a medical condition in a human. Advantageously, it is useful for therapy of a condition which affects cells of the entorhinal cortex. By "useful in therapy for a medical condition" is meant that expression of the gene is able to treat or prevent the medical condition, due to the effect of the gene on the cell or tissue in which it is expressed. Treatment as defined herein may be curative (or intended to be curative) or palliative (i.e., designed merely to limit, relieve or improve the symptoms of a condition). Any positive or beneficial effect, or any improvement in any clinical or functional parameter of the subject of the therapy is included.

The therapeutic gene encodes a functional therapeutic agent. The functional therapeutic agent may be a functional RNA molecule or it may be a protein (i.e., the therapeutic gene may encode a functional RNA molecule or a protein). For instance, the therapeutic agent may be an RNA molecule which interferes with expression of a native protein, e.g., by RNAi. For instance, the RNA molecule may be a short hairpin RNA (shRNA) or a microRNA (miRNA). An shRNA is a short RNA molecule (typically about 80 bases long) which contains a tight hairpin, which is processed within a cell to yield a short interfering RNA (siRNA) which is functional in RNAi to knock down expression of a target protein. The RNA molecule may comprise a sequence which is the reverse complement of a target RNA, e.g. a target mRNA. In other words, the RNA molecule may be an antisense RNA complementary to a target RNA. The skilled person is well able to design an RNA molecule for use in RNAi. In another embodiment the therapeutic agent may be a long non-coding RNA (lncRNA) which has a therapeutic effect. A long non-coding RNA is generally defined as a non-coding RNA at least 200 nucleotides in length. Alternatively the therapeutic agent may be a protein with a function useful in treating or preventing a disease. A protein may have a therapeutic effect by any means.

In a particular embodiment, the therapeutic gene is a gene which is useful in the treatment or prevention of Alzheimer's disease. Such a gene may prevent Alzheimer's disease from occurring in a patient, it may cure Alzheimer's disease, slow disease progression or alleviate certain symptoms of the disease. The therapeutic gene may encode a functional RNA which knocks down expression of genes associated with Alzheimer's disease. The gene associated with Alzheimer's disease may encode a protein, e.g., the APP (specifically amyloid-β) and/or Tau, or a kinase which phosphorylates Tau or stimulates amyloid-β production, e.g., glycogen synthase kinase 3 (GSK-3). Alternatively, the gene associated with Alzheimer's disease may encode a functional RNA, in particular an lncRNA. A number of lncRNAs have been implicated in Alzheimer's disease including the BACE1-AS lncRNA, the 51A lncRNA, the 17A lncRNA, the NDM29 lncRNA and the BC200 lncRNA (lncRNAs implicated in Alzheimer's disease are discussed in Luo & Chen, *Clin. Interv. Aging* 11: 867-872, 2016). In another embodiment, the therapeutic gene encodes a protein which has a therapeutic effect against Alzheimer's disease. For instance, the therapeutic gene may encode a protein which degrades amyloid-β or neurofibrillary tangles comprising Tau. In a particular embodiment, the therapeutic gene encodes neprilysin, which is a zinc-dependent metalloprotease which is able to degrade amyloid-β.

Neprilysin cleaves natriuretic peptides and angiotensin II, which can lead to hypertension and heart failure (neprilysin inhibitors are used in treatment for these conditions). Thus expression of neprilysin must be carefully regulated. Expression of neprilysin which is limited to cells of the entorhinal cortex allows exploitation of the anti-Alzheimer's disease effect of neprilysin (i.e. amyloid-β cleavage) without risking causing heart failure in a patient. Human neprilysin has the UniProt accession number P08473; its amino acid sequence is set forth in SEQ ID NO: 1632. Thus the therapeutic gene may comprise a nucleotide sequence which encodes the amino acid sequence set forth in SEQ ID NO: 1632, or a functional variant of such an amino acid sequence. A functional variant of neprilysin has a modified amino acid sequence but retains its ability to cleave amyloid-β. Preferably, a functional variant has at least 50% of the specific activity of the native sequence in terms of cleavage of amyloid-β. More preferably, a functional variant of neprilysin has at least 60, 70, 80, 90, 100, 110 or 120% or more of the specific activity of the native sequence in terms of cleavage of amyloid-β.

In another embodiment, the therapeutic gene encodes an α-secretase. α-secretases are proteases which cleave the APP within the fragment which forms amyloid-β, and thus prevent amyloid-β generation. α-secretases are members of the ADAM family, which is a family of transmembrane metalloproteases. The therapeutic gene may in particular encode an α-secretase selected from ADAM9, ADAM10, ADAM17 and ADAM19. Human ADAM9 has the UniProt accession number Q13443 and the amino acid sequence set forth in SEQ ID NO: 1633; human ADAM10 has the UniProt accession number O14672 and the amino acid sequence set forth in SEQ ID NO: 1634; ADAM17 has the UniProt accession number P78536 and the amino acid sequence set forth in SEQ ID NO: 1635; ADAM19 has the UniProt accession number Q9H013 and the amino acid sequence set forth in SEQ ID NO: 1636.

Accordingly, in an embodiment the therapeutic gene comprises a nucleotide sequence which encodes an amino acid sequence as set forth in any one of SEQ ID NOs: 1633-1636, or a functional variant of such an amino acid sequence. As above, a functional variant of any one of SEQ ID NOs: 1633-1636 has an amino acid sequence which is modified relative to one of SEQ ID NOs: 1633-1636 but which retains at least 50%, preferably at least 60, 70, 80, 90, 100, 110 or 120% or more of the specific activity of the native enzyme sequence.

In another embodiment the therapeutic gene encodes PGC-1α (i.e., peroxisome proliferator-activated receptor gamma coactivator 1-α). PGC-1α is the master regulator of mitochondrial biogenesis. Expression of PGC-1α in the entorhinal cortex may reduce oxidative stress and inflammation in this region of the brain, which it is believed may prevent or treat Alzheimer's disease. Human PGC-1α has the UniProt accession number Q9UBK2 and the amino acid sequence set forth in SEQ ID NO: 1637. Accordingly, in an embodiment the therapeutic gene comprises a nucleotide sequence which encodes an amino acid sequence as set forth in SEQ ID NO: 1637, or a functional variant thereof. A functional variant of SEQ ID NO: 1637 has an amino acid sequence which is modified relative to SEQ ID NO: 1637 but which retains at least 50%, preferably at least 60, 70, 80, 90, 100, 110 or 120% or more of the specific activity of the native amino acid sequence.

In another embodiment, the therapeutic gene encodes LSD1. LSD1 is an amino oxidase histone demethylase which protects against hippocampal and cortical neurodegeneration. Specifically, LSD1 demethylates mono- and di-methylated lysine 4 on histone H3, and di-methylated lysine 9 on histone H3. Human LSD1 has the UniProt accession number O60341 and the amino acid sequence set forth in SEQ ID NO: 1638. Accordingly, in an embodiment the therapeutic gene comprises a nucleotide sequence which encodes an amino acid sequence as set forth in SEQ ID NO: 1638, or a functional variant thereof. A functional variant of SEQ ID NO: 1638 has an amino acid sequence which is modified relative to SEQ ID NO: 1638 but which retains at least 50%, preferably at least 60, 70, 80, 90, 100, 110 or 120% or more of the specific activity of the native amino acid sequence.

In another embodiment, the therapeutic gene encodes a GSK-3 inhibitor. GSK-3 inhibitors are known in the art. A number of GSK-3 inhibitors suitable for use in the present invention are disclosed in US 2016/0200763, for instance the exemplary GSK-3 inhibitors L807 (SEQ ID NO: 1645) and L807-mts (SEQ ID NO: 1646).

In another embodiment, the therapeutic gene encodes a Tau phosphorylation pseudosubstrate. A Tau pseudosubstrate is a competitive substrate for kinases which phosphorylate Tau, such as GSK-3 and the Src family kinases Lck and Fyn. Such pseudosubstrates are known in the art. Such a pseudosubstrate may be phosphorylated, but does not form neurofibrillary tangles. Such a pseudosubstrate may for instance be a peptide derived from Tau comprising one more Tau phosphorylation sites. Preferably a Tau pseudosubstrate has higher affinity for its phosphorylating kinase(s) than does full-length Tau. Tau may be phosphorylated at multiple sites, which include Ser202 and Thr205; phosphorylation of Tau at these residues is associated with the formation of neurofibrillary tangles. Accordingly, in an embodiment the Tau pseudosubstrate includes a Tau-derived peptide which includes the residues Ser202 and Thr205. The Tau pseudosubstrate may be of any suitable length, for instance at least 10, 20, 30, 40, 50, 60, 70, 80, 90, 100, 125, 150, 175, or 200 or more amino acids in length.

The nucleic acid construct disclosed herein may further comprise a Woodchuck Hepatitis Virus (WHV) Posttranscriptional Regulatory Element (WPRE). The WPRE is a DNA sequence which, when transcribed, creates a tertiary structure which enhances gene expression. The WPRE may be operatively linked to the therapeutic gene. In the case that the therapeutic gene encodes a protein the WPRE may be included in the 3' untranslated region of the therapeutic gene. Alternatively, the WPRE may be located upstream of the promoter and/or enhancer. The WPRE has the nucleotide sequence set forth in SEQ ID NO: 1631. Accordingly, the nucleic acid construct disclosed herein may further comprise the nucleotide sequence set forth in SEQ ID NO: 1639. Alternatively, the nucleic acid construct disclosed herein may comprise an active variant of the WPRE, i.e. a nucleotide sequence with at least 70, 75, 80, 85, 90 or 95% sequence identity to SEQ ID NO: 1639. An active variant of the WPRE retains at least 50%, preferably at least 60, 70, 80, 90, 100, 110 or 120% or more of the activity of the wild-type WPRE. The skilled person is well able to identify the activity of the WPRE or a variant WPRE, based on expression levels of a gene with and without an operatively linked WPRE or WPRE variant. The WPRE may be used to enhance expression of a protein-encoding therapeutic gene or a therapeutic gene which encodes a functional RNA.

The nucleic acid construct disclosed herein may comprise one or more introns. The inclusion of introns may reduce or abrogate non-specific expression of the therapeutic gene (i.e., expression of the gene in cells other than those of the entorhinal cortex), and/or enhance the stability of therapeutic gene RNA following transcription. The intron may be located upstream or downstream of the therapeutic gene. Exemplary introns which may be included in construct disclosed herein include the simian virus 40 (SV40) intron (SEQ ID NO: 1647) and the β-globin intron, or a variant of either of these introns. The β-globin intron may be derived from any animal, but in a particular embodiment is the human β-globin intron, the sequence of which is set forth in SEQ ID NO: 1648. A synthetic intron may also or alternatively be used.

Recombinant methods for the generation of a nucleic acid construct as disclosed herein are well-known in the art. Sequence elements may be amplified from genomic or plasmid DNA by PCR and assembled into a construct by e.g. restriction enzyme-based cloning or Gibson assembly. Appropriate methods are well known to the skilled person.

Methods for determining the level of sequence identity between two or more sequences are well known in the art and any convenient or available method may be used. However, for determining the degree of sequence identity between sequences, computer programmes that make pairwise or multiple alignments of sequences are useful, for instance EMBOSS Needle or EMBOSS stretcher (both Rice, P. et al., *Trends Genet.*, 16, (6) pp 276-277, 2000) may be used for pairwise sequence alignments while Clustal Omega (Sievers F et al., *Mol. Syst. Biol.* 7:539, 2011) or MUSCLE (Edgar, R. C., *Nucleic Acids Res.* 32(5):1792-1797, 2004) may be used for multiple sequence alignments, though any other appropriate programme may be used. Whether the alignment is pairwise or multiple, it must be performed globally (i.e. across the entirety of the reference sequence) rather than locally.

Sequence alignments and % identity calculations may be determined using for instance standard Clustal Omega parameters: matrix Gonnet, gap opening penalty 6, gap extension penalty 1. Alternatively the standard EMBOSS Needle parameters may be used: matrix DNAfull, gap opening penalty 10, gap extension penalty 0.5, end gap penalty false. Any other suitable parameters may alternatively be used.

For the purposes of this application, where there is dispute between sequence identity values obtained by different methods, the value obtained by global pairwise alignment using EMBOSS Needle with default parameters shall be considered valid.

As detailed above, the present disclosure provides a delivery vehicle comprising a nucleic acid construct as described above. As detailed, the delivery vehicle is suitable for delivery of the nucleic acid construct to the brain of a mammal. The particular form of the delivery vehicle is not limited, so long as it is able to deliver its cargo (i.e., the nucleic acid construct) to the brain of a mammal. In particular, the delivery vehicle is able to deliver its cargo to the brain of a human. Such delivery vehicles are known in the art.

In a particular embodiment, the delivery vehicle is a lipoplex, dendrimer, exosome or a viral vector.

A lipoplex is a complex of lipids with a nucleic acid. In a particular embodiment, the lipids of the lipoplex are in the form of a liposome, which is a spherical vesicle formed from a lipid bilayer. The vesicle comprises the nucleic acid construct cargo. Methods of synthesizing liposomes and lipoplexes are well-known in the art (see e.g. Balazs & Godbey, *J. Drug Deliv.* 2011, Article ID 326497). In another embodiment, the lipids of the lipoplex are in the form of a micelle. The lipoplex may comprise cationic lipids, to aid uptake of the lipoplex by target cells and to enhance interaction of the lipids with negatively charged DNA. The lipoplex may comprise phospholipids.

Dendrimers are repetitively branched molecules. The dendrimer may be an organic molecule. Suitable molecules for use in the generation of dendrimers are known in the art, as are methods of dendrimer synthesis (see e.g. Chaplot & Rupenthal 2014, *J. Pharm. Pharmacol.* 66: 542-556). The dendrimer may be cationic to promote interaction with the cargo nucleic acid and target cell membrane.

Exosomes are cell-derived vesicles which can be isolated from eukaryotic fluids, e.g. blood, urine and used cell culture medium. Exosomes are advantageous for use as nucleic acid carriers as they are non-immunogenic. The use of exosomes in drug delivery is known in the art (see e.g. Yang & Nadithe, 2016, *Acta Pharmaceutica Sinica B* Vol. 6(4): 287-296).

Viral vectors for use in gene therapy are well-known in the art (see e.g. Kotterman et al. 2015, *Annu. Rev. biomed. Eng.* Vol. 17:63-89). Any suitable viral vector may be used, e.g., a herpesvirus, retrovirus, lentivirus or adenovirus. In a particular embodiment, the viral vector is an adeno-associated virus (AAV).

An AAV is a replication-defective, non-enveloped virus of the genus *Dependoparvovirus*. AAVs are non-pathogenic, single-stranded DNA viruses. Particularly advantageously, AAV serotypes which cross the blood brain barrier have been developed (Deverman et al., *Nature Biotechnology* 34: 204-209, 2016), including the serotype AAV-PHP.B. In an embodiment, the delivery vehicle is an AAV, in particular of the serotype AAV-PHP.B. Many other AAV serotypes suitable for gene delivery, including gene delivery to the brain, are also known in the art and may be used in the delivery vehicles described herein, e.g., AAV-2/1, AAV-2/5, AAV-2/7, AAV-2/8, AAV-2/9, AAV-2/rh10, AAV-2/DJ and AAV-2/DJ18 (see Holehonnur et al., *BMC Neuroscience* 15:28, 2014). The AAV may be a natural or synthetic serotype. In a particular embodiment, the AAV is of the serotype AAV-2/1.

AAVs can be synthesized in cell culture, using e.g. HEK293 or HEK293T cells. AAVs and plasmids for generating AAVs are commercially available (e.g. from Addgene, USA). Commercially acquired AAV plasmids may be used in AAV synthesis in accordance with the supplier's instructions. Methods for generating AAVs are well known in the art (see e.g. Potter et al., 2014, *Mol. Ther. Methods Clin. Dev.* 1: 14034 and Chan et al., 2017, *Nature Neuroscience* 20: 1172-1179).

AAVs have a single-stranded DNA genome about 4.7 kb long. Each end of the AAV genome is formed from ITR (inverted terminal repeat) sequences. In a preferred embodiment, the construct disclosed herein is included in the AAV genome in an inverted formation, i.e., running 3' to 5'. In other words, the AAV genome is a negative sense DNA strand with respect to the construct disclosed herein. It has been found that by including the construct in the AAV genome in an inverted formation non-specific expression of the therapeutic gene may be reduced.

In a particular embodiment, the delivery vehicle is an AAV, preferably the AAV-2/1 serotype, and the construct disclosed herein is included in the AAV genome in an inverted formation. The enhancer may be the Odz3 enhancer; the promoter may be the TRE3G minimal promoter; the enhancer may be located immediately upstream of the promoter (this refer to the location of the enhancer relative to the promoter when the construct is in its forward, 5'-3' orientation; when the construct is inverted in the single-stranded DNA genome of an AAV the enhancer would appear immediately downstream of the enhancer); the WPRE may be located immediately upstream of the enhancer (again, this would appear immediately downstream of the enhancer when the construct is present in an AAV genome in inverted formation).

Other known gene therapy vectors may also be used, for instance a polymersome (which is a synthetic version of a liposome, made of amphiphilic block copolymers) or a polyplex (a complex of the nucleic acid construct and cationic polymers; exemplary cationic polymers include polyethyleneimine, chitosan, poly(beta-amino esters) and polyphosphoramidate).

In another aspect, provided herein is a nucleic acid construct as defined above in which the enhancer which specifically drives gene expression in cells of the entorhinal cortex comprises a nucleotide sequence as set forth in any one of SEQ ID NOs: 1-6, 9, 10, 870-881 and 886-889, or a nucleotide sequence with at least 70, 75, 80, 85, 90 or 95% sequence identity to any one of these sequences.

In other words, a nucleic acid construct comprises:
(i) an enhancer which specifically drives gene expression in cells of the entorhinal cortex, wherein said enhancer comprises a nucleotide sequence as set forth in any one of SEQ ID NOs: 1-6, 9, 10, 870-881 and 886-889, or a nucleotide sequence with at least 70, 75, 80, 85, 90 or 95% sequence identity to any one of these sequences;

(ii) a promoter; and
(iii) a therapeutic gene,
wherein said enhancer, promoter and therapeutic gene are operatively linked, said enhancer and therapeutic gene are heterologous, and said delivery vehicle is suitable for delivery of the nucleic acid construct to the brain of a mammal. The nucleic acid construct of the invention is as defined above with respect to the nucleic acid construct comprised within the delivery vehicle.

In another embodiment, the nucleic acid construct comprises an enhancer which comprises a nucleotide sequence which is a fragment of any one of SEQ ID NOs: 871, 873, 875, 877, 879, 881, 887 and 889, wherein the fragment corresponds to a nucleotide sequence which is obtainable by the deletion of 1 to about 500 nucleotides from the 5' end and/or the deletion of 1 to about 500 nucleotides from the 3' end of any one of SEQ ID NOs: 871, 873, 875, 877, 879, 881, 887 and 889. In another embodiment, the enhancer which specifically drives gene expression in cells of the entorhinal cortex comprises a variant of a fragment of any one of SEQ ID NOs: 871, 873, 875, 877, 879, 881, 887 and 889, wherein the variant of a fragment has a nucleotide sequence having at least 70, 75, 80, 85, 90 or 95% sequence identity to a fragment of any one of SEQ ID NOs: 871, 873, 875, 877, 879, 881, 887 and 889, wherein the fragment of any one of SEQ ID NOs: 871, 873, 875, 877, 879, 881, 887 and 889 is as defined above.

In another aspect, a cell comprises a nucleic acid construct as disclosed herein. Such a cell may be considered a host cell. The host cell may be a prokaryotic (e.g., bacterial) or eukaryotic (e.g., mammalian) cell. The host cell may in particular be used as a cloning host for the nucleic acid construct. A cloning host may be a prokaryotic cell. Suitable prokaryotic cells for use as cloning hosts include without limitation, eubacteria, such as Gram-negative or Gram-positive organisms, for example Enterobacteriaceae such as *Escherichia*, in particular *E. coli*, and *Bacilli* such as *B. subtilis*. The cloning host may alternatively be a eukaryotic cell such as a fungal cell, e.g., *Pichia pastoris*, or a yeast cell, or even a higher eukaryotic cell such as a mammalian cell.

The nucleic acid construct may be integrated into the host cell chromosome, but is preferably maintained extra-chromosomally. The nucleic acid construct may be introduced into a host cell by any method known in the art. Such methods include, in particular, for prokaryotic cells transformation, transduction and conjugation. Transformation refers to the genetic alteration of a competent bacterium by direct uptake of DNA. Transduction refers to infection of a bacterium using a bacteriophage in order to introduce DNA of interest. Conjugation refers to the direct transfer of genetic material between bacterial cells in direct contact.

For eukaryotic cells, the nucleic acid construct may be introduced by transfection or transduction. Transfection may be accomplished by a variety of means known in the art including but not limited to calcium phosphate-DNA co-precipitation, DEAE-dextran-mediated transfection, polybrene-mediated transfection, electroporation, microinjection, liposome fusion, lipofection, protoplast fusion, retroviral infection, and biolistics. Transduction refers to the delivery of a gene(s) using a viral or retroviral vector by means of viral infection rather than by transfection. In certain embodiments, retroviral vectors are transduced by packaging the vectors into viral particles or virions prior to contact with a cell. The skilled person is well aware of appropriate methods for introducing such genetic material into a host cell.

In another aspect the invention provides a composition a delivery vehicle of and at least one physiologically-acceptable diluent, carrier or excipient. The compositions may be formulated in any convenient manner according to techniques and procedures known in the pharmaceutical art. "Pharmaceutically acceptable" as used herein refers to ingredients that are compatible with other ingredients of the compositions as well as physiologically acceptable to the recipient. The nature of the composition and carriers or excipient materials, dosages etc. may be selected in routine manner according to choice and the desired route of administration, purpose of treatment etc.

The pharmaceutical composition may be prepared for administration to a subject by any suitable means. Such administration may be e.g., oral, rectal, nasal, topical or parenteral. Oral administration as used herein includes buccal and sublingual administration. Topical administration as used herein includes transdermal administration. Parenteral administration as defined herein includes subcutaneous, intramuscular, intravenous, intraperitoneal and intradermal administration. Preferably the composition is suitable for parenteral administration.

Pharmaceutical compositions as disclosed herein include liquid solutions or syrups, solid compositions such as powders, granules, tablets or capsules, creams, ointments and any other style of composition commonly used in the art. Suitable pharmaceutically acceptable diluents, carriers and excipients for use in such compositions are well known in the art. For instance, suitable excipients include lactose, maize starch or derivatives thereof, stearic acid or salts thereof, vegetable oils, waxes, fats and polyols. Suitable carriers or diluents include carboxymethylcellulose (CMC), methylcellulose, hydroxypropylmethylcellulose (HPMC), dextrose, trehalose, liposomes, polyvinyl alcohol, pharmaceutical grade starch, mannitol, lactose, magnesium stearate, sodium saccharin, talcum, cellulose, glucose, sucrose (and other sugars), magnesium carbonate, gelatin, oil, alcohol, detergents and emulsifiers such as polysorbates. Stabilising agents, wetting agents, emulsifiers, sweeteners etc. may also be used.

Preferably the composition is a liquid composition. Liquid pharmaceutical compositions, whether they be solutions, suspensions or other like form, may include one or more of the following: sterile diluents such as water for injection, saline solution (preferably physiological), Ringer's solution, isotonic sodium chloride, fixed oils such as synthetic mono- or diglycerides which may serve as a solvent or suspending medium, polyethylene glycols, glycerin, propylene glycol or other solvents; antibacterial agents such as benzyl alcohol or methyl paraben; antioxidants such as ascorbic acid or sodium bisulfate; chelating agents such as EDTA; buffers such as acetates, citrates or phosphates and agents for the adjustment of tonicity such as sodium chloride or dextrose. A parenteral preparation can be enclosed in ampoules, disposable syringes or multiple dose vials made of glass or plastic. An injectable pharmaceutical composition is preferably sterile.

In another aspect, provided herein is a method of treating or preventing Alzheimer's disease, comprising administering a delivery vehicle or a composition as described herein to a subject in need thereof. The method of treating or preventing Alzheimer's disease is a method of gene therapy.

The subject to which the delivery vehicle or composition is administered may be any mammal, e.g., a farm animal such as a cow, horse, sheep, pig or goat, a pet animal such as a rabbit, cat or dog, a laboratory animal such as a mouse or a rat, or a primate such as a monkey, chimpanzee, gorilla or human. Most preferably the subject is a human.

A subject in need of the treatment or prevention of the invention is any subject suffering from Alzheimer's disease or at risk of developing Alzheimer's disease. A subject suffering from Alzheimer's disease may be identified based on symptoms characteristic of the disease (as described above), or may be asymptomatic but displaying brain pathology indicative of early Alzheimer's disease, as may be identified by scans or the like. For instance, in a subject with early-stage Alzheimer's disease a brain scan (e.g. a CT scan or MRI scan) may show shrinkage of the hippocampus and surrounding area.

A subject at risk of Alzheimer's disease may be specifically identified based on family history (i.e., a family history of Alzheimer's disease). A subject at risk of Alzheimer's disease may alternatively be any other person of any age who has not developed Alzheimer's disease, but who might develop the disease in the future. The delivery vehicle described herein can prevent Alzheimer's and so may function as a vaccine against the disease. Accordingly, it is envisaged that the delivery vehicle or composition will be widely administered across society in an organised vaccination programme. Vaccinations may be given in childhood or at any later age to prevent the development of the disease.

The delivery vehicle or composition may be administered to the subject by any suitable means. Administration may be e.g., oral, rectal, nasal, topical or parenteral. Preferably the administration is parenteral. The delivery vehicle or composition of the present invention may be administered at a dosage appropriate to the subject, based on e.g. the condition, size or age of the subject.

In another aspect, provided is a method of driving entorhinal cortex-specific gene expression in a mammalian subject, said method comprising administering to said subject a delivery vehicle or a composition as described herein.

The subject to which the delivery vehicle or composition is administered, and the method of administration, may be as detailed above with regard to the method of treatment or prevention of Alzheimer's disease.

EXAMPLES

Example 1: Generation of Transgenic Mice

Introduction

The inventors performed Chromatin Immunoprecipication with high-throughput sequencing (ChIP-seq) (Cotney et al., 2013; Reilly et al., 2015; Visel et al., 2009) of microdissected adult murine cortical sub-regions and compared active enhancers in each. The inventors found a similar number of active putative enhancers in each cortical sub-region as one typically finds in ChIP-seq of entire organs. Moreover, a large number of the putative enhancers were novel enhancer sequences, and many of them were specific to particular cortical sub-regions. Remarkably, when the inventors created transgenic mice based on single enhancers found to be specific to the medial entorhinal cortex (MEC), they often drove expression specifically in distinct subsets of MEC neurons. These data thereby not only serve to illustrate the enormous diversity of neuronal cell types in the adult brain, they also provide a means to generate cell type-specific genetic tools in a targeted manner, a method the inventors call Enhancer Driven Gene Expression (EDGE).

Methods

Microdissection

Two C57black6 mice (P56) were deeply anaesthetised by injection with pentobarbital (100 mg/ml in 96% ethanol, Ås Produksjonslab AS, Norway). The brains were removed and horizontal or coronal 500 µm sections were cut on a Leica VT 1000 S microtome and kept at 4° C. until dissection. Bilateral dissection was performed, while watching the tissue through a dissection microscope with transmitted and reflected white light (Zeiss Discovery V8 stereomicroscope) applying architectonic criteria (Boccara et al., 2015; Jones and Witter, 2007; O'Reilly et al., 2015; Sugar and Witter, 2016; Witter, 2011) to unstained tissue. The tissue samples were snap-frozen in liquid nitrogen, kept at −800° C. and shipped on dry ice.

All dissections avoided border regions, i.e., were taken centred in the identified cortical area. In horizontal sections, the MEC is easily recognized by the marked shape of the cortex, the prominent white, opaque lamina dissecans and the radial organization of the layers deep to the latter. Layer II neurons are large spherical neurons, which differ markedly in level of opacity from those in Layer III. The medial border between MEC and parasubiculum is characterized by the loss of the differentiation between Layers II and III, and the border with the laterally adjacent postrhinal cortex is characterised by the loss of the large spherical neurons in Layer II. The inventors only sampled the more dorsal and central portions of the MEC. The LEC shares the large Layer II neurons with the MEC, but the radial organisation in Layer V is absent. The anterior and dorsal border of the LEC with the perirhinal cortex is characterized by the abrupt disappearance of the large Layer II neurons. The inventors only sampled the most lateral portions of the LEC, to avoid contamination with ventromedially adjacent components of the amygdaloid complex. The ACC and RSC were sampled from the medial wall of the lateral hemisphere above the corpus callosum, avoiding the most anterior part of the ACC and the posteroventral part of the RSC. Since the border between the two areas coincides with the dorsal-anterior tip of the hippocampal formation, all samples avoided that border region.

In coronal sections, ACC and RSC samples were taken dorsal to the corpus callosum, just below the shoulder of the medial wall of the hemisphere down to, but not touching, the corpus callosum, to avoid inclusion of the indusium griseum. Samples were taken from sections anterior to the most anterodorsal tip of the hippocampal formation in case of the ACC and posterior to the tip in case of the RSC. Samples of the LEC were collected one section after the disappearance of the piriform cortex characterised by a densely packed thick Layer II, a polymorphic lightly-packed deeper cell layer and the presence of the endopiriform nucleus. The LEC shows cytoarchitectonic features similar to those described above. The inventors sampled only from the vertical part of the LEC, directly below the rhinal fissure. For the MEC, samples were collected from more posterior coronal sections, using shape of the section, the presence of the ventral hippocampus and cytoarchitectonic features as described above, as selection criteria.

ChIP-Seq

All dissected brain tissues were briefly homogenised and cross-linked with 1% formaldehyde at room temperature with rotation for 15 min. Cross-linking was quenched with glycine (150 mM in PBS), then tissue was washed and flash frozen. Chromatin was extracted as previously described (Cotney et al., 2013; Cotney and Noonan, 2015). Briefly, nuclei were extracted, lysed, and sonicated (30 min, 10 sec pulses) to produce sheared chromatin with an average length of ~250 bp. 1 to 10 micrograms of final soluble chromatin was used for each ChIP and combined with Protein G Dynabeads® (Invitrogen, cat #10004D) prebound with 5 µg of antibodies to H3K4me2 (Abcam ab7766) or H3K27ac (Abcam ab4729).

Immunoprecipitated chromatin was washed five times with 1 mL of wash buffer and once with TE. Immunoprecipitated chromatin was eluted, cross-links were reversed, and DNA was purified. Libraries were prepared for sequencing using NEBNext® ChIP-Seq Library Prep reagents and sequenced on the Illumina HiSeq™ 2000 platform at the Yale Center for Genome Analysis.

ChIP-Seq Data Analysis

ChIP-Seq data was initially processed as previously described (Reilly et al., 2015). Briefly, reads were aligned to the mm9 version of the mouse genome using bowtie (v1.1.1) (Langmead and Salzberg, 2012). Enriched regions were identified in individual replicates using a sliding window method as previously described (Mikkelsen et al., 2010). Enriched regions were divided into functional categories based on overlaps with genomic features as annotated by Ensembl v67 using Bedtools (2.19.0) (Quinlan and Hall, 2010). Reproducibly enriched regions were determined as the union of overlapping regions identified in both biological replicates. Putative enhancer regions from intergenic and intronic portions of the genome were then assigned target genes using GREAT. H3K27ac ChIP-Seq reads were retrieved from Encodeproject.org for 17 mouse tissues (Shen et al., 2012) and uniformly processed as above. Enhancers for all cell types were combined and merged to generate a uniform annotation of all possible enhancers. H3K27ac counts at each enhancer from each tissue were calculated using mrfQuantifier (Habegger et al., 2011). Pearson correlations for all enhancer signals were calculated and plotted using R. K-means clustering of H3K27ac count matrix was performed using Cluster (v3.0) (de Hoon et al., 2004). Rows were centred on the mean value of the row and normalised, the k parameter was the total number of tissues, and 100 runs were performed.

The clustering result was then visualized using Java TreeView (Saldanha, 2004). Sub-region specific clusters of enhancers were intersected with peak calls from all other tissues to identify enhancers with likely tissue-specific function. Sub-region-specific enhancers were assigned two target genes using GREAT, ranked by H3K27ac signal, and overlapped with vertebrate conserved sequences (Siepel et al., 2005). These enhancers were then prioritized based on brain expression as measured by in situ hybridisation in multiple mouse brain sections available in the Allen Brain Atlas (Lein et al., 2007).

Cloning of Transgenic Constructs

Figure 3:
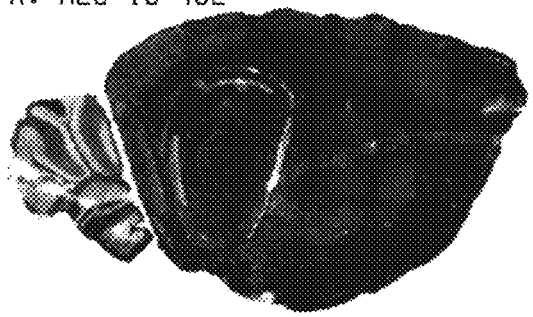
FIG. 3 shows expression of hGFP driven by 8 unique enhancers. The sagittal sections shown are of approximately similar levels of the brain. All mice were crosses of different enhancer lines with hGFP mice. Enhancer lines of all 8 different enhancers used (A. MEC-13-48E, B. MEC-13-53A, C. MEC-13-81B, D. MEC-13-104B, E. MEC-13-79A, F. MEC-13-95H, G. MEC-13-32B, H. MEC-13-123B) show expression in the MEC when the mice were crossed with hGFP mice.
Figure 3:
Figure 3:
Figure 3:
Figure 3:
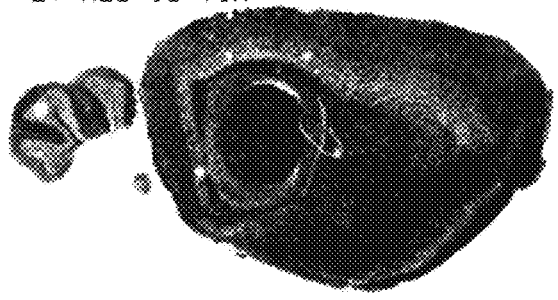
Figure 3:
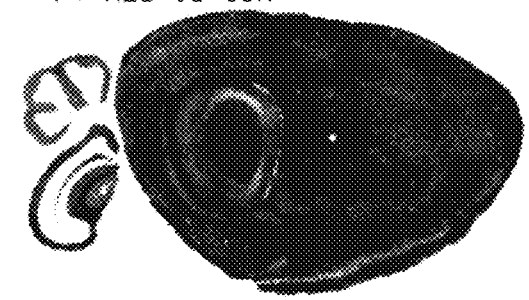
Figure 3:
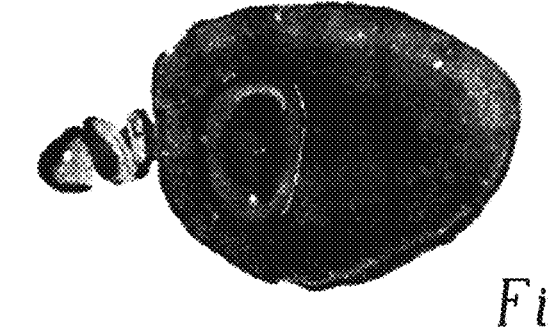
Figure 3:
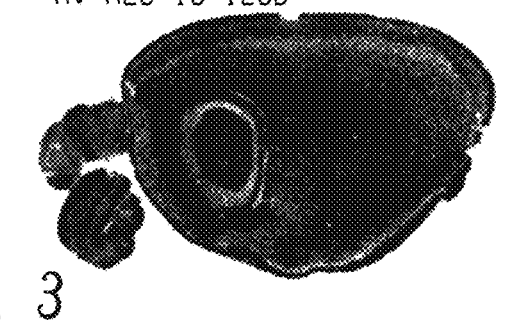

The putative enhancers sequences were cloned from BACs (chori.org) and transferred to pENTRtm/DTOPO® vectors by TOPO® cloning (Invitrogen, K2400-20). The putative enhancers were transferred to injection plasmids by Gateway Cloning® (Invitrogen, 11791-019). The resulting plasmids consist of a putative enhancer followed by a mutated heatshock promoter 68 (HSP68), a tTA gene, a synthetic intron and a WPRE element (FIG. 3).

Pronuclear Injection

The eight injection plasmids were linearised by enzyme digestion to keep the relevant elements but remove the bacterial elements of the plasmids. Linearised vectors were run on a 1% agarose gel and isolated using a Zymoclean™ Gel DNA Recovery Kit (Zymo research, D4001). Fertilised egg cells were injected with 1 µl of DNA at concentrations of 0.5 to 1 ng/µl, leading to surviving pups of which 96 were genotypically positive for MEC and 68 were genotypically positive for LEC.

Mouse Husbandry

All genotypically positive founders were mated with histone GFP mice (Jackson laboratory, Tg(tetOHIST1H2BJ/GFP)47Efu, stock no. 005104). Double positive pups were used for further analysis. Subsequent crosses were done with GCamp6 mice (Weible et al., 2014), TVAG mice (Line TVAG5 from (Weible et al., 2010)), Arch mice (tetO arch, made in-house), tetO-EGFP (Jackson laboratory, C57BL/6JTg(tetO-EGFP/Rpl10a)5aReij/J_JAX) and HM3 mice (Alexander et al., 2009).

Genotyping

Genotyping was done on ear tissue using a Kapa mouse genotyping kit (Kapa Biosystems, Cat #KK7302). Primer pairs for the appropriate gene (Table 3) and internal controls (Table 4) were added to the PCR mixture at a final concentration of 10 µM. The PCR reaction was performed with an initial step of 4 minutes at 95° C., then 20 cycles of 1 minute at 95° C., 30 seconds at 70° C. reduced by 0.5° C. each cycle, and 30 seconds at 72° C. This was followed by 20 cycles of 30 seconds at 95° C., 30 seconds at 60° C., and 30 seconds at 72° C., then a final 7 minute step at 72° C. The products were run on a 1% agarose gel along with positive and negative controls.

TABLE 3

| Gene | Primer 1 | Primer 2 | Product Size (bp) |
|---|---|---|---|
| tTA | GGACAAGTCCAAGGTGATCAAC<br>SEQ ID NO: 1649 | CCTGGTGGTCGAACAGCTCG<br>SEQ ID NO: 1650 | 591 |
| hGFP | TGGGGACGGTGATGCGGTCT<br>SEQ ID NO: 1651 | ACGTGGCGAAGCTCTGCTGC<br>SEQ ID NO: 1652 | ~300 |
| TVAG | GTCCGGTAACGGTTCTTTG<br>SEQ ID NO: 1653 | GCTCTTGTCAGGCACCAG<br>SEQ ID NO: 1654 | 391 |
| Arch | CTTCTCGCTAAGGTGGATCG<br>SEQ ID NO: 1655 | CACCAAGACCAGAGCTGTCA<br>SEQ ID NO: 1656 | 246 |
| GCamp6 | TGGGGACGGTGATGCGGTCT<br>SEQ ID NO: 1657 | ACGTGGCGAAGCTCTGCTGC<br>SEQ ID NO: 1658 | ~300 |
| HM3 | ACCGTCAGATCGCCTGGAGA<br>SEQ ID NO: 1659 | TCATCGGTGGTACCGTCTGGAG<br>SEQ ID NO: 1660 | 200 |

TABLE 4

| Gene | Internal Control Primer 1 | Internal Control Primer 2 | Product Size (bp) |
|---|---|---|---|
| tTA | CTAGGCCACAGAATTGAAAGATCT<br>SEQ ID NO: 1661 | GTAGGTGGAAATTCTAGCATCATCC<br>SEQ ID NO: 1662 | 324 |
| hGFP | CAAATGTTGCTTGTCTGGTG<br>SEQ ID NO: 1663 | GTCAGTCGAGTGCACAGTTT<br>SEQ ID NO: 1664 | 200 |
| TVAG | CGTCTTTAATTGGATTACAATGCT<br>SEQ ID NO: 1671 | CTAGCAAGTGGTTGTGGTCA<br>SEQ ID NO: 1672 | 181 |
| Arch | CTAGGCCACAGAATTGAAAGATCT<br>SEQ ID NO: 1665 | GTAGGTGGAAATTCTAGCATCATCC<br>SEQ ID NO: 1666 | 324 |
| GCamp6 | CAAATGTTGCTTGTCTGGTG<br>SEQ ID NO: 1667 | GTCAGTCGAGTGCACAGTTT<br>SEQ ID NO: 1668 | 200 |
| HM3 | TCCTCAAAGATGCTCATTAG<br>SEQ ID NO: 1669 | GTAACTCACTCATGCAAAGT<br>SEQ ID NO: 1670 | 340 |

Tissue Treatment of Histone GFP-Expressing Mice

The double positive (tTA+/−, hGFP+/−) animals were terminated by IP injection with pentobarbital and brains were removed and dropfixed in paraformaldehyde (4% in 1× phosphate-buffered saline, freshly made). Sections (30 µm) were mounted and scanned.

In Situ Hybridisation

Double positive mice (tTA+/−, reporter gene+/−) were deeply anaesthetised with pentobarbital and transcardially perfused with 0.9% saline first and freshly made 4% formaldehyde (in 1×DPBS, Thermofisher, Cat #14200075) second. Brains were removed and postfixed overnight in 4% paraformaldehyde. Subsequently the brains were dehydrated for at least 24 h with 30% sucrose in 1×PBS. The brains were sectioned sagittally at 30 µm on a cryostat, mounted directly (on Fisherbrand™ Superfrost™ Plus microscope slides (Fisher Scientific Cat #12-550-15)) and dried overnight at room temperature. Slides were stored at −80° C.

Slides were thawed in closed containers. Sections were outlined with a PAP pen (Sigma, cat #Z377821-1EA). The probe was diluted (usually 0.1-1 µg/ml) in hybridisation buffer (1:10 10× salt solution, 50% deionised formamide (sigma, cat #D-4551), 10% dextran sulfate (sigma, cat #D-8906), 1 mg/ml rRNA (sigma, Cat #R5636), 1× Denhardt's (Sigma cat #D-2532). Salt solution (10×) is made with 114 g NaCl, 14.04 g TrisHCl, 1.3 g TrisBase, 7.8 g $NaH_2PO_4.2H_2O$, 7.1 g $Na_2HPO_4$ in $H_2O$ to 1000 ml with a final concentration of 0.5 M EDTA). The probe was denatured for 10 min at 62° C., added to the section and coverslipped (Fisher, cat #12-548-5P). The slides were incubated overnight at 62° C. in a closed box with filter paper wetted in 1×SSC with 50 formamide. Slides were transferred to polypropylene Coplin jars containing 1×SSC with 50% formamide and 0.1% Tween-20 warmed to 62° C. for 10 minutes to allow the coverslips to fall off. The slides were washed 3×30 minutes at 62° C. Then the slides are washed 3×30 minutes in MABT (11.6 g Maleic acid (Sigma, cat #M0375-1 kg), 8.76 g NaCl, 5 ml 20% tween, pH 7.5, dd$H_2O$ to 1000 ml) at room temperature.

The slides were drained (but not dried), re-circled with a PAP pen, and blocking solution (600 µl MABT, 200 µl sheep serum, 200 µl 10% blocking reagent (Roche cat #11 096 176 001) was added. Slides were then incubated in a Perspex box with wetted filter paper at room temperature for 2-3 hours. The slides were drained and 1:5,000 sheep anti-digoxigenin-AP antibody in blocking solution was added. The slides were incubated overnight.

4 g of polyvinyl alcohol was dissolved in 40 ml AP (alkaline phosphatase) staining buffer (100 mM NaCl, 50 mM $MgCl_2$, 100 mM Tris pH 9.5, 0.1% Tween-20) by heating, and the solution then cooled to 37° C. The slides were washed in MABT 5 times for 4 minutes, then washed 2×10 minutes in AP staining buffer. Nitroblue tetrazolium chloride (Roche, cat #11 383 213 001) was added at 3.5 µl/ml, 5-Bromo-4-chloro-3-indolyl-phosphate,4-toluidene salt (Roche. cat #11 383 221 001) at 2.6 µl/ml) and Levamisole (Vector. cat #SP-5000) at 80 µl/ml) to the cool polyvinyl alcohol solution.

The solution was then shaken well and transferred to a Coplin jar. The slides were added and incubated at 37° C. for 3 to 5 hours. The reaction was stopped by washing in 2×PBS with 0.1% Tween-20. The slides were then washed 2× in ddH$_2$O, dehydrated quickly through graded ethanol of 50%, 70%, 95% and finally 100%. The slides were finally cleared in xylene and coverslipped.

Immunohistochemistry

Double positive mice (tTA+/−, TVAG+/−) were deeply anaesthetised with pentobarbital and transcardially perfused with approximately 30 ml 0.9% saline first and approximately 30 ml freshly made 4% paraformaldehyde (in 1×DPBS, Thermofisher, Cat #14200075) second. Brains were removed and postfixed for 24 hours in 4% paraformaldehyde. Subsequently the brains were dehydrated with 30% sucrose in 1×PBS. The brains were sectioned horizontally at 50 µm and kept in TCS (tissue collection solution, 25% glycerol, 35% ethyl glycol, 50% 1×DPBS) at −20° C.

Immunohistochemistry was performed by initially washing the brain sections twice for 10 minutes in 1×DPBS and subsequently permeabilising them by a 60 minute wash in 1% Triton X-100 (Sigma, Cat #T9284) in 1×DPBS. The tissue was then incubated in primary antibody in 1×DPBS with 1 trition X-100 and 5% donkey serum (Sigma, Cat #D9663) for 48 hours at 4° C. Primary antibodies and dilutions were: Rabbit-anti-2A (1:2000, Millipore, cat #ABS31), Mouse-anti-reelin (1:1000, Millipore, cat #Mab5364), Mouse-anti-GAD67 (1:1000, Millipore, cat #Mab5406), Mouse-anti-calbindin (1:10,000, Swant, cat #CB300), Mouse-anti-calretinin (1:1000, Millipore, cat #Mab1568).

After incubation with primary antibodies, sections were washed 4× in 1×DPBS (10 minutes per wash) and 2× in 1×DPBS with 1% Triton X-100. Then sections were incubated for 6 h at room temperature in secondary antibody (all secondary antibodies were raised in Donkey and diluted 1:250). The secondary antibodies were: anti-Rabbit-AF488 (Jackson ImmunoResearch, Cat #711-545-152) and anti-Mouse-Cytm3 (Jackson ImmunoResearch, Cat #715-165-151). The sections were DAPI stained by a single 10 minute wash in 1×DPBS with 0.2 µg/ml DAPI (Thermofisher, D1306) and finally washed 5× (10 minutes per wash) in 1×DPBS. Sections were mounted on Superfrost® plus glass slides (VWR, Cat #631-9483) and coverslipped with Poly Vinyl Alcohol with 2.5% DABCO (Sigma, Cat #D27802).

Imaging

From mice in the lines MEC-13-53A×TVAG and MEC-13-104B×TVAG, MECs were imaged in sections from three different dorsal-ventral levels with a Zeiss Meta 880 confocal microscope. For each section, three to seven slices in the Z direction with 1.5 µm spacing were taken, with a 20× objective and tiling to cover the entire MEC. Two channels were imaged, one for AF488 with maximum excitation wavelength at 488 nm and maximum emission wavelength at 528 nm and one for Cy3 with maximum excitation wavelength at 561 nm and maximum emission wavelength at 595 nm.

For display images, sections were imaged on Zeiss Axio Scan.Z1 scanners in three preset channels: DAPI, d1488 and d1549.

Image Processing

From the Zeiss proprietary file format .lsm, .tiff files were exported. These were processed in Adobe Photoshop, all alterations in levels were made on the entire images. In some cases images were processed to remove visual artefacts.

Counting

Counts were made on the confocal images of single positive cells' expression of transgenes or native genes (GAD67, Reelin, Calbindin, calretinin), and of cells expressing both. Graphs were made in Microsoft Excel, statistical analysis was done in SPSS.

Results

Figure 1A:
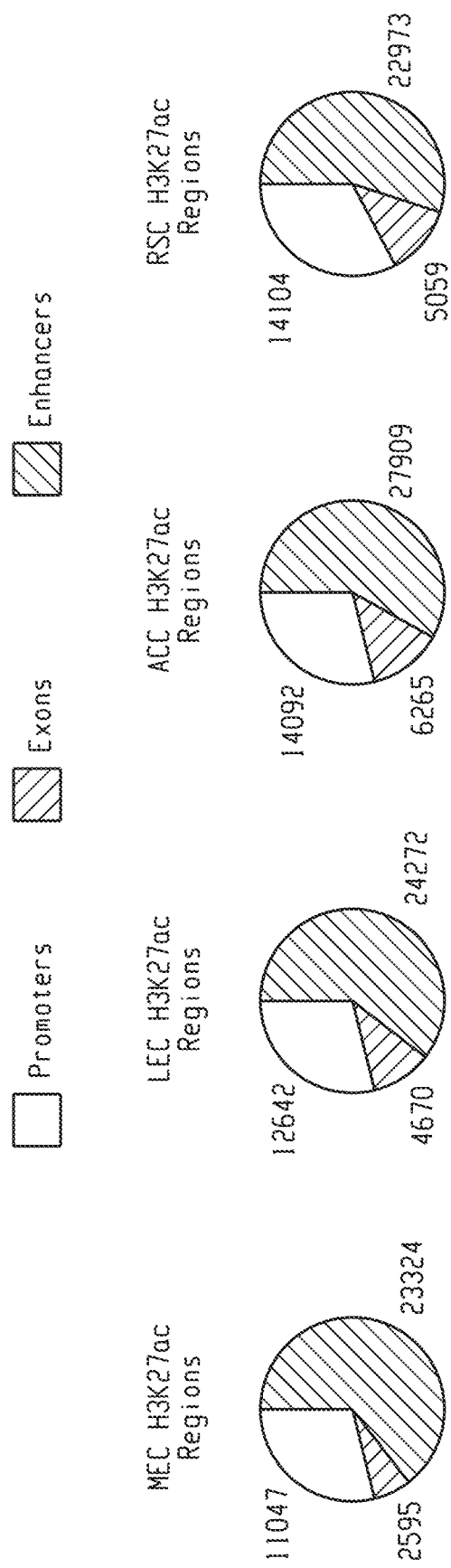
FIG. 1A-C collectively show the results of ChIP-seq analysis of brain region-specific enhancers, revealing a striking diversity of unique and novel enhancers in different cortical sub-regions.

Enhancer ChIP-Seq of Cortical Sub-Regions Reveals a Striking Diversity of Unique Enhancers The following brain regions from two adult (P56) male C57BL6J mice were microdissected: the medial entorhinal cortex (MEC), the lateral entorhinal cortex (LEC), the retrosplenial cortex (RSC), and the anterior cingulate cortex (ACC). Each mouse was processed separately and the samples were used as biological replicates for further analysis. ChIP-seq was performed on homogenised tissue against the active-enhancer-associated histone modifications H3K27ac and H3K4me2 in samples of each of the four brain regions. The regions enriched for H3K27ac reproducibly identified similar numbers of active promoters and distal cis-regulatory sequences between two replicates of each brain sub-region (FIG. 1A). Nearly 90% of all active promoters were identified in at least two samples with the remainder being active in only one sub-region (17032 total, 2045 unique).

When more distal sites were analysed (>5 kb from a transcriptional start site) the inventors identified a total of 59372 reproducibly active enhancers in at least one sub-region. Of these, 31% were only identified in a single cortical sub-region (18185 unique relative to other sub-regions). Surprisingly the number of sub-region specific enhancers in the cortex was similar to the number of total enhancers active in any single tissue thus far interrogated (Roadmap Epigenomics et al., 2015; Shen et al., 2012). Furthermore 81% (48077) of enhancers identified in these sub-regions were not identified in bulk cortex tissue from mouse, demonstrating the potentially vast repertoire of enhancers active in the brain.

Interestingly, when comparing the total number of reproducible peak calls in these 4 cortical sub-regions (59372) to the number identified in bulk cortex treated in the same way (13472), the number of putative active enhancers one obtains from the four cortical sub-regions is far greater than what one obtains from the entire cortex, even though these four cortical regions compose only a small minority of the entire cortex. Of course, this is comparing 4 pooled samples to a single sample, but each of the individual samples gives numbers similar to bulk cortex (FIG. 1). Without being held to theory, it is believe that the most likely explanation for this superficially puzzling result is a reduction in signal to noise ratio when pooling heterogeneous sets of tissues for ChIP-seq. This would tend to favour those enhancers that are expressed throughout many cortical sub-regions at the expense of more specifically expressed enhancers. In support of this, 89% of cortical enhancers were found in one or more cortical sub-regions, and 78% were found in at least 2 cortical sub-regions. In comparison, fully 31% of the enhancers found by the inventors in the analysed sub-regions were specific to a single sub-region.

Figure 1B:
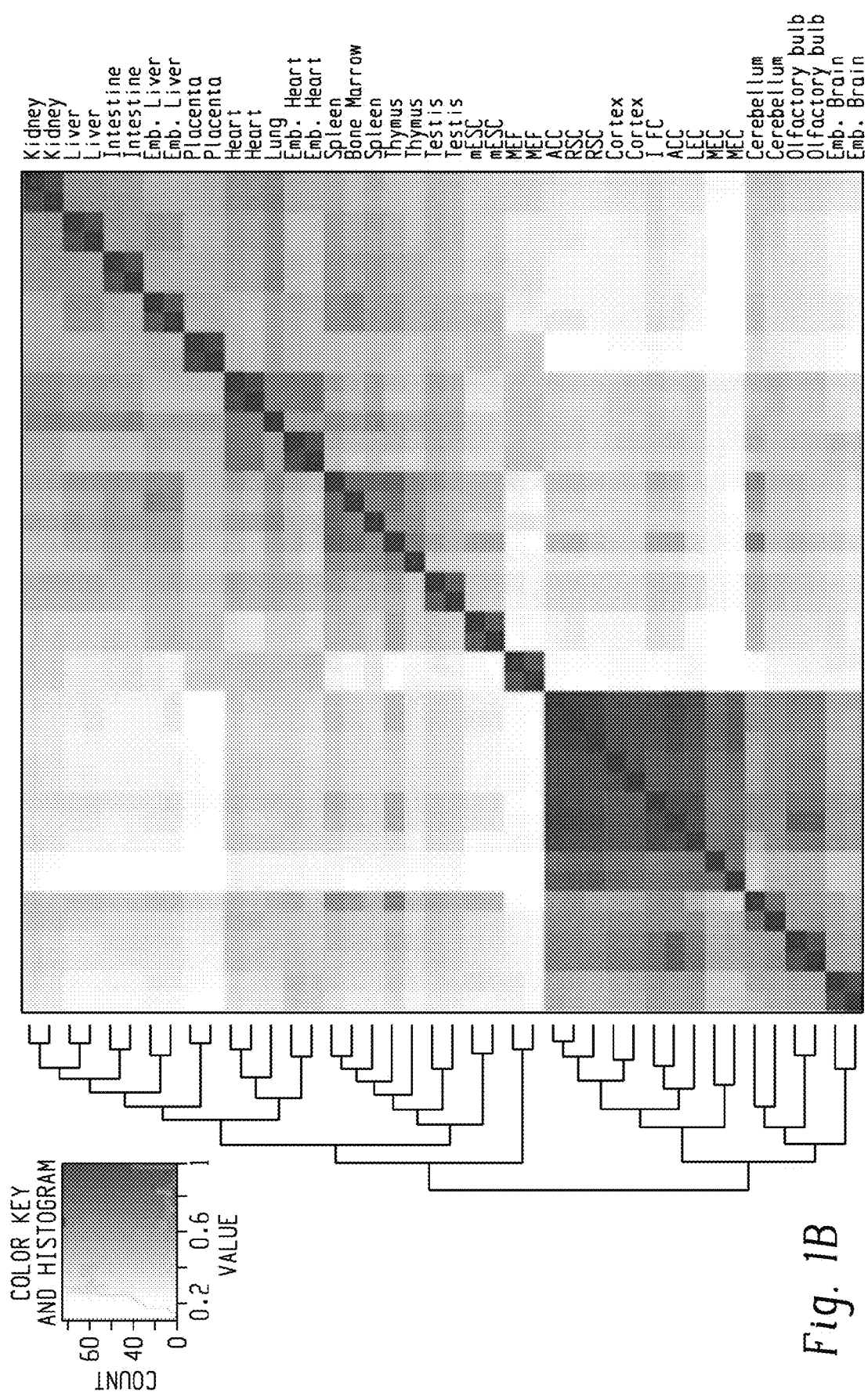

While many of the enhancers identified by peak calls alone are specific to this small number of cortical sub-regions, the goal of the study was to identify very specific regulatory sequences with limited activity within other regions of the brain as well as the rest of the body. To ensure the identification of such sequences and exclude regions with weak activity elsewhere, the inventors expanded their comparisons to include a variety of mouse adult tissues and cultured cell types (Shen et al., 2012). The inventors first identified active putative enhancers in additional mouse samples and merged them to create a unified set of enhancers for consistent comparisons across all samples. The inventors then extracted normalised H3K27ac counts at 108299 discrete regions from the sub-regions profiled in this study as well as those from 17 mouse ENCODE samples (Shen et al., 2012). Hierarchical clustering of samples revealed two main groups of mouse tissues: neuronal and non-neuronal (FIG. 1B). Amongst non-neuronal tissues, the strongest correlations were observed amongst developmental stages of the heart and tissues that make up the immune system: bone marrow, thymus, and spleen. In neuronal tissues the four cortical sub-regions profiled here were well correlated across all enhancers assayed but clustered distinctly from cerebellum, olfactory bulb, and embryonic brain. This analysis revealed that while the samples of this study are distinct from most tissues of the mouse there could be sharing in enhancer activation amongst other larger brain regions such as the cerebellum.

Figure 1C:
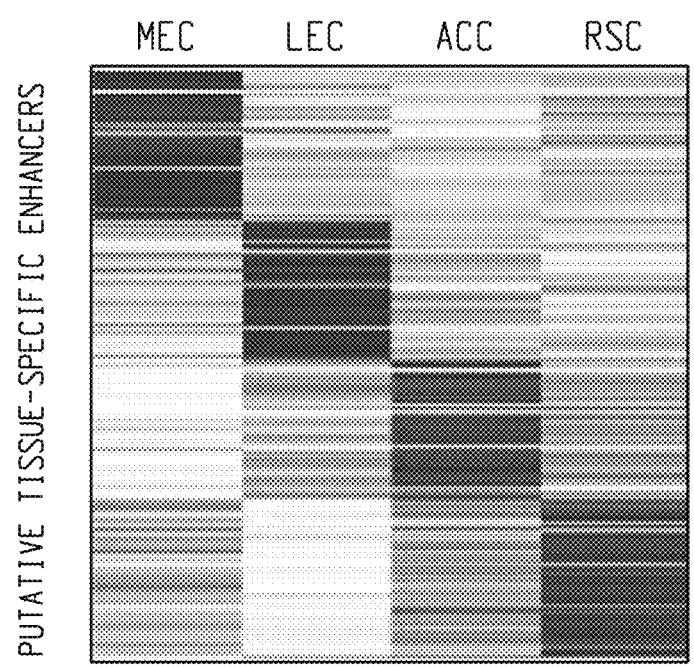

The inventors then utilized k-means clustering to identify enhancers that were significantly more active in each cortical region (FIG. 1C). Those enhancers that were identified as most specifically active in a given sub-region were then further filtered based on those that were never identified by peak calling in any other mouse tissue. This stringent analysis yielded 156 to 1824 completely novel putative distal enhancers for each cortical sub-region (FIG. 1C). We then assigned these novel enhancers to putative target genes based upon the GREAT algorithm (McLean et al., 2010). Gene ontology analysis suggested that these novel enhancers are enriched near genes associated with a variety of neuronal functions.

Region-Specific Enhancers Drive Transgene Expression in the Targeted Cortical Sub-Regions To test the specificity of these novel enhancers the inventors prioritised them based on H3K27ac signal, conservation across 30 species and expression of two flanking genes based on visual inspection of in situ hybridisation in mouse brain sections (Lein et al., 2007). Based on these filtering steps, 8 enhancers deemed specific to the MEC were selected.

Figure 2:
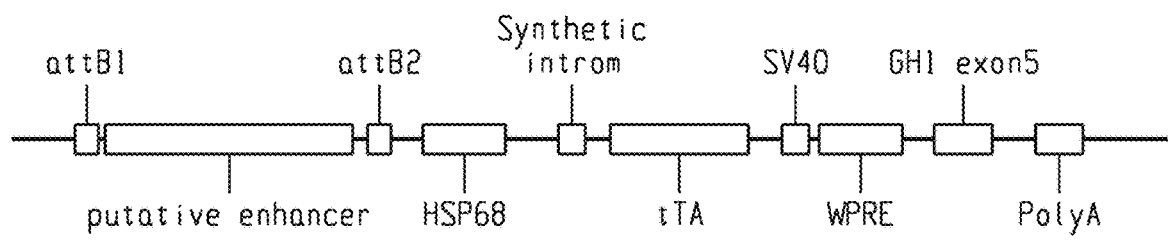
FIG. 2 shows a schematic diagram of the injection construct. The putative enhancer was cloned into the injection construct by Gateway® cloning. The synthetic intron, SV40 intron, WPRE (Woodchuck Hepatitis Virus (WHP) Posttranscriptional Regulatory Element) and growth hormone 1 exon 5 are present for optimal mRNA stability and expression of the tetracycline TransActivator (tTA). The construct is linearized with appropriate restriction enzymes depending on the sequence of the putative enhancer.

Putative enhancer regions were cloned into injection constructs upstream of a mutated HSP68 minimal promoter and the tetracycline transactivator (tTA) gene (FIG. 2), gel purified and injected into the pronucleus of mouse oocytes. Founders were crossed to tTA-dependent histone-bound GFP (hGFP) reporter mice (Jackson laboratory, Tg(tetO154 HIST1H2BJ/GFP)47Efu) for visualisation of expression patterns. The inventors obtained 96 genotypically positive founders from these 8 constructs, 23 of which did not transmit the transgene to the first generation and were discarded. Of the remaining 73, 33 showed no GFP signal in the brain and were also discarded. 36 of the 40 lines that did show expression in the brain expressed signal in the MEC, including at least one from each of the 8 enhancer constructs (FIG. 3).

Figure 4:
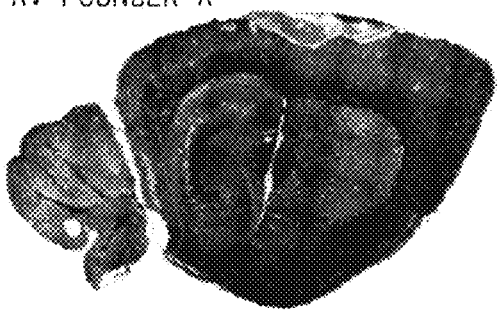
FIG. 4 in panels A-G shows enhancer-driven expression of hGFP in various genomic insertions. The sagittal sections shown are of approximately similar levels of the brain. All mice were crosses of different Odz3-based founders crossed with hGFP mice. Expression in MEC layer II was found in all lines except for founder D.
Figure 4:
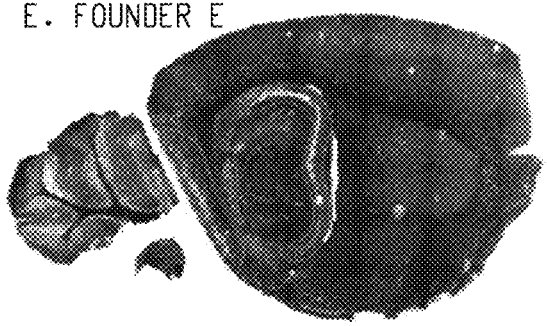
Figure 4:
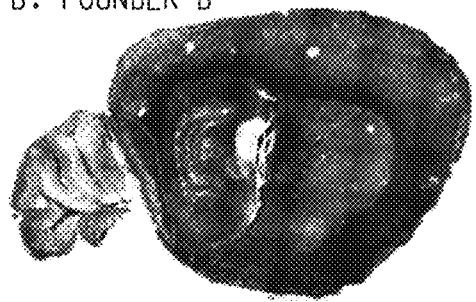
Figure 4:
Figure 4:
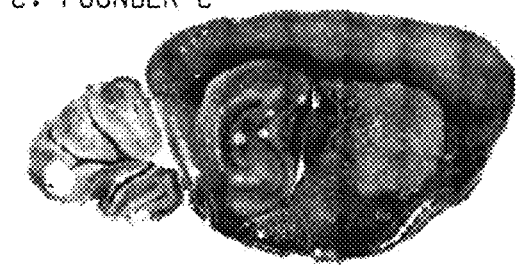
Figure 4:
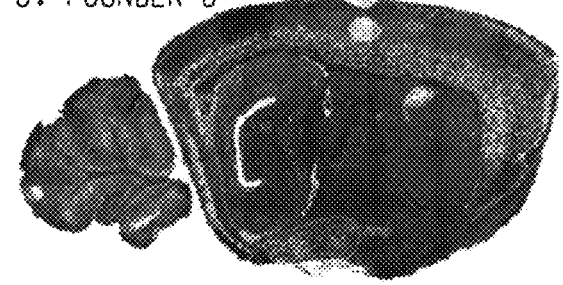
Figure 4:
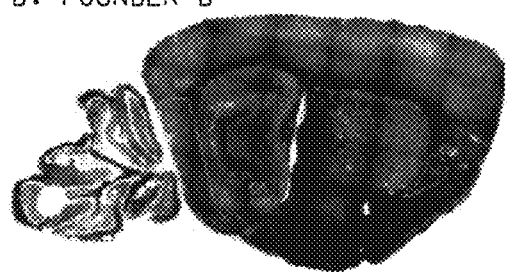

Transgenesis with pronuclear injections inserts the injection construct pseudo-randomly into the genome via non-homologous recombination, leading to what are called insertional effects. There are two basic forms of insertional effects: variable expression and penetrance of transgene expression that is specific to the promoter construct presumably due to the local chromatin environment, and expression that bears no resemblance to that of the promoter construct but is presumably based upon random insertion near local cis-acting regulatory elements which dominate over the promoter construct, i.e. positional effects. FIG. 4 demonstrates that both kinds of insertional effects were seen when multiple founders from the same injection construct were obtained.

Of the 7 lines obtained from enhancer MEC-13-53 (SEQ ID NO: 2), 6 showed GFP expression in Layer II of the entorhinal cortex (EC), one exclusively so. Additionally, some lines showed GFP expression in other brain regions including CA fields in the hippocampus, piriform cortex and scattered expression elsewhere. Line G showed expression in Layer II as well as in deep layers of the LEC and MEC, but also strong expression in the dentate gyrus and deep neocortical layers, whereas line D did not express in the EC but showed strong expression in Purkinje cells, ventral CA2 and the claustrum, which we did not see in other lines made with this construct. Since each founder line has a unique insertional site, the inventors interpret lines A, B, C, E and F as a core pattern of activation with subtle variations resulting from the local chromatin environment, line D as expression dominated by positional effects and line G as a combination of the two. The lines resulting from other enhancer constructs with multiple founders similarly showed core patterns of activation with subtle variations.

By utilizing functional genomics techniques on precisely dissected regions of the brain and quantitative comparisons to many other tissues, robust, reproducible regulatory constructs can be identified that are not strongly affected by position of integration in the genome.

Due to its long half-life (Commerford et al., 1982), any cells labelled with histone GFP during development will likely continue to express the marker well into adult life. Since these enhancers were isolated from adult brain, the inventors crossed some of the more promising founders to other tetO payload lines and performed in situ hybridization (ISH) to determine steady-state transgene expression in adult brain.

Figure 5A:
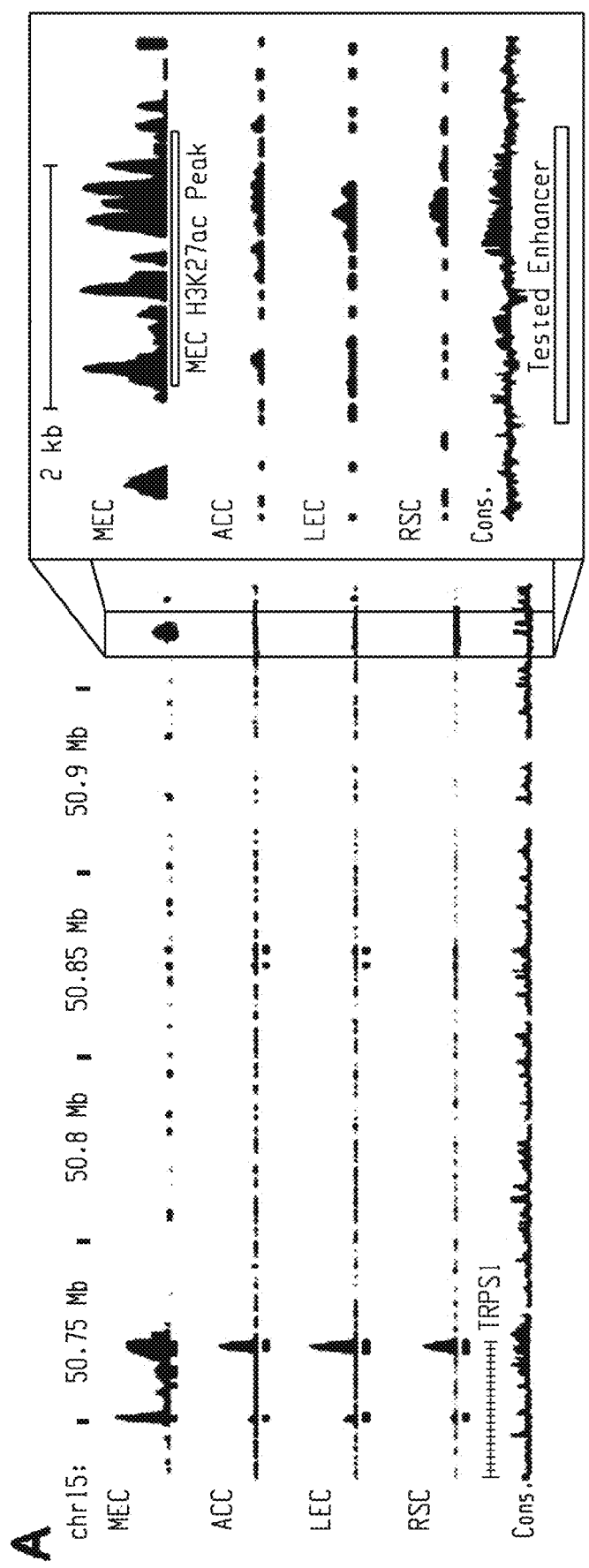

The inventors found that adult expression patterns were in fact significantly more specific than the hGFP crosses, with several of the above MEC-13-53 lines shown in FIG. 4 becoming entorhinal-specific. More importantly, as illustrated in FIG. 5, transgene expression becomes far more specific than the expression pattern of the presumed native gene. FIG. 5A shows an example of the results of bioinformatic analysis of one of the eight MEC enhancers (the putative enhancer was annotated MEC-13-104, its sequence is set forth in SEQ ID NO: 5; the resulting line was named MEC-13-104B) which GREAT associated with the genes Trps1 and Eif3h. Note that the promoter region is a strong peak in all four cortical sub-regions, consistent with expression of the mRNA to varying degrees throughout the cortex (FIG. 5B), but the enhancer peak (FIG. 5A, top right) is greatly enriched in the MEC. However, when mated to an HM3 tetO payload line (Alexander et al., 2009), the expression is almost entirely confined to the MEC (FIG. 5D). This was true for 6 out of the 8 MEC-specific enhancer constructs injected (and may also have been true for the lines terminated based purely upon histone GFP signal.

Figure 6:
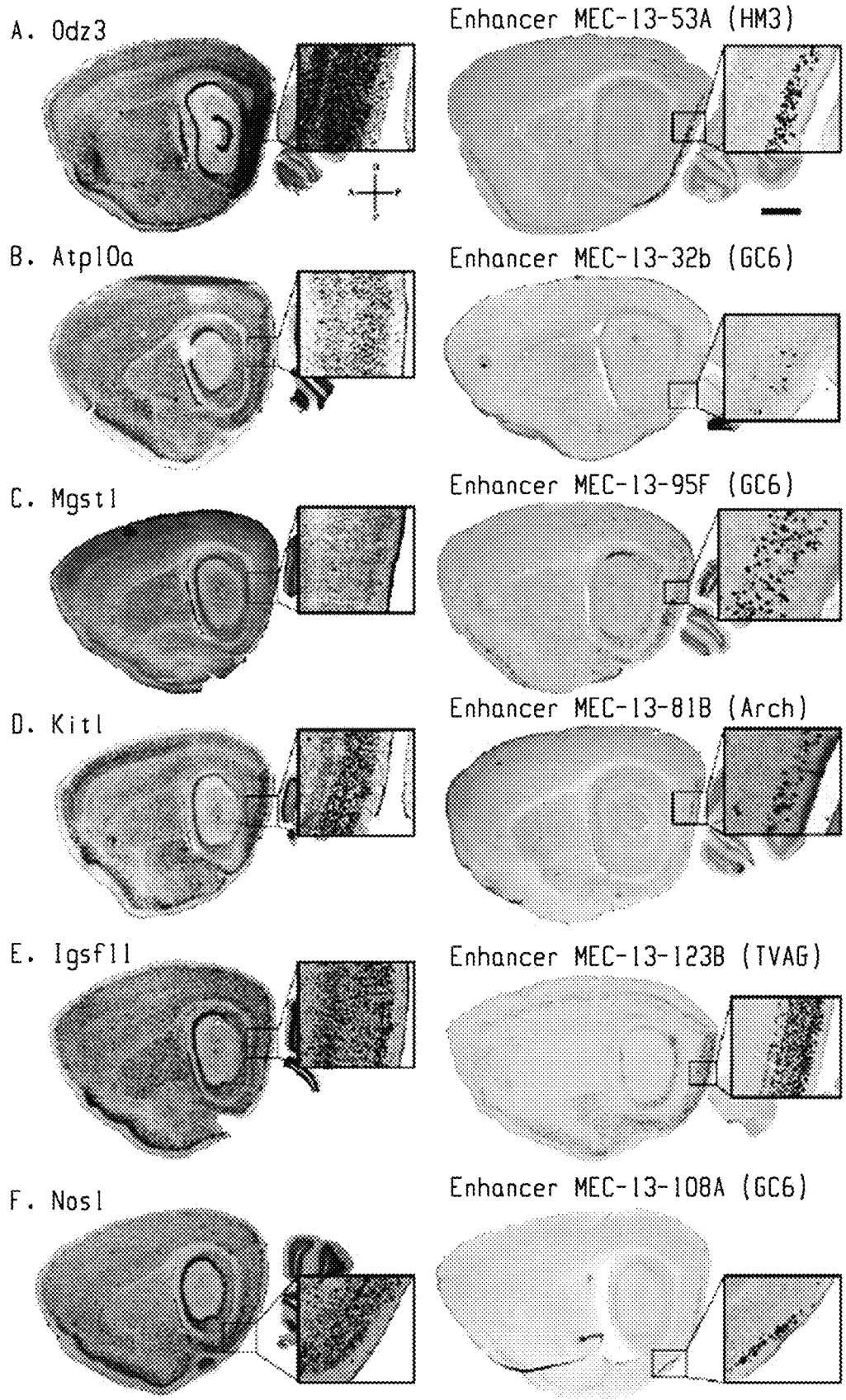
FIG. 6 shows that MEC-specific enhancers drive transgene expression in distinct sets of cells in the MEC. Left-hand column (panels A-F): ISH showing expression patterns of native genes associated with EC-specific enhancers. Right-hand column (panels A-F): ISH showing EC-specific expression of transgenes driven by the corresponding EC-specific enhancers, payload transgene in parentheses. ISH for the native genes from brain-map.org. Scalebar in A is 1000 µm.

FIG. 6 compares the expression patterns of representative transgenic driver lines made with other injection constructs containing either MEC-specific enhancers (FIG. 6A to 6E, right-hand column) or LEC-specific enhancers (FIG. 6F, right-hand panel) compared to the expression pattern of the presumed associated native gene (FIG. 6, left-hand column). Note that while the associated gene is broadly expressed in the brain, the transgenic lines all express more or less specifically in the brain region the enhancers were isolated from. These data show that in essence, one obtains region-specific expression from elements of a non-specific promoter by taking a single region-specific enhancer from it and using it to drive a heterologous core promoter. This in effect solves the problem that most genes are expressed non-specifically in the brain: using EDGE one can obtain specific expression from non-specific promoters.

Region-Specific or Cell-Specific Expression?

The above results show that one can get sub-region specific expression from sub-region specific enhancers. Whether such enhancers drive expression in specific cell types in the targeted brain region is a more difficult question to answer, in large part because there is no consensus as to the number of cell types in the brain or even how to classify them. However, there are indications that these enhancers do specify particular cell types. First of all, the different EC enhancers drive expression in different layers of the EC (FIG. 6), and neurons in different cortical layers are almost by definition different cell types (Cajal, 1899). Since three of the enhancers drive expression in Layer II and three drive expression in Layer III this raises the question of whether the individual enhancers driving layer-specific expression specify the same cell types.

Since there are relatively few neurochemical markers for Layer III of the EC, we investigated the expression of immuno-histochemical markers in two of the three Layer II expressing lines derived from MEC-specific enhancers (FIGS. 7 and 8). Neither of the two enhancers appear to drive expression in inhibitory neurons (For MEC-13-53A, 0/738 transgene expressing cells were GAD+, FIG. 7L, for MEC-13-104B, 0/1579 transgene expressing cells were GAD+, FIG. 8L). Excitatory neurons in EC Layer II are typically further sub-divided into reelin-positive stellate cells and calbindin-positive pyramidal cells (Witter et al., 2017). Line MEC-13-53A expressed exclusively in reelin+ neurons 222 (1162/1162 were reelin+, while only 2/1151 were calbindin+), while line MEC-13-104B appears to roughly correspond to the relative densities of the two cell types (976/1717 were reelin+, while 482/1855 were calbindin+). Thus it appears that MEC-13-53 is a stellate cell specific enhancer, whereas MEC-13-104 is active in all excitatory cells of Layer II, so enhancers can be layer specific and contained to a subset of cells labelled with neurochemical markers within the layer. Neither line expresses in 100% of marked neurons, which could either be due to insertional effects or further sub-divisions of neuronal cell type within groups defined by these neurochemical markers.

There is evidence for a larger degree of functional differentiation within MEC Layer II where both stellate and intermediate stellate cells express Reelin but there is currently no genetic marker that differentiates the two (Fuchs et al., 2016), so the latter possibility is plausible if the morphology and physiology of the two different types of Reelin-expressing cell types are in fact a valid sub-division of neuronal cell types that have corresponding genetic identities.

REFERENCES

Alexander, G. M. et al. (2009), Neuron 63: 27-39
Azevedo, F. A. et al. (2009), Journal of Comparative Neurology 513: 532-541
Betz, W. (1874), Anatomischer Nachweis zweier Gehirncentra. Centralblatt für die medizinischen Wissenschaften: 578-580, 595-599
Boccara, C. N. et al. (2015), Hippocampus 25: 838-857
Bonnavion, P. et al. (2016), Journal of Physiology 594: 6443-6462
Boyden, E. S. et al. (2005), Nature Neuroscience 8: 1263-1268
Brand, A. H. and Perrimon, N. (1993), Development 118: 401-415
Briggs, F. and Callaway, E. M. (2001), Journal of Neuroscience 21: 3600-3608
Brodman, K. (1909), Localisation in the Cerebral Cortex: The Principles of Comparative Localisation in the Cerebral Cortex Based on Cytoarchitectonics (Leipzig: Verlag von Johann Ambrosius Barth)
Cajal, S. R. y. (1899), Comparative study of the sensory areas of the human cortex (Clark University)
Capecchi, M. R. (1989), Science 244: 1288-1292
Chen, X. et al. (2008), Cell 133: 1106-1117
Commerford, S. L. et al. (1982), Proceedings of the National Academy of Sciences of the United States of America 79: 1163-1165
Core, L. J. et al. (2014), Nature Genetics 46: 1311-1320
Cotney, J. et al. (2013), Cell 154: 185-196
Cotney, J. L. and Noonan, J. P. (2015), Cold Spring Harbor Protocols 2015: 419
de Hoon, M. J. et al. (2004), Bioinformatics 20: 1453-1454
DeFelipe, J. et al. (2013), Nature Reviews Neuroscience 14: 202-216
Dimidschstein, J. et al. (2016), Nature Neuroscience 19: 1743-1749
Douglas, R. J. and Martin, K. A. (2007), Current Biology 17: R496-500
The ENCODE Project Consortium (2012), Nature 489: 57-74
Feng, G. et al. (2000), Neuron 28: 41-51
Fogarty, M. et al. (2007), Journal of Neuroscience 27: 10935-10946
Fuchs, E. C. et al. (2016), Neuron 89: 194-208
Habegger, L. et al. (2011), Bioinformatics 27: 281-283
Harris, K. D. and Shepherd, G. M. (2015), Nature Neuroscience 18: 170-181
Heintz, N. (2001), Nature Reviews Neuroscience 2: 861-870
Heintzman, N. D. et al. (2007), Nature Genetics 39: 311-318
Hnisz, D. et al. (2013), Cell 155: 934-947
Huang, Z. J. (2014), Neuron 83: 1284-1302
Hubel, D. H. and Wiesel, T. N. (1962), Journal of Physiology 160: 106-154
Jones, B. F. and Witter, M. P. (2007), Hippocampus 17: 957-976
Kim, T. K. et al. (2010), Nature 465: 182-187
Langmead, B. and Salzberg, S. L. (2012), Nature Methods 9: 357-359
Lein, E. S. et al. (2007), Nature 445: 168-176
Luo, L. et al. (2008), Neuron 57: 634-660
Madisen, L. et al. (2015), Neuron 85: 942-958
Magnus, C. J. et al. (2011), Science 333: 1292-1296
Malik, A. N. et al. (2014), Nature Neuroscience 17: 1330-1339
Maniatis, T. et al. (1987), Science 236: 1237-1245
Mank, M. et al. (2008), Nature Methods 5: 805-811
Mayford, M. et al. (1996), Science 274: 1678-1683
McLean, C. Y. et al. (2010), Nature Biotechnology 28: 495-501

Merkle, F. T. and Alvarez-Buylla, A. (2006), *Current Opinion in Cell Biology* 18: 704-709

Mikkelsen, T. S. et al. (2010), *Cell* 143: 156-169

Nord, A. S. et al. (2013), *Cell* 155: 1521-1531

O'Reilly, K. C. et al. (2015), *Brain Structure and Function* 220: 2873-2893

Parker, S. C. et al. (2013), *Proceedings of the National Academy of Sciences of the United States of America* 110: 17921-17926

Pattabiraman, K. et al. (2014), *Neuron* 82: 989-1003

Paul, A. et al. (2017), *Cell* 171: 522-539

Pinto, L. and Dan, Y. (2015), *Neuron* 87: 437-450

Prabhakar, S. et al. (2008), *Science* 321: 1346-1350.

Quinlan, A. R. and Hall, I. M. (2010), *Bioinformatics* 26: 841-842

Reilly, S. K. et al. (2015), *Science* 347: 1155-1159

Roadmap Epigenomics Consortium (2015), *Nature* 518: 317-330.

Saldanha, A. J. (2004), *Bioinformatics* 20: 3246-3248

Sanyal, A. et al. (2012), *Nature* 489: 109-113

Shen, Y. et al. (2012), *Nature* 488: 116-120

Shima, Y. et al. (2016), *Elife* 5: e13503

Siepel, A. et al. (2005), *Genome Research* 15: 1034-1050

Silberberg, S. N. et al. (2016), *Neuron* 92: 59-74

Soriano, P. (1999), *Nature Genetics* 21: 70-71

Sugar, J. and Witter, M. P. (2016), *Elife* 5: e13925

Taniguchi, H. (2014), *Frontiers in Cellular Neuroscience* 8: 8

Tasic, B. et al. (2016), *Nature Neuroscience* 19: 335-346

Vermunt, M. W. et al. (2014), *Cell Reports* 9: 767-779

Visel, A. et al. (2009), *Nature* 457: 854-858

Visel, A. et al. (2013), *Cell* 152: 895-908 von Bartheld, C. S. et al. (2016), *Journal of Comparative Neurology* 524: 3865-3895 von Economo, C. and Koskinas, G. N. (1925), Cytoarchitectonics of the Adult Human Cerebral Cortex Weible, A. P. et al. (2010), *Journal of Neuroscience* 30: 16509-16513

Weible, A. P. et al. (2014), *Current Biology* 24: 1447-1455

Wickersham, I. R. et al. (2007), *Neuron* 53: 639-647

Witter, M. P. (2011), The hippocampus. In The Mouse Nervous System, G. Paxinos, L. Puilles, and C. Watson, eds. (Academic Press), pp 112-139

Witter, M. P. et al. (2017), *Frontiers in Systems Neuroscience* 11: 46

Zeisel, A. et al. (2015), *Science* 347: 1138-1142

Zeng, H. and Sanes, J. R. (2017), *Nature Reviews Neuroscience* 18: 530-546

Example 2: Viral Delivery of a Gene Under Control of a Murine EC-Specific Enhancer Methods Construct and rAAV (Recombinant AAV) Preparation EDGE-rAAV constructs were synthesised in plasmid pAAV-CMV-β-globin-intron-MCS-WPRE (modified from pAAV-CMV, Agilent, by insertion of the WPRE (SEQ ID NO: 1631) at the MCS). Control constructs were generated as follows: a non-specific rAAV construct, without a region-specific enhancer (non-specific CMV-GFP), was generated by cloning and inserting the eGFP gene into the MCS of the pAAV-CMV plasmid upstream of the WPRE, and removing the β-globin intron; a second, no-promoter control construct, corresponding to the non-specific CMV-GFP construct but lacking a minimal promoter, was generated by inserting the eGFP gene into the MCS of the pAAV-CMV plasmid upstream of the WPRE and removing the CMV promoter and β-globin intron.

To generate experimental constructs, the CMV promoter, β-globin intron, MCS and polyA sequences were removed from pAAV-CMV-β-globin-intron-MCS-WPRE (the WPRE sequence was not removed). A hybrid promoter (consisting of the enhancer and minimal core promoter), transgene (eGFP) and polyA sequence were then cloned into the plasmid in reverse orientation, to circumvent any promoter activity from the 5'ITR. The reverse-orientation hybrid promoter was cloned into the plasmid upstream of the WPRE, which was thus located between the promoter and AAV 3'ITR, forming an insulator from any promoter activity from the AAV 3'ITR. Constructs were generated using the following minimal core promoters: the TRE3G (SEQ ID NO: 1642), FGF4 (SEQ ID NO: 1639), HSV-TK (SEQ ID NO: 1643) and HSP68 (SEQ ID NO: 1630) minimal promoters; and the following murine enhancers: MEC-13-53 (SEQ ID NO: 2), MEC-13-104 (SEQ ID NO: 5) and LEC-13-8 (SEQ ID NO: 9). The LEC-13-8 enhancer sequence was synthesised by Genscript, USA. The TRE3G minimal promoter (mTRE3G) is the minimal promoter from the TRE3G promoter (Clontech), and corresponds to a mutated form of the CMV minimal promoter (mCMV). mTRE3G may alternatively be referred to as mCMV*.

The minimal promoter sequence and transgene were first cloned into the plasmid. Each minimal promoter sequence (in reverse orientation) was cloned into the plasmid such that it was flanked by the MCS at the 3' end, into which enhancer sequences could be cloned, and the eGFP-sequence with stop signal at the 5' end. Enhancer sequences were PCR amplified using primers with flanking restriction enzyme sites for EcoR1 and Sal1 and cloned into the MCS.

Plasmids were maintained in the Stbl3 *E. coli* strain (ThermoFisher) to avoid ITR-mediated recombination. Positive clones were confirmed by restriction digestion analyses and subsequently by DNA sequencing. Endotoxin-free plasmid maxipreps (Qiagen) were made for rAAV preparations.

The above-described cloning procedures yielded experimental vectors such as that shown in FIG. 9. The WPRE has the sequence set forth in SEQ ID NO: 1631; the promoter shown in the figure is the TRE3G minimal promoter (SEQ ID NO: 1642). The enhancer and promoter control the expression of the enhanced GFP gene (eGFP). The construct is in reverse orientation in the pAAV plasmid. An additional control pAAV plasmid was also synthesized, which lacked any enhancer but was otherwise identical to an experimental plasmid. This "no-enhancer" control contained the TRE3G promoter.

The synthesised plasmids were incorporated into AAV serotype 2/1 using standard methods. Specifically, a pAAV plasmid synthesized as described above (either the experimental plasmid containing the enhancer or a control plasmid), along with AAV plasmids encoding the structural elements of the AAV, were transfected into the AAV-293 cell line (Agilent), a HEK293T-derived cell line optimised for packaging of AAV virions. The day before transfection, $7\times10^6$ AAV-293 cells were seeded into 150 mm cell culture plates in DMEM containing 10% fetal bovine serum (ThermoFisher) and penicillin/streptomycin. Calcium chloride-mediated co-transfection was performed using 22.5 μg pAAV-containing the transgene, 22.5 μg pHelper and 5.6 μg each of pRC (Agilent) and pXR1 (NGVB, USA) capsid plasmids. After 7 hours, the medium was replaced with fresh 10% FBS-containing DMEM. The AAV-293 cells were cultured for two or three days following transfection to allow AAV synthesis to occur, whereafter the cells were lysed. The AAVs were isolated by standard procedures culminating in heparin column purification.

Specifically, the AAV-293 cells were scraped from the cell culture plates, then isolated by centrifugation at 200×g. The cell pellet was then subjected to lysis using 150 mM NaCl-20 mM Tris pH 8 buffer containing 10% sodium deoxycholate. The lysate was treated with Benzonase nuclease HC (Millipore) for 45 minutes at 37° C. Benzonase-treated lysate was centrifuged at 3000×g for 15 mins and the clear supernatant then subjected to HiTrap® Heparin High Performance (GE) affinity column chromatography using a peristaltic pump (McClure C *JOVE* 2011). The elute from the Heparin column was concentrated using Amicon® Ultra centrifugal filters (Millipore). The titre of the resultant viral stock was determined as approximately $10^8$ infectious particles/ml.

Rodent Details

Experiments were carried out using C57BL/6J mice obtained from Jackson laboratory and Long Evans rats. All mice and rats were housed in enriched environment cages according to the Norwegian Food Safety Authority approved protocol in a 12 hr light/dark cycle with food and water ad libitum.

Stereotaxic Injections and Perfusions

For rat experiments, the rAAVs were stereotactically injected into three-to-four month old Long-Evans rats. Injections were performed with rAAV at a titre of $\sim 1\times10^8$ infectious particles/ml, into the MEC of the rats. The rats were deeply anaesthetised with isoflurane gas (induction with 5% isoflurane (v/v), maintenance at 1% isoflurane (v/v), airflow of 1200 ml/min). To maintain the body temperature of the animal, a heating pad at 37° C. was used.

Rats were injected subcutaneously with buprenorphine hydrochloride (Temgesic®, Indivior) and Metacam® (Boehringer Ingelheim Vetmedica) at the prescribed dosage. Local anaesthetic Bupivacaine hydrochloride (Marcain™, AstraZeneca) was applied at the place of incision. The head was fixed to the stereotaxic frame with ear bars, and the skin at the incision site was disinfected with 70% ethanol and iodide before the incision was made using a sterile surgical scalpel blade. After incision, the mouthpiece and ear bars were adjusted so that bregma and lambda were aligned horizontally. Mediolateral coordinates were measured from the mid-sagittal sinus, anterior-posterior coordinates were measured from posterior transverse sinus, and dorso-ventral coordinates were measured from the surface of the brain. A craniotomy was made around the approximate coordinate, and precise measurements were made with the glass capillary used for virus injection. Coordinates for rat injections were 4.6 mm lateral, 0.2 mm anterior to the posterior transverse sinus and 2.6 mm deep, with the glass capillary lowered at 10° pointing towards the nose. 1000 or 1500 nl virus injections were conducted at a speed of 100 nl/min using a glass capillary and a nanoliter injector (Nanoliter2010, World Precision Instruments, Sarasota, Fla., USA), controlled by a microsyringe pump controller (Micro4 pump, World Precision Instruments). After completion of the injection, the capillary was retracted after a 10 minute delay, to give the virus time to diffuse. Finally, the wound was rinsed with saline and the skin was sutured. The animals were left to recover in a heating chamber, before being returned to their home cage, where their health was checked daily.

For mouse experiments, 10-15 week-old adult C57BL/6J mice were anaesthetised with isoflurane (induction with 5% isoflurane (v/v), maintenance with 1% isoflurane (v/v), airflow of 1200 ml/min). After applying the local analgesic Marcain™ (Astra Zeneca, 40 µl, 0.25 mg/ml, SC), the global analgesic buprenorphine (Temgesic®, 0.03 mg/ml, 100-150 µl per mouse dependent on bodyweight, SC), and meloxicam (Metacam®, 2.5 mg/ml, 100-150 µl per mouse dependent on bodyweight, SC) the head was fixed in a stereotaxic frame. Subsequently the skull was exposed by a single incision of the scalp, craniotomies were made approximately 5 mm posterior and 3.3 mm lateral of the bregma. Then, the virus solution was injected at a location 0.3-0.5 mm anterior to the transverse sinus and at a depth of 1.8-2.0 mm from the brain surface. Unless otherwise stated, all injections were bilateral injections of 400 nl rAAV injected at a rate of 50 nl/min. Mice were given a second post-operative injection of Metacam® the next day, and their weight was monitored until stable.

After 4 weeks, the rodents were sacrificed. Rodents were anaesthetised with pentobarbital and perfused transcardially with 0.9% saline followed by 4% paraformaldehyde in 0.9% saline, and their brains removed and sectioned as described in Example 1 with respect to mice. Brain sections were then immunostained as described below. In situ hybridisation experiments were performed as described in Example 1.

Immunostaining

Horizontal rat brain sections of 50 µm were prepared using a sliding microtome. Brain sections were stored at −20° C. in 0.1 M phosphate buffer containing 25% glycerin and 30% ethylene glycol. Multiple labelling of free-floating sections was carried out as briefly described. Every sixth section in the series was selected for immunostaining and washed in phosphate-buffered saline (PBS). Sections were permeabilised and blocked for 1 hour at room temperature using PBS containing 0.1% Triton X-100 and 3% normal donkey serum, or, when staining for reelin and calbindin 0.5% Triton X-100 and 5% goat serum and when staining for NeuN 0.3% Triton X-100 and 3% BSA (PBS++). Sections were subsequently incubated with primary antibodies in PBS++ at 4° C. for two days with mild shaking. PBS-washed sections were incubated for 2 hours at room temperature with secondary antibodies diluted in PBS++ (or PBS containing Triton X-100 without serum/BSA).

Solution containing 2.5% 1,4-diazabicylo[2.2.2]octane/ polyvinyl alcohol (DABCO/PVA) was used to mount the sections in Polysine slides (Menzel-Glaser, Thermo Scientific). Antibodies used were rabbit anti-GFP (ThermoFisher/ Life technologies A11122, 1:500), mouse anti-Reelin (Merck Millipore MAB5364, 1:1000), mouse anti-Calbindin (Swant D-28 K, CB300, 1:5000), mouse anti-NeuN (Merck Millipore MAB377, 1:1000) and rabbit anti-2A peptide (Merck Millipore ABS31, 1:2000). All corresponding secondary antibodies were from ThermoFisher/Life technologies or Jackson ImmunoResearch laboratories, 1:400.

Confocal Imaging and Analysis

Sections were imaged using a confocal microscope (Zeiss LSM 880, Zen 2012 software) with either Plan-Apochromat 40×/1.4 Oil DIC M27 oil immersion or Plan-Apochromat 20×/0.8 air immersion objectives. The quantification of GFP+, reelin+ or calbindin+ cells was carried out manually using Zen 2012 software. Approximately ten 50 µm thick horizontal sections were selected evenly from the dorso-ventral axis per brain. Imaging and analyses were conducted by the same person to control inter-analyst variation. Scale bar=100 µm.

Results
Generation of a Cell Type-Specific Viral Vector

The inventors' goal was to obtain cell type-specific expression, rather than cell type-specific infection. There are a number of published accounts claiming distinct tropism for different serotypes of AAV (Watakabe, A. et al., 2015; Aschauer, D. F. et al., 2013). The inventors therefore restricted their analysis to a single serotype, AAV2/1, which has a mosaic capsid of serotypes 1 and 2 (Hauck et al., 2003) and is commonly used to infect rodent neurons, and a single enhancer that gave highly specific transgene expression (MEC-13-53). FIG. 11A shows the expression pattern obtained in a murine transgenic cross in which TVAG transgene expression using MEC-13-53 is demonstrated. Expression in this line was limited to reelin-positive (Reln+), calbindin-negative (CB−) excitatory projection neurons in layer II of the medial and lateral EC (i.e. stellate and fan cells, respectively (Kitamura, T. et al., 2014; Varga, C. et al., 2010; Witter, M. P. et al., 2017)).

The inventors realised that in order to obtain results with similar degrees of specificity with viral vectors, it was first necessary to find a minimal viral construct which by itself did not significantly express in infected neurons. Because viral ITRs themselves have transcriptional activity (Flotte, T. R. et al., 1993; Haberman, R. P. et al., 2000), the inventors reversed the orientation of the GFP reporter transgene and minimised the effect of the 3' ITR by using the WPRE as an insulator (Zufferey, R., et al., 1999), such that the sense strand would exclusively be under the control of the exogenous promoter (as shown in FIG. 9). The reverse-orientated design substantially reduced the background expression in other layers (FIG. 11C-E). The inventors screened four different minimal promoters that have been used for transcriptional assays including HSP68, the same heterologous minimal promoter used successfully for transgenesis (see Example 1). The results can be seen in FIG. 12C-F, suggesting that EDGE-based anatomical specificity is attainable using different minimal promoters. Due to the size limitation of rAAVs, the TRE3G minimal promoter (Loew, R. et al., 2010) was selected for subsequent experiments as it was the smallest minimal promoter that yielded layer specific EDGE and had low background expression.

MEC13-53 EDGE rAAVs Express Specifically in Layer II Stellate Cells in Wildtype Mice The layer specificity of the MEC-13-53 EDGE virus was further confirmed by NeuN counterstaining (FIG. 13A), which drove the inventors to investigate the principal type of cells targeted by the MEC-13-53 enhancer. Two principal types of neurons, Reln+ and CB+ cells, are observed in MEC layer II using cell type-specific immunomarkers. In rodents, Reln+ cells in MEC layer II form the sole excitatory projection to the dentate gyrus, while calbindin+ neurons do not (or only sparsely) project to the hippocampal formation. Intriguingly, MEC13-53 EDGE was observed exclusively in Reln+ and not in the clusters of CB+ cells in the MEC (FIG. 13C-D). MEC injections of control virus without enhancer (rAAV TRE3G-GFP) resulted in non-layer specific GFP expression surrounding the injection site (FIG. 13B).

Enhancer-Guided Layer-Specific Transgene Expression Works Across Species

To investigate whether mouse EDGE rAAVs retain their layer/cell specificity in a second species, the MEC-13-53 rAAV we stereotaxically introduced into the MEC of wild-type Long Evans rats. Surprisingly, MEC-13-53 EDGE was even more specific for MEC layer II in rats: in the brains of rats injected with the MEC-13-53 rAAV, strong and highly localised GFP expression was seen in the MEC (FIG. 10A). In addition, injections of control viruses in rats produced even lower levels of basal GFP expression than in mice (FIG. 10B). Similar to EDGE rAAV in mice, MEC-13-53-EDGE expression was detected almost exclusively in Reln+ cells and CB− cells (FIG. 10C-D). Of the 1803 GFP+ cells, 100% of them were Reln+ while a mere 1.83±0.68% were CB+ (29 out of 1589). Layer II-specific GFP expression was evident in multiple sections in the dorso-ventral axis of the MEC (FIG. 14).

Other EDGE rAAVs Recapitulate the Expression Pattern of the Corresponding Transgenic Crosses To examine whether the EDGE rAAVs could recapitulate the EDGE pattern seen in transgenic crosses, a comparative transgene expression analysis were carried out on multiple enhancer EDGEs. EDGE from the transgenic crosses was determined by ISH using the respective transgene probes, and enhancer driven GFP expression from the corresponding EDGE viruses was analysed by immunostaining. MEC-13-104 and LEC-13-8 showed characteristic transgene expression patterns in transgenic mice (FIGS. 15A&C) that were recapitulated by the corresponding EDGE rAAVs (FIGS. 5B&D)

REFERENCES

Aschauer, D. F. et al. (2013), *PLoS One* 8: e76310
Flotte, T. R. et al. (1993), *Journal of Biological Chemistry* 268: 3781-3790
Haberman, R. P. et al. (2000), *Journal of Virology* 74: 8732-8739
Kitamura, T. et al. (2014), *Science* 343: 896-901
Loew, R. et al. (2010), *BMC Biotechnology* 10: 81
Varga, C. et al. (2010) *Nature Neuroscience* 13: 822-824
Watakabe, A. et al. (2015), *Neuroscience Research* 93: 144-157
Witter, M. P. et al. (2017), *Frontiers in Systems Neuroscience* 11: 46
Zufferey, R. et al. (1999), *Journal of Virology* 73: 2886-2892

The use of the terms "a" and "an" and "the" and similar referents (especially in the context of the following claims) are to be construed to cover both the singular and the plural, unless otherwise indicated herein or clearly contradicted by context. The terms first, second etc. as used herein are not meant to denote any particular ordering, but simply for convenience to denote a plurality of, for example, layers. The terms "comprising", "having", "including", and "containing" are to be construed as open-ended terms (i.e., meaning "including, but not limited to") unless otherwise noted. Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein.

While the invention has been described with reference to an exemplary embodiment, it will be understood by those skilled in the art that various changes may be made and

SEQUENCE LISTING

The patent contains a lengthy "Sequence Listing" section. A copy of the "Sequence Listing" is available in electronic form from the USPTO web site (https://seqdata.uspto.gov/?pageRequest=docDetail&DocID=US11364309B2). An electronic copy of the "Sequence Listing" will also be available from the USPTO upon request and payment of the fee set forth in 37 CFR 1.19(b)(3).

The invention claimed is:

1. A delivery vehicle comprising a nucleic acid construct, wherein the nucleic acid construct comprises:
    (i) an enhancer which specifically drives gene expression in cells of the entorhinal cortex, wherein the enhancer comprises a nucleotide sequence selected from SEQ ID NOs: 1-6, 9, and 10;
    (ii) a promoter; and
    (iii) a therapeutic gene,
    wherein said enhancer, promoter and therapeutic gene are operatively linked, said enhancer and therapeutic gene are heterologous, and said delivery vehicle is suitable for delivery of the nucleic acid construct to the brain of a mammal.

2. The delivery vehicle of claim 1, wherein said promoter is a minimal promoter.

3. The delivery vehicle of claim 1, wherein said promoter is heterologous to said enhancer.

4. The delivery vehicle of claim 1, wherein said enhancer specifically drives gene expression in cells of Layer II of the entorhinal cortex.

5. The delivery vehicle of claim 4, wherein said enhancer specifically drives gene expression in reelin-positive cells.

6. The delivery vehicle of claim 1, wherein said enhancer is human.

7. The delivery vehicle of claim 1, wherein said promoter is selected from an HSP68 minimal promoter, a TRE3G promoter, a TRE3G minimal promoter, a TK minimal promoter, an FGF4 minimal promoter, an Odz3 minimal promoter, or a variant of any one or more of the foregoing promoters.

8. The delivery vehicle of claim 1, wherein said delivery vehicle is a lipoplex, dendrimer, exosome or viral vector.

9. The delivery vehicle of claim 8, wherein said viral vector is an adeno-associated virus (AAV).

10. The delivery vehicle of claim 1, wherein said therapeutic gene encodes a protein or a functional RNA.

11. The delivery vehicle of claim 10, wherein said functional RNA is an shRNA.

12. The delivery vehicle of claim 1, wherein said therapeutic gene encodes an α secretase, neprilysin, PGC-1α, LSD1, an inhibitor of glycogen synthase kinase 3, or a Tau phosphorylation pseudosubstrate.

13. A cell comprising a nucleic acid construct as defined in claim 1.

14. A composition comprising a delivery vehicle as defined in claim 1 and at least one physiologically-acceptable diluent, carrier or excipient.

* * * * *